US010434112B2

(12) United States Patent
Viswanath et al.

(10) Patent No.: US 10,434,112 B2
(45) Date of Patent: Oct. 8, 2019

(54) USE OF AGONISTS OF FORMYL PEPTIDE RECEPTOR 2 FOR TREATING DERMATOLOGICAL DISEASES

(71) Applicant: Allergan, Inc., Irvine, CA (US)

(72) Inventors: Veena Viswanath, Irvine, CA (US); Richard L. Beard, Newport Beach, CA (US); John E. Donello, Dana Point, CA (US); Edward Hsia, Irvine, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 15/490,127

(22) Filed: Apr. 18, 2017

(65) Prior Publication Data

US 2017/0216326 A1 Aug. 3, 2017

Related U.S. Application Data

(63) Continuation of application No. 14/196,155, filed on Mar. 4, 2014, now abandoned.

(Continued)

(51) Int. Cl.
*A61K 31/195* (2006.01)
*A61K 31/683* (2006.01)
*C07F 9/40* (2006.01)
*C07C 235/82* (2006.01)
*C07C 275/42* (2006.01)
*C07D 217/24* (2006.01)
*C07D 223/10* (2006.01)
*C07D 233/80* (2006.01)
*C07D 235/02* (2006.01)
*C07D 257/04* (2006.01)
*C07D 261/12* (2006.01)
*C07D 401/06* (2006.01)
*C07D 405/06* (2006.01)
*C07D 405/14* (2006.01)
*C07D 409/06* (2006.01)
*A61P 17/12* (2006.01)
*A61P 17/02* (2006.01)
*A61P 35/00* (2006.01)
*A61P 17/18* (2006.01)
*A61P 17/10* (2006.01)
*A61P 17/04* (2006.01)
*A61P 17/14* (2006.01)
*A61P 17/06* (2006.01)
*A61P 17/16* (2006.01)

(Continued)

(52) U.S. Cl.
CPC .......... *A61K 31/683* (2013.01); *A61K 9/0014* (2013.01); *A61K 31/167* (2013.01); *A61K 31/17* (2013.01); *A61K 31/192* (2013.01); *A61K 31/196* (2013.01); *A61K 31/4045* (2013.01); *A61K 31/41* (2013.01); *A61K 31/4166* (2013.01); *A61K 31/4174* (2013.01); *A61K 31/4178* (2013.01); *A61K 31/42* (2013.01); *A61K 31/472* (2013.01); *A61K 31/4725* (2013.01); *A61K 31/55* (2013.01); *A61K 31/662* (2013.01); *A61P 17/02* (2018.01); *A61P 17/04* (2018.01); *A61P 17/06* (2018.01); *A61P 17/10* (2018.01); *A61P 17/12* (2018.01); *A61P 17/14* (2018.01); *A61P 17/16* (2018.01); *A61P 17/18* (2018.01); *A61P 35/00* (2018.01); *C07C 235/82* (2013.01); *C07C 275/42* (2013.01); *C07D 217/24* (2013.01); *C07D 223/10* (2013.01); *C07D 233/80* (2013.01); *C07D 235/02* (2013.01); *C07D 257/04* (2013.01); *C07D 261/12* (2013.01); *C07D 401/06* (2013.01); *C07D 405/06* (2013.01); *C07D 405/14* (2013.01); *C07D 409/06* (2013.01); *C07F 9/40* (2013.01)

(58) Field of Classification Search
CPC .. A61K 31/17; A61K 31/196; A61K 31/4166; A61K 31/42; A61K 31/662; C07C 235/82; C07C 275/42; C07D 217/24; C07D 223/10; C07D 233/80; C07D 235/02; C07D 257/04; C07D 261/12; C07D 401/06; C07D 405/06; C07D 405/14; C07D 409/06; C07F 9/40; A61P 17/00; A61P 17/02; A61P 17/04; A61P 17/06; A61P 17/10; A61P 17/12; A61P 17/14; A61P 17/16; A61P 17/18; A61P 35/00
USPC ........ 514/115, 218, 309, 380, 381, 390, 563
See application file for complete search history.

(56) References Cited

U.S. PATENT DOCUMENTS 4,521,210 A 6/1985 Wong
7,820,673 B2 10/2010 Kubo et al.
(Continued)

FOREIGN PATENT DOCUMENTS

JP 63232846 9/1988
KR 2009-0121832 11/2009
(Continued)

OTHER PUBLICATIONS

Chiang N, et al., The lipoxin receptor ALX: Potent ligand-specific and stereoselective actions in vivo. Pharmacological Reviews 2006; 58: 463-519.

(Continued)

Primary Examiner — My-Chau T. Tran
(74) Attorney, Agent, or Firm — Jonathan Bass

(57) ABSTRACT

The present invention relates to a method for treating dermal inflammation and dermal diseases by local or systemic delivery, in a subject in need of such treatment, which comprises administering a pharmaceutical composition comprising a therapeutically effective amount of at least one agonist of Formyl peptide receptor 2 (FPR2).

4 Claims, 3 Drawing Sheets

Related U.S. Application Data

(60) Provisional application No. 61/773,778, filed on Mar. 6, 2013.

(51) Int. Cl.

| | | |
|---|---|---|
| *A61K 31/17* | (2006.01) | |
| *A61K 31/196* | (2006.01) | |
| *A61K 31/4166* | (2006.01) | |
| *A61K 31/42* | (2006.01) | |
| *A61K 31/662* | (2006.01) | |
| *A61K 9/00* | (2006.01) | |
| *A61K 31/167* | (2006.01) | |
| *A61K 31/192* | (2006.01) | |
| *A61K 31/4045* | (2006.01) | |
| *A61K 31/41* | (2006.01) | |
| *A61K 31/4174* | (2006.01) | |
| *A61K 31/4178* | (2006.01) | |
| *A61K 31/472* | (2006.01) | |
| *A61K 31/4725* | (2006.01) | |
| *A61K 31/55* | (2006.01) | |

(56) References Cited

U.S. PATENT DOCUMENTS

| | | | |
|---|---|---|---|
| 8,440,684 B2 | 5/2013 | Beard | |
| 8,492,556 B2 | 7/2013 | Beard et al. | |
| 8,507,560 B2 | 8/2013 | Beard | |
| 8,541,577 B2 | 9/2013 | Beard et al. | |
| 8,580,817 B2 | 11/2013 | Beard et al. | |
| 8,618,163 B2 * | 12/2013 | Beard | A61K 31/16 514/510 |
| 8,653,299 B2 | 2/2014 | Vuligonda | |
| 8,658,803 B2 * | 2/2014 | Beard | C07C 275/30 548/338.1 |
| 8,729,096 B2 | 5/2014 | Beard | |
| 8,809,367 B2 | 8/2014 | Beard | |
| 8,816,076 B2 * | 8/2014 | Beard | C07C 275/30 544/292 |
| 8,846,760 B2 | 9/2014 | Beard | |
| 8,993,780 B2 * | 3/2015 | Beard | C07C 275/30 548/338.1 |
| 9,351,948 B2 * | 5/2016 | Beard | C07C 275/30 |
| 9,428,549 B2 * | 8/2016 | Beard | C07C 275/30 |
| 9,579,307 B2 * | 2/2017 | Beard | C07C 275/30 |
| 9,670,150 B2 * | 6/2017 | Beard | C07C 309/15 |
| 9,850,264 B2 * | 12/2017 | Beard | A61K 9/0048 |
| 9,974,772 B2 * | 5/2018 | Beard | C07C 275/30 |
| 10,172,832 B2 * | 1/2019 | Beard | C07C 275/30 |
| 2002/0052417 A1 | 5/2002 | Klingler | |
| 2005/0137230 A1 | 6/2005 | Dorsch et al. | |
| 2011/0144033 A1 | 6/2011 | Bernardini | |
| 2011/0319454 A1 | 12/2011 | Beard | |
| 2012/0142726 A1 | 6/2012 | Beard et al. | |
| 2012/0238628 A1 | 9/2012 | Vuligonda et al. | |
| 2012/0329873 A1 | 12/2012 | Li et al. | |
| 2013/0109866 A1 | 5/2013 | Beard et al. | |
| 2013/0123215 A1 | 5/2013 | Beard et al. | |
| 2013/0217720 A1 | 8/2013 | Beard et al. | |
| 2013/0274230 A1 | 10/2013 | Beard et al. | |
| 2014/0256684 A1 | 9/2014 | Beard | |
| 2015/0025021 A1 | 1/2015 | Beard et al. | |
| 2015/0080466 A1 | 3/2015 | Beard | |
| 2016/0272581 A1 | 9/2016 | Beard | |

FOREIGN PATENT DOCUMENTS

| | | |
|---|---|---|
| WO | 2001-014328 | 3/2001 |
| WO | 2006065755 | 6/2006 |
| WO | 2006065755 A2 | 6/2006 |
| WO | 2007076055 | 7/2007 |
| WO | 2010104307 | 9/2010 |
| WO | 2013-009543 | 1/2013 |
| WO | 2013-070600 | 5/2013 |
| WO | 2013062947 | 5/2013 |

OTHER PUBLICATIONS

Dufton N, et al., Therapeutic anti-inflammatory potential of formyl peptide receptor agonists. Pharamcology & Therapeutics 2010; 127: 175-188.

Dufton N, et al., Anti-inflammatory role of the murine formyl-peptide receptor 2: Ligand-specific effects on leukocyte responses and experimental inflammation. Journal of Immunology 2010; 184: 2611-2619.

Madema P, et al., FPR2/ALX receptor expression an dinternalization are critical for lipoxin A4 and annexin-derived peptide-stimulated phagocytosis, FASEB 2010; 24: 4240-4249.

Reville K, et al., Lipoxin A4 redistributes Mysoin IIA and Cdc42 in macrophages: Implications for phagocytosis of apoptotic leukocytes. Journal of Immunology 2006; 176: 1878-1888.

Serhan C. Resolution phase of inflammation: Novel endogenous anti-inflammatory and proresolving lipid mediators and pathways, Annual reviews of Immunology 2007; 25: 101-137.

Medeiros R, et al., Molecular mechanisms of topical anti-inflammatory effects of lipoxin A(4) in endotoxin-induced uveitis. Molecular Pharmacology 2008; 74: 154-161.

Gronert K, et al., A role for the mouse 12/15-lipoxygenase pathways in promoting epithelial wound healing and host defense. Journal of Biological Chemistry 2005; 280: 15267-15278.

Leedom A, et al., Endogenous LXA4 circuits are determinants of pathological angiogenesis in response to chronic injury. American Journal of Pathology 2010; 176: 74-84.

Gronert K. Lipoxins in the eye and their role in wound healing. Prostaglandins, Leukotrienes and Essential fatty Acids. 2005; 73: 221-229.

Gavins FNE, Hughes EL, Buss NAPS, Holloway PM, Getting SJ, Buckingham JC. Leukocyte recruitment in the brain in sepsis: involvement of the annexin1 FPR2IALX anti-inflammatory system. FASEB 2012; 26: 1-13.

Takano T, Fiore S, Maddox JF, Brady HR, Petasis NA, Serhan CN. Asprin-triggered 15-epi-lipoxin A4 and LXA4 stable analogues are potent inhibitors of acute inflammation: evidence for antiinflammatory receptors. Journal of Experimental Medicine 1997; 185: 1693-1704.

Leoni G, Alam A, Neumann PA, Lambeth JD, Cheng G, McCoy J, Hilgarth RS, Kundu K, Murthy N, Kusters D, Reutelingsperger C, Perretti M, Parkos CA, Neish AS, Nusrat A, Annexin A 1, formyl peptide receptor, and NOX1 orchestrate epithelial repair. Journal of Clinical Investigation. 2013; 123:443-54.

Tsuruki T, Takahata K, Yoshikawa M. Mechanism of the protective effect of intraperitoneally administered agonists for formyl peptide receptors against chemotherapy-induced alopecia. Biosci Biotechnology Biochemistry. 2007;71: 1198-202.

Yamasaki K, Di Nardo A, Bardan A, Murakami M, Ohtake T, Coda A, Dorschner RA, Bonnari C, Descargues P, Hovnanian A, Morhenn VB, Gallo RL. Increased serine protease activity and cathelicidin promotes skin inflammation in rosacea. Nature Medicine. 2007;13:975-80.

Czernilofsky et al., Affinity label for the tRNA binding site on the *Escherichia coli* ribosome, Biochimica et Biophysica Acta, 272 (1972) 667-671.

Felicity N. E. Gavins et al., Leukocyte recruitment in the brain in sepsis: involvement of the annexin 1-FPR2/ALX anti-inflammatory system, The FASEB Journal, vol. 26 Dec. 2012.

Kazuo Iwaki et al., Optical Resolution of Enantiomeric Amino Acid Derivatives on a Naphthylethylurea Multiple-Bonded Chiral Stationary Phase Prepared via an Activated Carbamate Intermediate, Journal of Chromatography, 404 (1987) 117-122.

K. Iwaki et al., Preparation of Chiral Stationary Phase via Activated Carbamate Intermediate for Liquid Chromatographic Optical Resolution, Chromatographia vol. 23, No. 10, Oct. 1987.

International Search Report PCT/US2013/036715, dated Jun. 28, 2013.

(56) References Cited

OTHER PUBLICATIONS

Migeotte. Isabelle, et al., Formyl peptide receptors: A promiscuous subfamily of G protein-coupled receptors controlling immune reponses, Cytokine & Growth Factor Reviews 17, 2006, pp. 501-519.
Cross, L.C., Rules for the Nomenclature of Organic Chemistry Section E: Stereochemistry, International Union of Pure and Applied Chemistry, vol. 45,1976, pp. 11-13.
Stahl, Heinrich P., et al., Handbook of Pharmaceutical Salts Properties, Selection, and Use, International Union of PurE and Applied Chemistry, 2002, pp. 329-345, Verlag Helvetica Chimica Acta, Zurich.
Tsuruki, Takahiro et al., Orally administered FPRL1 receptor agonist peptide MMK-1 inhibits etoposide-induced alopecia by a mechanism different from intraperitoneally administered MMK-1, Peptides, 2006, 820-825, 27, US.
International Search Report dated Jul. 18, 2014, for PCT Application No. PCT/US2014/020273 filed Mar. 4, 2014, 6 pages.
ROLAND BURLI, Potent hFPRL1 (ALXR) Agonists as Potential Anti-Inflammatory Agents, Bioorganic & Medicinal Chemistry Letters, 2006, 3713-3718, 16.
Schepetkin, I., et al., 3-(1H-indol-3-yl)-2-[3-(4-nitrophenyl)ureido]propanamide enantiomers with human formyl-peptide receptor agonist activity: Molecular modeling of chiral recognition by FPRZ, Biohem. Pharmacol., 2013, 404-416, 85(3).

\* cited by examiner

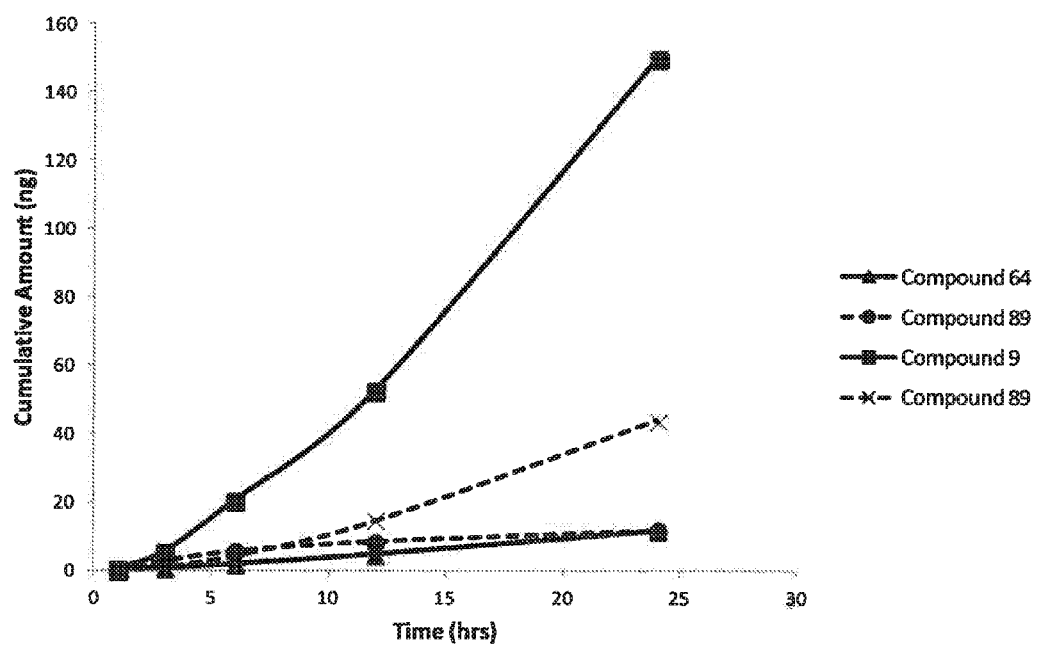

USE OF AGONISTS OF FORMYL PEPTIDE RECEPTOR 2 FOR TREATING DERMATOLOGICAL DISEASES

RELATED APPLICATIONS

This application claims priority to U.S. patent application Ser. No. 14/196,155, filed on Mar. 4, 2014, which claims the benefit of U.S. Provisional Patent Application Ser. No. 61/773,778 filed Mar. 6, 2013, the disclosure of each of which is hereby incorporated by reference in its entirety.

BACKGROUND OF THE INVENTION

Field of the Invention

The present invention relates to a method for treating dermal inflammation and dermal diseases by local or systemic delivery, in a subject in need of such treatment, which comprises administering a pharmaceutical composition comprising a therapeutically effective amount of at least one agonist of Formyl peptide receptor 2 (FPR2).

Summary of the Related Art

The formyl peptide receptor (FPR) family belongs to the seven transmembrane domain G-protein-coupled receptor (GPCR) family. This family includes 3 members in humans and one member of this family FPR2 (also known as FPRL-1, ALXA4) is expressed predominantly on inflammatory cells such as monocytes and neutrophils, as well as on T cells and has been shown to play a critical role in leukocyte trafficking during inflammation and human pathology (Chiang N, Serhan C N, Dahlen, S, Drazen J M, Hay D W P, Rovati E, Shimizu T, Yokomizo T, Brink, C. The lipoxin receptor ALX: Potent ligand-specific and stereoselective actions in vivo. *Pharmacological Reviews* 2006; 58: 463-519). FPR2 is an exceptionally promiscuous receptor that responds to a menagerie of structurally diverse exogenous and endogenous ligands, including serum amyloid A (SAA), chemokine variant sCKβ8-1, the neuroprotective peptide humanin, anti-inflammatory eicosanoid lipoxin A4 (LXA4) and glucocorticoid-modulated protein annexin A1 (Chiang N, Serhan C N, Dahlen, S, Drazen J M, Hay D W P, Rovati E, Shimizu T, Yokomizo T, Brink, C. The lipoxin receptor ALX: Potent ligand-specific and stereoselective actions in vivo. *Pharmacological Reviews* 2006; 58: 463-519). FPR2 has been shown to transduce anti-inflammatory effects of arachidonic acid derived Lipoxin A4 (LXA4) in many systems, and has been shown to play a key role in the resolution of inflammation (Dufton N, Perretti M. Therapeutic anti-inflammatory potential of formyl peptide receptor agonists. *Pharmacology & Therapeutics* 2010; 127: 175-188). FPR2 knockout mice show exaggerated inflammation in disease conditions as expected by the biological role of the receptor (Dufton N, Hannon R, Brancaleone V, Dalli J, Patel H B, Gray M, D'Aquisto F, Buckingham J C, Perretti M, Flower R J. Anti-inflammatory role of the murine formyl-peptide receptor 2: Ligand-specific effects on leukocyte responses and experimental inflammation. *Journal of Immunology* 2010; 184: 2611-2619. Gavins F N E, Hughes E L, Buss N A P S, Holloway P M, Getting S J, Buckingham J C. Leukocyte recruitment in the brain in sepsis: involvement of the annexinl FPR2/ALX anti-inflammatory system. *FASEB* 2012; 26: 1-13).

Activation of FPR2 by lipoxin A4 or its analogs and by Annexin I protein has been shown to result in anti-inflammatory activity by promoting active resolution of inflammation which involves inhibition of polymorphonuclear neutrophils (PMNs) and eosinophils migration and also stimulate monocyte migration enabling clearance of apoptotic cells from the site of inflammation in a nonphlogistic manner (Gavins F N E, Hughes E L, Buss N A P S, Holloway P M, Getting S J, Buckingham J C. Leukocyte recruitment in the brain in sepsis: involvement of the annexinl FPR2/ALX anti-inflammatory system. *FASEB* 2012; 26: 1-13, Maderna P, Cottell D C, Toivonen T, Dufton N, Dalli J, Perretti M, Godson C. FPR2/ALX receptor expression and internalization are critical for lipoxin A4 and annexin-derived peptide-stimulated phagocytosis. *FASEB* 2010; 24: 4240-4249). In addition, FPR2 has been shown to inhibit natural killer (NK) cytotoxicity and promote activation of T cells which further contributes to down regulation of tissue damaging inflammatory signals. FPR2 interaction with LXA4 and Annexin has been shown to be beneficial in experimental models of dermal inflammation, angiogenesis, epithelial migration, edema, alopecia and corneal wound healing. (Reville K, Cream J K, Vivers S, Dransfield I, Godson C. Lipoxin A4 redistributes Myosin IIA and Cdc42 in macrophages: Implications for phagocytosis of apoptotic leukocytes. *Journal of Immunology* 2006; 176: 1878-1888; Serhan C. Resolution phase of inflammation: Novel endogenous anti-inflammatory and proresolving lipid mediators and pathways. *Annual reviews of Immunology* 2007; 25: 101-137; Takano T, Fiore S, Maddox J F, Brady H R, Petasis N A, Serhan C N. Aspirin-triggered 15-epi-lipoxin A4 and LXA4 stable analogues are potent inhibitors of acute inflammation: evidence for anti-inflammatory receptors. *Journal of Experimental Medicine* 1997; 185: 1693-1704; Leoni G, Alam A, Neumann P A, Lambeth J D, Cheng G, McCoy J, Hilgarth R S, Kundu K, Murthy N, Kusters D, Reutelingsperger C, Perretti M, Parkos C A, Neish A S, Nusrat A. Annexin A1, formyl peptide receptor, and NOX1 orchestrate epithelial repair. *Journal of Clinical Investigation*. 2013; 123:443-54; Leedom A, Sullivan A B, Dong B, Lau D, Gronert K. Endogenous LXA4 circuits are determinants of pathological angiogenesis in response to chronic injury. *American Journal of Pathology* 2010; 176: 74-84; Tsuruki T, Takahata K, Yoshikawa M. Mechanism of the protective effect of intraperitoneally administered agonists for formyl peptide receptors against chemotherapy-induced alopecia. Biosci *Biotechnology Biochemistry*. 2007; 71:1198-202).

Targeting FPR2 selectively would also have benefits in skin wound healing given its potent anti-inflammatory and pro-epithelial repair role. In addition, some skin diseases have been shown to have an abnormal expression of LL37, a pro-inflammatory cathelicidin which has been shown to be a natural ligand of FPR2. In the chronic inflammatory disease Rosacea, LL37 is highly expressed and is believed to play a key role in the pathogenesis (Yamasaki K, Di Nardo A, Bardan A, Murakami M, Ohtake T, Coda A, Dorschner R A, Bonnart C, Descargues P, Hovnanian A, Morhenn V B, Gallo R L. Increased serine protease activity and cathelicidin promotes skin inflammation in rosacea. *Nature Medicine*. 2007; 13:975-80).

BRIEF DESCRIPTION OF THE INVENTION

The present invention relates to a method for treating dermal inflammation and dermal diseases by local or systemic delivery, in a subject in need of such treatment, which comprises administering a pharmaceutical composition comprising a therapeutically effective amount of at least one agonist of Formyl peptide receptor 2 (FPR2).

Given the anti-inflammatory axis of LXA4-FPR2 we propose that FPR2 agonists will be useful in inhibiting LL-37-mediated inflammatory diseases such as Rosacea. Pharmaceutical utility of lipoxin A4 and its analogs are hampered by inherent physicochemical properties of the natural poly-olefinic natural product. Therefore, small molecule anti-inflammatory agonists of FPR2 would have a wide variety of therapeutic benefit in inflammatory disorders especially in the skin. FPR2 is widely expressed in human skin and its appendages. FPR2 thus represents an important novel pro-resolutionary molecular target for the development of new therapeutic agents in dermatological diseases with excessive inflammatory responses.

The invention pertains to the ability of FPR2 agonists to exhibit dermal anti-inflammatory activity with chemical stability and suitable for topical dermal delivery. These FPR2 compounds show good potency at the receptor and, importantly, the FPR2 compounds are topically active, and therefore could be administered in many forms, including but not limited to creams, lotions, gels, solutions, sprays, and foams. These compounds may also be administered IV, intramuscularly, intrathecally, subcutaneously, orally or intraperitoneally. These compounds will be useful for the treatment of dermatological diseases including, but not limited to, rosacea, rosacea fulminans, sunburn, psoriasis, menopause-associated hot flashes, flushing and redness associated with hot flashes, erythema associated with hot flashes, hot flashes resulting from orchiectomyatopic dermatitis, treatment of redness and itch from insect bites, photoaging, seborrheic dermatitis, acne, allergic dermatitis, telangiectasia (dilations of previously existing small blood vessels) of the face, angioectasias, rhinophyma (hypertrophy of the nose with follicular dilation), acne-like skin eruptions (may ooze or crust), burning or stinging sensation, erythema of the skin, cutaneous hyperactivity with dilation of blood vessels of the skin, Lyell's syndrome, Stevens-Johnson syndrome, local itching and discomfort associated with hemorrhoids, hemorrhoids, erythema multiforme minor, erythema multiforme major, erythema nodosum, eye puffiness, urticaria, pruritus, purpura, varicose veins, contact dermatitis, atopic dermatitis, nummular dermatitis, generalized exfoliative dermatitis, stasis dermatitis, lichen simplex chronicus, perioral dermatitis, pseudofolliculitis barbae, granuloma annulare, actinic keratosis, basal cell carcinoma, squamous cell carcinoma, eczema, dermal wound healing, hypertrophic scars, keloids, burns, rosacea, atopic dermatitis, acne, psoriasis, seborrheic dermatitis, actinic keratoses, basal cell carcinoma, squamous cell carcinoma, melanoma, viral warts, photoaging, photodamage, melasma, post-inflammatory hyperpigmentation, other disorders of pigmentation, and alopecia (scarring and non-scarring forms). The compounds below would be expected to have therapeutic effects in many different types of skin disease, but have been exemplified by demonstrating accelerated wound healing activity in a mouse dermal wound healing model (FIG. 1), and reduction of LL-37-induced inflammation in mice (FIG. 2) and human keratinocytes (FIG. 2). Anti-inflammatory activity in the LL-37-induced rosacea mouse model has been exemplified with three FPR2 agonists: {[(2S)-2-{[(4-bromo-2-fluorophenyl)carbamoyl]amino}-4-methylpentanoyl]amino}acetic acid, {[(2S,3S)-2-{[(4-bromophenyl)carbamoyl]amino}-3-methylpentanoyl]amino}acetic acid, {[(2S)-2-{[(4-bromophenyl)carbamoyl]amino}-4-methylpentanoyl]amino}acetic acid. Skin penetration of FPR2 agonists following topical administration has also been demonstrated (FIG. 3).

BRIEF DESCRIPTION OF THE DRAWINGS

FIG. 3. Absorption of FPR2 agonists in an in vitro human skin penetration model.

DETAILED DESCRIPTION OF THE INVENTION

Figure 1:
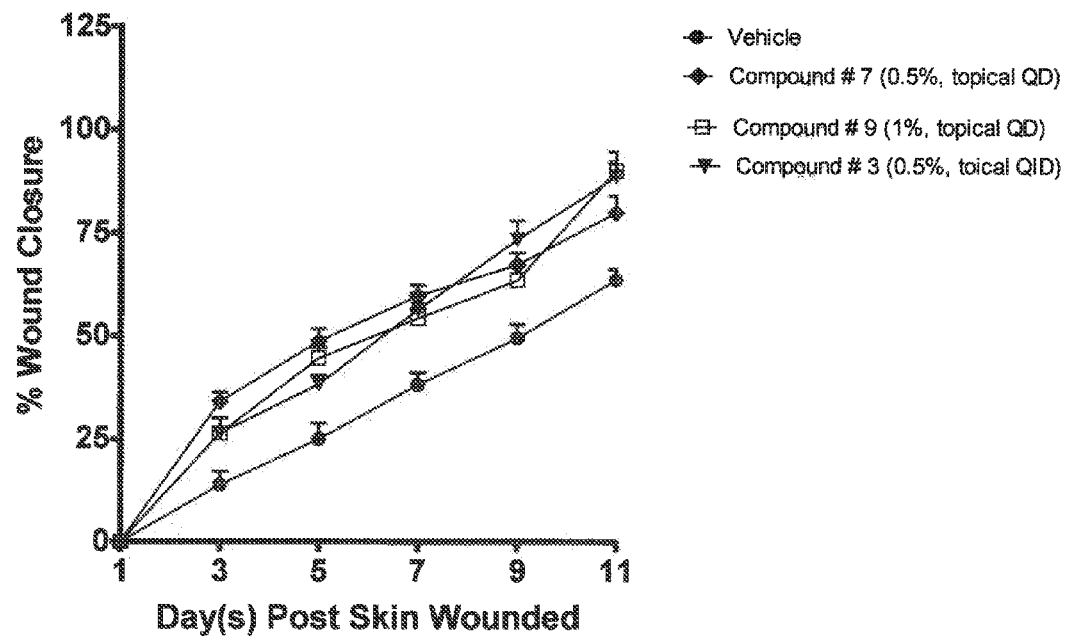
FIG. 1 FPR2 agonists show potent wound healing in a mouse model of punch dermal wound.

The present invention relates to a method for treating dermatological inflammation and dermatological diseases in a subject in need of such treatment, which comprises administering a pharmaceutical composition comprising a therapeutically effective amount of at least one agonist of Formyl peptide receptor 2 (FPR2).

In another aspect, the invention provides the use of at least one agonist of FPR2 for the manufacture of a medicament for the treatment of a dermatological inflammation disease or condition mediated by FPR2 in a mammal.

In another aspect, the invention provides a method for treating dermatological inflammatory diseases, which comprises administering a pharmaceutical composition comprising a therapeutically effective amount of at least one agonist of FPR2 as disclosed in U.S. patent application Ser. No. 13/668,835, provided that the compounds have binding activity at the FPR2 receptor.

In another aspect, the invention provides the use of at least one compound as disclosed in U.S. patent application Ser. No. 13/668,835 for the manufacture of a medicament for the treatment of a dermatological disease or condition mediated by FPR2 in a mammal, provided that the compounds have binding activity at the FPR2 receptor.

In another aspect, the invention provides the use of at least one compound as disclosed in U.S. patent application Ser. No. 13/668,835 for treating a dermatological disease or condition mediated by FPR2 in a mammal, provided that the compounds have binding activity at the FPR2 receptor.

The compounds disclosed in U.S. patent application Ser. No. 13/668,835 are represented by Formula I:

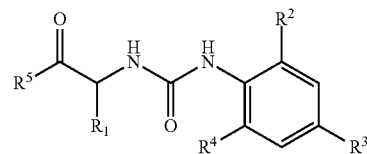

Formula I wherein:
$R^1$ is sec-butyl, $C_{6-10}$ aryl, —$CH_2$—($C_{6-10}$)aryl, —$CH_2$-heterocycle, $C_{4-8}$ cycloalkyl or $C_{3-8}$ cycloalkenyl or heterocycle;
$R^2$ is halogen or methyl;
$R^3$ is halogen;
$R^4$ is H, methyl or halogen;
$R^5$ is $OR^6$ or $NH_2$; and
$R^6$ is H or $C_{2-4}$ alkyl.

In another aspect, the invention provides a method for treating dermatological inflammatory diseases, which comprises administering a pharmaceutical composition, comprising a therapeutically effective amount of at least one agonist of FPR2 as disclosed in U.S. patent application Ser.

No. 13/523,579, provided that the compounds have binding activity at the FPR2 receptor.

In another aspect, the invention provides the use of at least one compound as disclosed in U.S. patent application Ser. No. 13/523,579 for the manufacture of a medicament for the treatment of a dermatological disease or condition mediated by FPR2 in a mammal, provided that the compounds have binding activity at the FPR2 receptor.

In another aspect, the invention provides the use of at least one compound as disclosed in U.S. patent application Ser. No. 13/523,579 for treating a dermatological disease or condition mediated by FPR2 in a mammal, provided that the compounds have binding activity at the FPR2 receptor.

The compounds disclosed in U.S. patent application Ser. No. 13/523,579 are represented by Formula II:

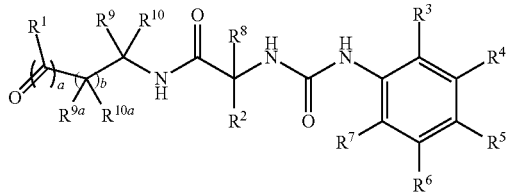

Formula II wherein:
a is 1 and b is 0;
a is 0 and b is 1;
a is 1 and b is 1;
$R^1$ is optionally substituted $C_{1-8}$ alkyl, optionally substituted $C_{3-8}$ cycloalkyl, optionally substituted heterocycle, optionally substituted $C_{3-8}$ cycloalkyl, optionally substituted $C_{6-10}$ aryl, optionally substituted $C_{3-8}$ cycloalkenyl, —$NR^{11}R^{12}$ or —$OR^{13}$;
$R^2$ is optionally substituted $C_{1-8}$ alkyl or optionally substituted $C_{6-10}$ aryl;
$R^3$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;
$R^4$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;
$R^5$ is halogen, —$CF_3$ or —$S(O)_nR^{14}$;
n is 0, 1 or 2;
$R^6$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;
$R^7$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;
$R^8$ is hydrogen, optionally substituted $C_{1-8}$ alkyl or optionally substituted $C_{6-10}$ aryl;
$R^9$ is hydrogen, optionally substituted $C_{1-8}$ alkyl or optionally substituted $C_{6-10}$ aryl;
$R^{10}$ is hydrogen, optionally substituted $C_{1-8}$ alkyl or optionally substituted $C_{6-10}$ aryl;
$R^{9a}$ is hydrogen, optionally substituted $C_{1-8}$ alkyl or optionally substituted $C_{6-10}$ aryl;
$R^{10a}$ is hydrogen, optionally substituted $C_{1-8}$ alkyl or optionally substituted $C_{6-10}$ aryl;
$R^{11}$ is hydrogen or optionally substituted $C_{1-8}$ alkyl;
$R^{12}$ is hydrogen or optionally substituted $C_{1-8}$ alkyl;
$R^{13}$ is hydrogen or optionally substituted $C_{1-8}$ alkyl;
$R^{14}$ is hydrogen, $CF_3$ or optionally substituted $C_{1-8}$ alkyl; and
$R^{15}$ is hydrogen or optionally substituted $C_{1-8}$ alkyl.

In another aspect, the invention provides a method for treating dermatological inflammatory diseases, which comprises administering a pharmaceutical composition, comprising a therapeutically effective amount of at least one agonist of FPR2 as disclosed in U.S. patent application Ser. No. 13/673,800, provided that the compounds have binding activity at the FPR2 receptor.

In another aspect, the invention provides the use of at least a compound as disclosed in U.S. patent application Ser. No. 13/673,800 for the manufacture of a medicament for the treatment of a dermatological disease or condition mediated by FPR2 in a mammal, provided that the compounds have binding activity at the FPR2 receptor.

In another aspect, the invention provides the use of at least a compound as disclosed in U.S. patent application Ser. No. 13/673,800 for treating a dermatological disease or condition mediated by FPR2 in a mammal, provided that the compounds have binding activity at the FPR2 receptor.

The compounds disclosed in U.S. patent application Ser. No. 13/673,800 are represented by Formula III:

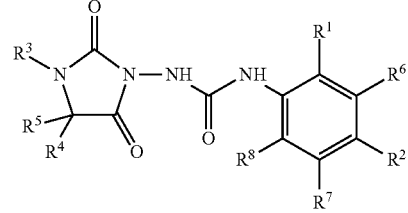

Formula III wherein:
$R^1$ is halogen, hydrogen, optionally substituted $C_{1-8}$ alkyl, $OR^9$, $C(O)R^{10}$, $NO_2$, $NR^{13}R^{14}$, CN, $SR^{15}$ or $SO_2R^{16}$;
$R^2$ is halogen, optionally substituted $C_{1-8}$ alkyl, $CF_3$, $OR^9$, $C(O)R^{10}$, $NO_2$, $NR^{13}R^{14}$, CN, $SR^{15}$ or $SO_2R^{16}$;
$R^3$ is hydrogen, optionally substituted $C_{1-8}$ alkyl, optionally substituted $C_{3-8}$ cycloalkyl, optionally substituted $C_{3-8}$ cycloalkenyl, optionally substituted $C_{6-10}$ aryl, optionally substituted heterocycle, or together with $R^5$ forms a 10- or 11-membered polycyclic ring which is optionally substituted;
$R^4$ is hydrogen, optionally substituted $C_{1-8}$ alkyl,

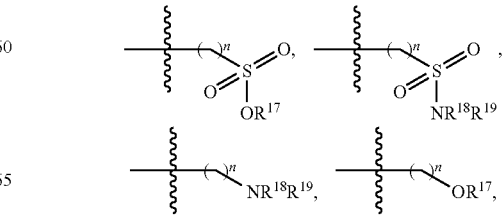

-continued

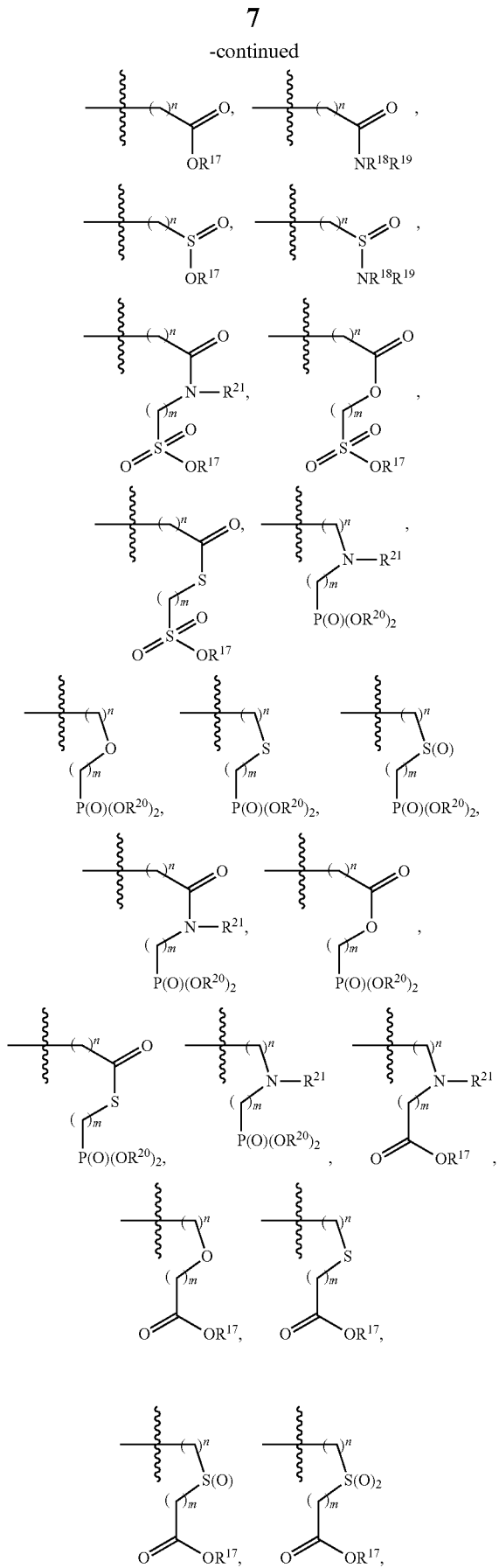

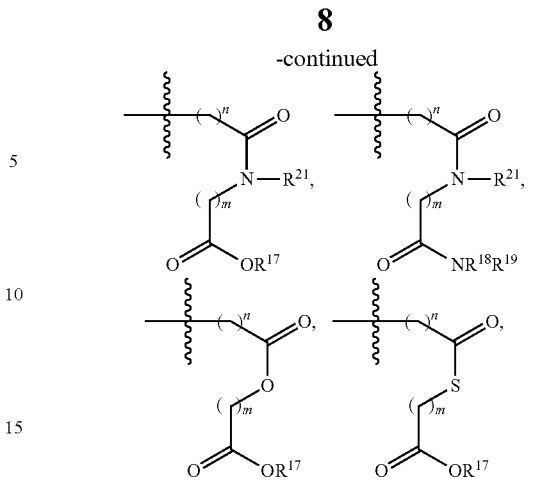

optionally substituted $C_{3-8}$ cycloalkyl, optionally substituted $C_{3-8}$ cycloalkenyl, optionally substituted $C_{6-10}$ aryl, optionally substituted heterocycle, or together with $R^5$ forms a spiro monocyclic or polycyclic, carbocyclic or heterocyclic, saturated or unsaturated 5 to 10 member ring which is optionally substituted;

$R^5$ is hydrogen, optionally substituted $C_{1-8}$ alkyl, optionally substituted $C_{3-8}$ cycloalkyl, optionally substituted $C_{3-6}$ cycloalkenyl, optionally substituted $C_{6-10}$ aryl, optionally substituted heterocycle, or together with $R^4$ forms a spiro monocyclic or polycyclic, carbocyclic or heterocyclic, saturated or unsaturated 5 to 10 member ring which is optionally substituted or together with $R^3$ forms a 5 or 6 member ring which is optionally substituted;

$R^6$ is halogen, hydrogen, optionally substituted $C_{1-8}$ alkyl, $OR^9$, $C(O)R^{10}$, $NO_2$, $NR^{13}R^{14}$, $CN$, $SR^{15}$ or $SO_2R^{16}$;

$R^7$ is halogen, hydrogen, optionally substituted $C_{1-8}$ alkyl, $OR^9$, $C(O)R^{10}$, $NO_2$, $NR^{13}R^{14}$, $CN$, $SR^{15}$ or $SO_2R^{16}$;

$R^8$ is halogen, hydrogen, optionally substituted $C_{1-8}$ alkyl, $OR^9$, $C(O)R^{10}$, $NO_2$, $NR^{13}R^{14}$, $CN$, $SR^{15}$ or $SO_2R^{16}$;

$R^9$ is hydrogen, $C(O)(C_{1-8}$ alkyl) or optionally substituted $C_{1-8}$ alkyl;

$R^{10}$ is hydrogen, optionally substituted $C_{1-8}$ alkyl, $O(C_{1-8}$ alkyl), $NR^{11}R^{12}$ or $OH$;

$R^{11}$ is hydrogen, optionally substituted $C_{6-10}$ aryl or optionally substituted $C_{1-8}$ alkyl;

$R^{12}$ is hydrogen, optionally substituted $C_{6-10}$ aryl or optionally substituted $C_{1-8}$ alkyl;

$R^{13}$ is hydrogen, optionally substituted $C_{6-10}$ aryl or optionally substituted $C_{1-8}$ alkyl;

$R^{14}$ is hydrogen, optionally substituted $C_{6-10}$ aryl, optionally substituted $C_{1-8}$ alkyl, $C(O)(C_{1-8}$ alkyl) or $SO_2(C_{1-8}$ alkyl);

$R^{15}$ is hydrogen, optionally substituted $C_{1-8}$ alkyl or $O(C_{1-8}$ alkyl);

$R^{16}$ is $OH$, $O(C_{1-8}$ alkyl), $(C_{1-8}$ alkyl) or $NR^{11}R^{12}$;

$R^{17}$ is hydrogen, optionally substituted $C_{6-10}$ aryl or optionally substituted $C_{1-8}$ alkyl;

$R^{18}$ is hydrogen, $C(O)(C_{1-8}$ alkyl), optionally substituted $C_{6-10}$ aryl, or optionally substituted $C_{1-8}$ alkyl;

$R^{19}$ is hydrogen, $C(O)(C_{1-8}$ alkyl), optionally substituted $C_{6-10}$ aryl or optionally substituted $C_{1-8}$ alkyl;

$R^{20}$ is hydrogen, optionally substituted $C_{6-10}$ aryl or optionally substituted $C_{1-8}$ alkyl;

$R^{21}$ is hydrogen, optionally substituted $C_{6-10}$ aryl or optionally substituted $C_{1-8}$ alkyl;

n is 1, 2, 3, 4, or 5; and m is 1, 2, 3, 4, or 5.

In another aspect, the invention provides a method for treating dermatological inflammatory diseases, which comprises administering a pharmaceutical composition comprising a therapeutically effective amount of at least one agonist of FPR2 as disclosed in U.S. patent application Ser. No. 13/765,527, provided that the compounds have binding activity at the FPR2 receptor.

In another aspect, the invention provides the use of at least one compound as disclosed in U.S. patent application Ser. No. 13/765,527 for the manufacture of a medicament for the treatment of a dermatological disease or condition mediated by FPR2 in a mammal, provided that the compounds have binding activity at the FPR2 receptor.

In another aspect, the invention provides the use of at least one compound as disclosed in U.S. patent application Ser. No. 13/765,527 for treating a dermatological disease or condition mediated by FPR2 in a mammal, provided that the compounds have binding activity at the FPR2 receptor.

The compounds disclosed in U.S. patent application Ser. No. 13/765,527 are represented by Formula IV:

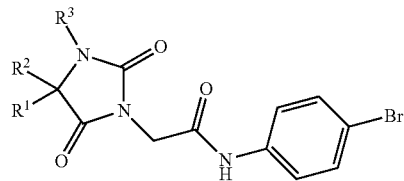

Formula IV wherein:
$R^1$ is hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, substituted or unsubstituted $C_{3-8}$ cycloalkenyl, substituted or unsubstituted heterocycle or substituted or unsubstituted $C_{6-10}$ aryl, or together with $R^2$ can form an optionally substituted cyclobutyl;
$R^2$ is isopropyl or together with $R^3$ can form a substituted or unsubstituted 3 to 6 member ring heterocycle or together with $R^1$ can form an optionally substituted cyclobutyl, cyclopropyl; and
$R^3$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, substituted or unsubstituted $C_{3-8}$ cycloalkenyl, substituted or unsubstituted heterocycle, substituted or unsubstituted $C_{6-10}$ aryl or together with $R^2$ can form a substituted or unsubstituted 3 to 6 member ring heterocycle.

In another aspect, the invention provides a method for treating dermatological inflammatory diseases, which comprises administering a therapeutically effective amount of a pharmaceutical composition, comprising at least one agonist of FPR2 as disclosed in U.S. patent application Ser. No. 13/409,228, provided that the compounds have binding activity at the FPR2 receptor.

In another aspect, the invention provides the use of at least one compound as disclosed in U.S. patent application Ser. No. 13/409,228 for the manufacture of a medicament for the treatment of a dermatological disease or condition mediated by FPR2 in a mammal, provided that the compounds have binding activity at the FPR2 receptor.

In another aspect, the invention provides the use of at least one compound as disclosed in U.S. patent application Ser. No. 13/409,228 for treating a dermatological disease or condition mediated by FPR2 in a mammal, provided that the compounds have binding activity at the FPR2 receptor.

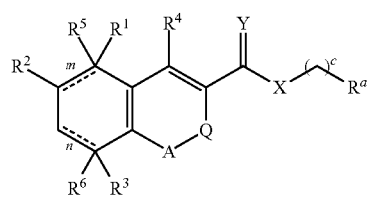

Formula V wherein:
$\underset{\text{m}}{\text{─────}}$ is a single bond or a double bond;
$\underset{\text{n}}{\text{─────}}$ is a single bond or a double bond;
$R^1$ is H, halogen, —S(O)$R^{10}$, —S(O)$_2R^{11}$, nitro, cyano, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, NR$^{13}$R$^{14}$, $C_{3-8}$ cycloalkyl, $C_{3-8}$ cycloalkenyl or hydroxyl;
$R^2$ is H, halogen, —S(O)$R^{10}$, —S(O)$_2R^{11}$, nitro, cyano, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, NR$^{13}$R$^{14}$, $C_{3-8}$ cycloalkyl, $C_{3-8}$ cycloalkenyl or hydroxyl;
$R^3$ is H, halogen, —S(O)$R^{10}$, —S(O)$_2R^{11}$, nitro, cyano, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, NR$^{13}$R$^{14}$, $C_{3-8}$ cycloalkyl, $C_{3-8}$ cycloalkenyl, $C_{6-10}$ aryl or hydroxyl;
$R^4$ is H or C(O)$R^{12}$;
$R^5$ is H, —O$C_{1-6}$ alkyl, —S$C_{1-6}$ alkyl, —$C_{1-6}$ alkyl, —$C_{2-6}$ alkenyl or —$C_{2-6}$ alkynyl;
$R^6$ is H, —O$C_{1-6}$ alkyl, —S$C_{1-6}$ alkyl, —$C_{1-6}$ alkyl, —$C_{2-6}$ alkenyl or —$C_{2-6}$ alkynyl;
Y is O or S;
X is O, NR, or CH$_2$;
$R^a$ is $C_{6-10}$ aryl,

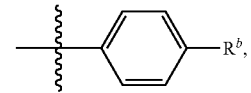

heteroaryl, $C_{3-8}$ cycloalkyl, $C_{3-8}$ cycloalkenyl or H;
$R^b$ is halogen;
c is 0, 1 or 2;

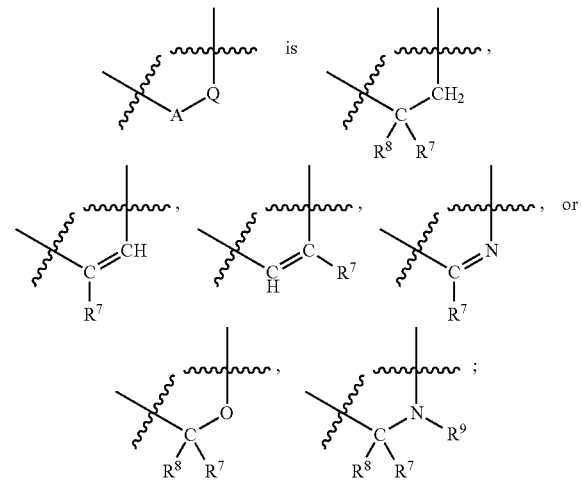

$R^7$ is H, halogen, —S(O)$R^{10}$, —S(O)$_2R^{11}$, nitro, hydroxyl, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, N$R^{13}R^{14}$, C$_{3-8}$ cycloalkenyl or C$_{3-8}$ cycloalkyl;

$R^8$ is H, halogen, —S(O)$R^{10}$, —S(O)$_2R^{11}$, cyano, —OC$_{1-6}$ alkyl, —SC$_{1-6}$ alkyl, —C$_{1-6}$ alkyl, C$_{2-6}$ alkenyl, —C$_{2-6}$ alkynyl, C(O)$R^{12}$, N$R^{13}R^{14}$, C$_{3-8}$ cycloalkenyl or C$_{3-8}$ cycloalkyl;

$R^9$ is H, —S(O)$_2R^{11}$, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, C$_{3-8}$ cycloalkenyl or C$_{3-8}$ cycloalkyl;

$R^{10}$ is —C$_{1-6}$ alkyl, C$_{3-8}$ cycloalkyl, or C$_{3-8}$ cycloalkenyl;

$R^{11}$ is H, hydroxyl, —C$_{1-6}$ alkyl, C$_{3-8}$ cycloalkyl or C$_{3-8}$ cycloalkenyl;

$R^{12}$ is H, hydroxyl, —C$_{1-6}$ alkyl, C$_{3-8}$ cycloalkyl, C$_{3-8}$ cycloalkenyl, N$R^{13}R^{14}$ or —OC$_{1-6}$ alkyl;

$R^{13}$ is H, —C$_{1-6}$ alkyl, C$_{3-8}$ cycloalkyl, C$_{3-8}$ cycloalkenyl, SO$_2R^{11}$ or C(O)$R^{15}$;

$R^{14}$ is H, —C$_{1-6}$ alkyl, C$_{3-8}$ cycloalkenyl, aryl, heterocycle or C$_{3-8}$ cycloalkyl;

$R^{15}$ is H, —C$_{1-6}$ alkyl, C$_{3-8}$ cycloalkenyl or C$_{3-8}$ cycloalkyl; and R is H, —C$_{1-6}$ alkyl, C$_{3-8}$ cycloalkenyl or C$_{3-8}$ cycloalkyl; with the proviso:

when ------ is a double bond then $R^5$ and $R^6$ are void.

In another aspect, the invention provides a method for treating dermatological inflammatory diseases, which comprises administering a pharmaceutical composition, comprising a therapeutically effective amount of at least one agonist of FPR2 as disclosed in U.S. patent application Ser. No. 13/370,472, provided that the compounds have binding activity at the FPR2 receptor.

In another aspect, the invention provides the use of at least one compound as disclosed in U.S. patent application Ser. No. 13/370,472 for the manufacture of a medicament for the treatment of a dermatological disease or condition mediated by FPR2 in a mammal, provided that the compounds have binding activity at the FPR2 receptor.

In another aspect, the invention provides the use of at least one compound as disclosed in U.S. patent application Ser. No. 13/370,472 for treating a dermatological disease or condition mediated by FPR2 in a mammal, provided that the compounds have binding activity at the FPR2 receptor.

The compounds as disclosed in U.S. patent application Ser. No. 13/370,472 are represented by Formula VI:

Formula VI wherein:

A is C$_{6-10}$ aryl, heterocycle, C$_{3-8}$ cycloalkyl or C$_{3-8}$ cycloalkenyl;

$R^{17}$ is C$_{1-6}$ alkyl or

B is C$_{6-10}$ aryl, heterocycle, C$_{3-8}$ cycloalkyl or C$_{3-8}$ cycloalkenyl;

$R^1$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, N$R^{13}R^{14}$, C$_{3-8}$ cycloalkyl or hydroxyl;

$R^2$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, N$R^{13}R^{14}$, C$_{3-8}$ cycloalkyl or hydroxyl;

$R^3$ is H, C$_{1-6}$ alkyl or C$_{3-8}$ cycloalkyl;

$R^4$ is H, C$_{1-6}$ alkyl or C$_{3-8}$ cycloalkyl;

$R^{5a}$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, N$R^{13}R^{14}$, C$_{3-8}$ cycloalkyl or hydroxyl;

$R^{5b}$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, N$R^{13}R^{14}$, C$_{3-8}$ cycloalkyl or hydroxyl;

$R^{5c}$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, N$R^{13}R^{14}$, C$_{3-8}$ cycloalkyl or hydroxyl;

$R^{5d}$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, N$R^{13}R^{14}$, C$_{3-8}$ cycloalkyl or hydroxyl;

$R^6$ is H, —S(O)$_2R^{11}$, —C$_{1-6}$ alkyl, —(CH$_2$)$_n$N$R^{13}R^{14}$, —(CH$_2$)$_m$ heterocycle, C(O)$R^{12}$N$R^{13}R^{14}$, C$_{3-8}$ cycloalkyl, C$_{6-10}$ aryl, or heterocycle;

$R^7$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, N$R^{13}R^{14}$, C$_{3-8}$ cycloalkyl or hydroxyl;

$R^8$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, N$R^{13}R^{14}$, C$_{3-8}$ cycloalkyl or hydroxyl;

$R^9$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, N$R^{13}R^{14}$, C$_{3-8}$ cycloalkyl or hydroxyl;

$R^{10}$ is H, halogen, —S(O)$R^{15}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, N$R^{13}R^{14}$, C$_{3-8}$ cycloalkyl or hydroxyl;

X is O or S;

Y is O or S;

$R^{11}$ is H, hydroxyl, —C$_{1-6}$ alkyl, C$_{3-8}$ cycloalkyl or N$R^{13}R^{14}$;

$R^{12}$ is H, hydroxyl, —C$_{1-6}$ alkyl, hydroxyl, C$_{3-8}$ cycloalkyl, N$R^{13}R^{14}$ or —OC$_{1-6}$ alkyl;

$R^{13}$ is H, —C$_{1-6}$ alkyl, C$_{3-8}$ cycloalkyl, SO$_2R^{11}$ or C(O)$R^{16}$;

$R^{14}$ is H, —C$_{1-6}$ alkyl or C$_{3-8}$ cycloalkyl;

$R^{15}$ is —C$_{1-6}$ alkyl, or C$_{3-8}$ cycloalkyl;

$R^{16}$ is H, —C$_{1-6}$ alkyl or C$_{3-8}$ cycloalkyl;

n is 1-4; and m is 1-4.

In another aspect, the invention provides a method for treating dermatological inflammatory diseases, which comprises administering a pharmaceutical composition, comprising a therapeutically effective amount of at least one agonist of FPR2 as disclosed in U.S. patent application Ser. No. 13/863,934, provided that the compounds have binding activity at the FPR2 receptor.

In another aspect, the invention provides the use of at least one compound as disclosed in U.S. patent application Ser. No. 13/863,934 for the manufacture of a medicament for the treatment of a dermatological disease or condition mediated by FPR2 in a mammal, provided that the compounds have binding activity at the FPR2 receptor.

In another aspect, the invention provides the use of at least one compound as disclosed in U.S. patent application Ser. No. 13/863,934 for treating a dermatological disease or condition mediated by FPR2 in a mammal, provided that the compounds have binding activity at the FPR2 receptor.

The compounds as disclosed in U.S. patent application Ser. No. 13/863,934 are represented by Formula VII:

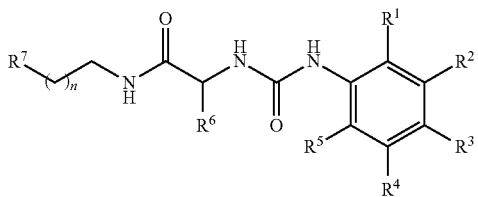

Formula VII wherein:

n is 0 or 1;

$R^1$ is hydrogen, substituted or unsubstituted $C_{1-8}$ alkyl, halogen, $-NR^8R^9$, $-NC(O)R^{20}$, $-OR^{10}$, $-OC(O)R^{21}$, $-SR^{11}$, $-C(O)R^{12}$, CN or $NO_2$;

$R^2$ is hydrogen, substituted or unsubstituted $C_{1-8}$ alkyl, halogen, $-NR^8R^9$, $-NC(O)R^{20}$, $-OR^{10}$, $-OC(O)R^{21}$, $-SR^{11}$, $-C(O)R^{12}$, CN or $NO_2$;

$R^3$ is hydrogen, substituted or unsubstituted $C_{1-8}$ alkyl, halogen, $-NR^8R^9$, $-NC(O)R^{20}$, $-OR^{10}$, $-OC(O)R^{21}$, $-SR^{11}$, $-C(O)R^{12}$, CN, $NO_2$, $CF_3$, $S(O)R^{15}$ or $S(O)_2R^{16}$;

$R^4$ is hydrogen, substituted or unsubstituted $C_{1-8}$ alkyl, halogen, $-NR^8R^9$, $-NC(O)R^{20}$, $-OR^{10}$, $-OC(O)R^{21}$, $-SR^{11}$, $-C(O)R^{12}$, CN or $NO_2$;

$R^5$ is hydrogen, substituted or unsubstituted $C_{1-8}$ alkyl, halogen, $-NR^8R^9$, $-NC(O)R^{20}$, $-OR^{10}$, $-OC(O)R^{21}$, $SR^{11}$, $-C(O)R^{12}$, CN or $NO_2$;

$R^6$ is hydrogen, substituted or unsubstituted $C_{1-8}$ alkyl, substituted or unsubstituted heterocycle, substituted or unsubstituted $C_{3-8}$ cycloalkyl, substituted or unsubstituted $C_{6-10}$ aryl, substituted or unsubstituted $C_{3-8}$ cycloalkenyl or $-CH_2R^{19}$;

$R^7$ is substituted or unsubstituted heterocycle, $-SR^{11}$, $-NR^8R^9$, $-N(H)C(O)N(H)S(O)_2R^{19}$, $-BR^{13}R^{14}$, $-S(O)R^{15}$, $-C(O)N(H)(CN)$, $-C(O)N(H)S(O)_2R^{19}$, $-S(O)(N)(PO_3H_2)$, $-S(O)_2R^{16}$ or $-P(O)R^{17}R^{18}$;

$R^8$ is hydrogen, substituted or unsubstituted $C_{1-8}$ alkyl, substituted or unsubstituted $C_{3-8}$ cycloalkyl, substituted or unsubstituted heterocycle, or substituted or unsubstituted $C_{6-10}$ aryl;

$R^9$ is hydrogen, substituted or unsubstituted $C_{1-8}$ alkyl, substituted or unsubstituted $C_{3-8}$ cycloalkyl, substituted or unsubstituted heterocycle, or substituted or unsubstituted $C_{6-10}$ aryl;

$R^{10}$ is hydrogen or substituted or unsubstituted $C_{1-8}$ alkyl;

$R^{11}$ is hydrogen, substituted or unsubstituted $C_{1-8}$ alkyl or $-CF_3$;

$R^{12}$ is hydrogen, substituted or unsubstituted $C_{1-8}$ alkyl, hydroxyl, $-OR^{24}$ or $-NR^8R^9$;

$R^{13}$ is $-OR^{22}$;

$R^{14}$ is $-OR^{23}$;

$R^{15}$ is substituted or unsubstituted $C_{1-8}$ alkyl;

$R^{16}$ is substituted or unsubstituted $C_{1-8}$ alkyl, $-NR^8R^9$, $-NHS(O)_2R^{19}$ or hydroxyl;

$R^{17}$ is $OR^{10}$ or $NR^8R^9$;

$R^{18}$ is $OR^{10}$ or $NR^8R^9$;

$R^{19}$ is substituted or unsubstituted heterocycle, substituted or unsubstituted $C_{3-8}$ cycloalkyl, substituted or unsubstituted $C_{6-10}$ aryl or substituted or unsubstituted $C_{3-8}$ cycloalkenyl;

$R^{20}$ is hydrogen, substituted or unsubstituted $C_{1-8}$ alkyl, substituted or unsubstituted $C_{3-8}$ cycloalkyl, substituted or unsubstituted heterocycle, or substituted or unsubstituted $C_{6-10}$ aryl;

$R^{21}$ is hydrogen, substituted or unsubstituted $C_{1-8}$ alkyl substituted or unsubstituted $C_{3-8}$ cycloalkyl, substituted or unsubstituted heterocycle, or substituted or unsubstituted $C_{6-10}$ aryl;

$R^{22}$ is hydrogen, substituted or unsubstituted $C_{1-8}$ alkyl, or together with $R^{23}$ can form a cycle;

$R^{23}$ is hydrogen, substituted or unsubstituted $C_{1-8}$ alkyl, or together with $R^{22}$ can form a cycle; and $R^{24}$ is hydrogen, substituted or unsubstituted $C_{1-8}$ alkyl, substituted or unsubstituted $C_{3-8}$ cycloalkyl, substituted or unsubstituted heterocycle, or substituted or unsubstituted $C_{6-10}$ aryl.

The term "alkyl", as used herein, refers to saturated, monovalent or divalent hydrocarbon moieties having linear or branched moieties or combinations thereof and containing 1 to 8 carbon atoms. One methylene ($-CH_2-$) group, of the alkyl group can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkyl groups can have one or more chiral centers. Alkyl groups can be independently substituted by halogen atoms, hydroxyl groups, cycloalkyl groups, amino groups, heterocyclic groups, aryl groups, carboxylic acid groups, phosphonic acid groups, sulphonic acid groups, phosphoric acid groups, nitro groups, amide groups, sulfonamide groups.

The term "cycloalkyl", as used herein, refers to a monovalent or divalent group of 3 to 8 carbon atoms derived from a saturated cyclic hydrocarbon. Cycloalkyl groups can be monocyclic or polycyclic. Cycloalkyl can be independently substituted by halogen atoms, sulfonyl $C_{1-8}$ alkyl groups, sulfoxide $C_{1-8}$ alkyl groups, sulfonamide groups, nitro groups, cyano groups, $-OC_{1-8}$ alkyl groups, $-SC_{1-8}$ alkyl groups, $-C_{1-8}$ alkyl groups, $-C_{2-6}$ alkenyl groups, $-C_{2-6}$ alkynyl groups, ketone groups, alkylamino groups, amino groups, aryl groups, $C_{3-8}$ cycloalkyl groups or hydroxyl groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. Cycloalkenyl groups can be independently substituted by halogen atoms, sulfonyl groups, sulfoxide groups, nitro groups, cyano groups, $-OC_{1-6}$ alkyl groups, $-SC_{1-6}$ alkyl groups, $-C_{1-6}$ alkyl groups, $-C_{2-6}$ alkenyl groups, $-C_{2-6}$ alkynyl groups, ketone groups, alkylamino groups, amino groups, aryl groups, $C_{3-8}$ cycloalkyl groups or hydroxyl groups.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. One methylene (—CH$_2$—) group, of the alkenyl can be replaced by oxygen, sulfur, sulfoxide, nitrogen, carbonyl, carboxyl, sulfonyl, sulfate, sulfonate, amide, sulfonamide, by a divalent C$_{3-8}$ cycloalkyl, by a divalent heterocycle, or by a divalent aryl group. C$_{2-6}$ alkenyl can be in the E or Z configuration. Alkenyl groups can be substituted by alkyl groups, as defined above or by halogen atoms.

The term "alkynyl", as used herein, refers to a monovalent or divalent hydrocarbon radical having 2 to 6 carbon atoms, derived from a saturated alkyl, having at least one triple bond. One methylene (—CH$_2$—) group, of the alkynyl can be replaced by oxygen, sulfur, sulfoxide, nitrogen, carbonyl, carboxyl, sulfonyl, sulfate, sulfonate, amide, sulfonamide, by a divalent C$_{3-8}$ cycloalkyl, by a divalent heterocycle, or by a divalent aryl group. Alkynyl groups can be substituted by alkyl groups, as defined above, or by halogen atoms.

The term "heterocycle" as used herein, refers to a 3 to 10 membered ring, which can be aromatic or non-aromatic, saturated or unsaturated, containing at least one heteroatom selected form oxygen, nitrogen, sulfur, or combinations of at least two thereof, interrupting the carbocyclic ring structure. The heterocyclic ring can be interrupted by a C=O; the S and N heteroatoms can be oxidized. Heterocycles can be monocyclic or polycyclic. Heterocyclic ring moieties can be substituted by halogen atoms, sulfonyl groups, sulfoxide groups, nitro groups, cyano groups, —OC$_{1-6}$ alkyl groups, —SC$_{1-6}$ alkyl groups, —C$_{1-8}$ alkyl groups, —C$_{2-6}$ alkenyl groups, —C$_{2-6}$ alkynyl groups, ketone groups, alkylamino groups, amino groups, aryl groups, C$_{3-8}$ cycloalkyl groups or hydroxyl groups.

The term "aryl" as used herein, refers to an organic moiety derived from an aromatic hydrocarbon consisting of a ring containing 6 to 10 carbon atoms, by removal of one hydrogen atom. Aryl can be substituted by halogen atoms, sulfonyl C$_{1-6}$ alkyl groups, sulfoxide C$_{1-6}$ alkyl groups, sulfonamide groups, carboxylic acid groups, C$_{1-6}$ alkyl carboxylates (ester) groups, amide groups, nitro groups, cyano groups, —OC$_{1-6}$ alkyl groups, —SC$_{1-6}$ alkyl groups, —C$_{1-6}$ alkyl groups, —C$_{2-6}$ alkenyl groups, —C$_{2-6}$ alkynyl groups, ketone groups, aldehydes, alkylamino groups, amino groups, aryl groups, C$_{3-8}$ cycloalkyl groups or hydroxyl groups. Aryls can be monocyclic or polycyclic.

The term "hydroxyl" as used herein, represents a group of formula "—OH".

The term "carbonyl" as used herein, represents a group of formula "—C(O)—".

The term "ketone" as used herein, represents an organic compound having a carbonyl group linked to a carbon atom such as —(CO)R$^x$, wherein R$^x$ can be alkyl, aryl, cycloalkyl, cycloalkenyl, heterocycle as defined above.

The term "amine" as used herein, represents a group of formula "—NR$^x$R$^y$", wherein R$^x$ and R$^y$ can be the same or independently H, alkyl, aryl, cycloalkyl, cycloalkenyl, heterocycle as defined above.

The term "carboxyl" as used herein, represents a group of formula "—C(O)O—".

The term "sulfonyl" as used herein, represents a group of formula "—SO$_2$—".

The term "sulfate" as used herein, represents a group of formula "—O—S(O)$_2$—O—".

The term "sulfonate" as used herein, represents a group of the formula "—S(O)$_2$—O—".

The term "carboxylic acid" as used herein, represents a group of formula "—C(O)OH".

The term "nitro" as used herein, represents a group of formula "—NO$_2$".

The term "cyano" as used herein, represents a group of formula "—CN".

The term "amide" as used herein, represents a group of formula "—C(O)NR$^x$R$^y$" wherein R$^x$ and R$^y$ can be the same or independently H, alkyl, aryl, cycloalkyl, cycloalkenyl, heterocycle as defined above.

The term "sulfonamide" as used herein, represents a group of formula "—S(O)$_2$NR$^x$R$^y$" wherein R$^x$ and R$^y$ can be the same or independently H, alkyl, aryl, cycloalkyl, cycloalkenyl, heterocycle as defined above.

The term "sulfoxide" as used herein, represents a group of formula "—S(O)—".

The term "phosphonic acid" as used herein, represents a group of formula "—P(O)(OH)$_2$".

The term "phosphoric acid" as used herein, represents a group of formula "—OP(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

In another aspect, agonists of FPR2 are compounds selected from Table 1:

TABLE 1

| Structure | IUPAC name | FPRL-1 Ga16-CHO EC$_{50}$ (efficacy) |
|---|---|---|
| 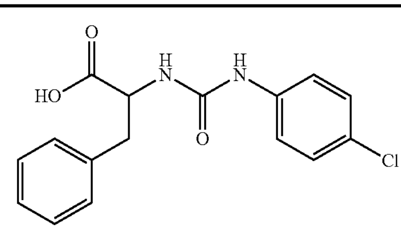 | 2-({[(4-chlorophenyl)amino]carbonyl}amino)-3-phenylpropanoic acid | 110 nM (1.0) |

TABLE 1-continued

| Structure | IUPAC name | FPRL-1 Gα16-CHO EC$_{50}$ (efficacy) |
|---|---|---|
| 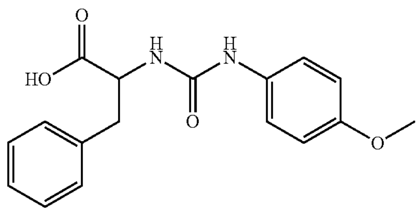 [SMILES: COc1ccc(NC(=O)NC(Cc2ccccc2)C(=O)O)cc1] | (2S)-2-({[(4-methoxyphenyl)amino]carbonyl}amino)-3-phenylpropanoic acid | 1754 nM (0.90) |
| 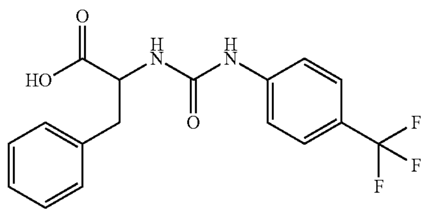 [SMILES: O=C(Nc1ccc(C(F)(F)F)cc1)NC(Cc1ccccc1)C(=O)O] | (2S)-3-phenyl-2-[({[4-(trifluoromethyl)phenyl]amino}carbonyl)amino]propanoic acid | 120 nM (0.97) |
| 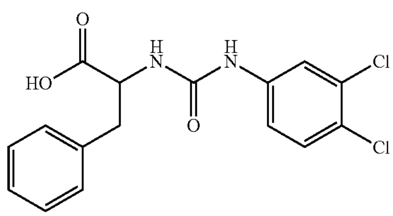 [SMILES: O=C(Nc1ccc(Cl)c(Cl)c1)NC(Cc1ccccc1)C(=O)O] | (2S)-2-({[(3,4-dichlorophenyl)amino]carbonyl}amino)-3-phenylpropanoic acid | 10 μM (0.57) |
| 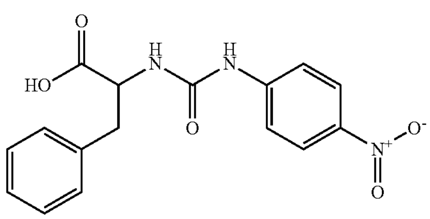 [SMILES: O=C(Nc1ccc([N+](=O)[O-])cc1)NC(Cc1ccccc1)C(=O)O] | (2S)-2-({[(4-nitrophenyl)amino]carbonyl}amino)-3-phenylpropanoic acid | 574 nM (0.82) |
| 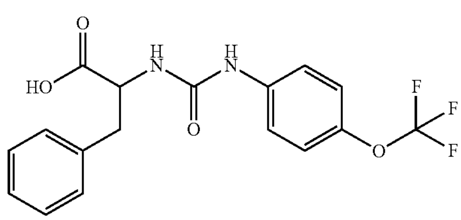 [SMILES: O=C(Nc1ccc(OC(F)(F)F)cc1)NC(Cc1ccccc1)C(=O)O] | 3-phenyl-2-[({[4-(trifluoromethoxy)phenyl]amino}carbonyl)amino]propanoic acid | 1572 nM (0.79) |
| 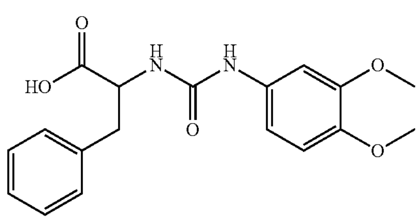 [SMILES: COc1ccc(NC(=O)NC(Cc2ccccc2)C(=O)O)cc1OC] | 2-({[(3,4-dimethoxyphenyl)amino]carbonyl}amino)-3-phenylpropanoic acid | 2793 nM (0.72) |
| 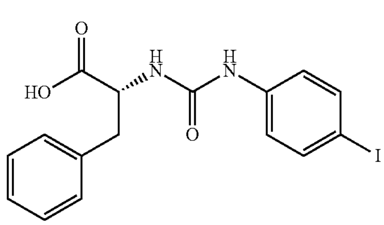 [SMILES: O=C(Nc1ccc(I)cc1)N[C@H](Cc1ccccc1)C(=O)O] | methyl 2-({[(4-iodophenyl)amino]carbonyl}amino)-3-phenylpropanoate | 14.3 nM (1.0) |

TABLE 1-continued

| Structure | IUPAC name | FPRL-1 Gα16-CHO EC$_{50}$ (efficacy) |
|---|---|---|
| 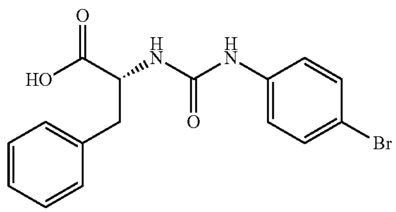 [SMILES: O=C(Nc1ccc(Br)cc1)N[C@H](Cc1ccccc1)C(=O)O] | (2S)-2-({[(4-bromophenyl)amino]carbonyl}amino)-3-phenylpropanoic acid | 31 nM (1.0) |
| 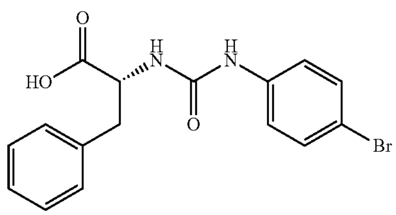 [SMILES: O=C(Nc1ccc(Br)cc1)N[C@H](Cc1ccccc1)C(=O)O] | (2R)-2-({[(4-bromophenyl)amino]carbonyl}amino)-3-phenylpropanoic acid | 1819 nM (0.99) |
| 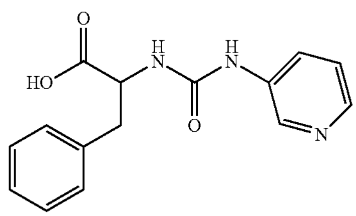 [SMILES: O=C(Nc1cccnc1)NC(Cc1ccccc1)C(=O)O] | 3-phenyl-2-{[(pyridin-3-ylamino)carbonyl]amino}propanoic acid |  |
| 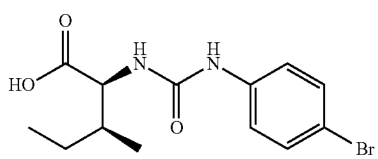 [SMILES: CC[C@H](C)[C@H](NC(=O)Nc1ccc(Br)cc1)C(=O)O] | (2S,3S)-2-({[(4-bromophenyl)amino]carbonyl}amino)-3-methylpentanoic acid | 4.1 nM (0.89) |
| 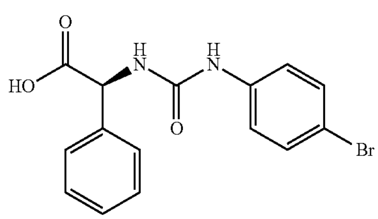 [SMILES: O=C(Nc1ccc(Br)cc1)N[C@H](C(=O)O)c1ccccc1] | (2S)-({[(4-bromophenyl)amino]carbonyl}amino)(phenyl)acetic acid | 25.8 nM (0.94) |
| 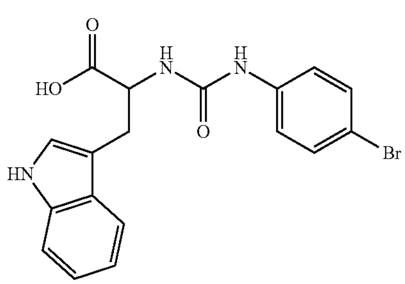 [SMILES: O=C(Nc1ccc(Br)cc1)NC(Cc1c[nH]c2ccccc12)C(=O)O] | 2-({[(4-bromophenyl)amino]carbonyl}amino)-3-(1H-indol-3-yl)propanoic acid | 67.0 nM (0.89) |
| 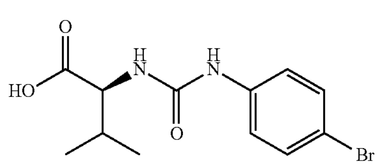 [SMILES: CC(C)[C@H](NC(=O)Nc1ccc(Br)cc1)C(=O)O] | (2S)-2-({[(4-bromophenyl)amino]carbonyl}amino)-3-methylbutanoic acid | 72 nM (0.91) |

TABLE 1-continued

| Structure | IUPAC name | FPRL-1 Gal6-CHO EC$_{50}$ (efficacy) |
|---|---|---|
| (structure of (2S)-2-({[(4-bromo-2-fluorophenyl)amino]carbonyl}amino)-3-methylbutanoic acid) | (2S)-2-({[(4-bromo-2-fluorophenyl)amino]carbonyl}amino)-3-methylbutanoic acid | 152 nM (0.91) |

US 2005/0137230 A1 and U.S. Pat. No. 7,820,673 disclose inhibitors of coagulation Factor Xa and can be employed for the prophylaxis and/or therapy of thromboembolic diseases and/or the treatment of tumors. 2-({[(4-chlorophenyl)amino]carbonyl}amino)-3-phenylpropanoic acid, (2S)-2-({[(4-methoxyphenyl)amino]carbonyl}amino)-3-phenylpropanoic acid, (2S)-3-phenyl-2-[({[4-(trifluoromethyl)phenyl]amino}carbonyl)amino]propanoic acid, methyl 2-({[(4-iodophenyl)amino]carbonyl}amino)-3-phenylpropanoate, (2S)-2-({[(4-bromophenyl)amino]carbonyl}amino)-3-phenylpropanoic acid, (2R)-2-({[(4-bromophenyl)amino]carbonyl}amino)-3-phenylpropanoic acid, are intermediates in the synthesis of urea derivatives as activated blood coagulation factor X (FXa) inhibitors.

JP 63232846 discloses the resolution of N-(p-bromophenylcarbamyl) derivatives ((2S)-2-({[(4-bromophenyl)amino]carbonyl}amino)-3-phenylpropanoic acid, (2S,3S)-2-({[(4-bromophenyl)amino]carbonyl}amino)-3-methylpentanoic acid, 2-({[(4-bromophenyl)amino]carbonyl}amino)-3-(1H-indol-3-yl)propanoic acid, (2S)-2-({[(4-bromophenyl)amino]carbonyl}amino)-3-methylbutanoic acid) on HPLC column with novel chromatographic chiral stationary phases.

Journal of Chromatography (1987), 404(1), 117-22 and Chromatographia (1987), 23(10), 727-30 describe the resolution of p-Bromophenylcarbamyl derivatives of enantiomeric protein amino acids ((2R)-2-({[(4-bromophenyl)amino]carbonyl}amino)-3-phenylpropanoic acid, (2S)-2-({[(4-bromophenyl)amino]carbonyl}amino)-3-phenylpropanoic acid), on novel chiral stationary phase by elution with an aqueous mobile phase.

Biochimica et Biophysica Acta, Nucleic Acids and Protein Synthesis (1972), 272(4), 667-71 describes compound (2S)-2-({[(4-nitrophenyl)amino]carbonyl}amino)-3-phenylpropanoic acid) in poly(uridylic acid)-dependent binding of para nitrophenyl-carbamyl-phenylalanyl tRNA.

In another aspect, agonists of FPR2 are compounds selected from Table 2:

TABLE 2

| Structure | IUPAC name | FPRL-1 Gal6-CHO EC50 (efficacy) |
|---|---|---|
| (structure) | 1-(4-chlorophenyl)-3-(2,4-dioxo-1,3-diazaspiro[4,5]decan-3-yl)urea | 49 nM (0.98) |
| (structure) | 1-(4-chlorophenyl)-3-(4-ethyl-4-methyl-2,5-dioxoimidazolidin-1-yl)urea | 157 nM (0.96) |
| (structure) | 1-[4-methyl-2,5-dioxo-4-(2-phenylethyl)imidazolidin-1-yl]-3-phenylurea | 223 nM (1.0) |

TABLE 2-continued

| Structure | IUPAC name | FPRL-1 Gal16-CHO EC50 (efficacy) |
|---|---|---|
| 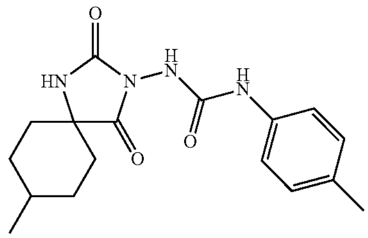 [SMILES: Cc1ccc(NC(=O)NN2C(=O)NC3(CCC(C)CC3)C2=O)cc1] | 1-(8-methyl-2,4-dioxo-1,3-diazaspiro[4,5]decan-3-yl)-3-(p-tolyl)urea | 363 nM (0.91) |
| 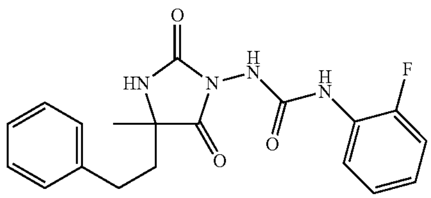 [SMILES: CC1(CCc2ccccc2)NC(=O)N(NC(=O)Nc2ccccc2F)C1=O] | 1-(2-fluorophenyl)-3-[4-methyl-2,5-dioxo-4-(2-phenylethyl)imidazolidin-1-yl]urea | 258 nM (0.94) |

Compounds of Table 2 are available from Chemical Libraries such as Aurora Fine Chemicals.

In another aspect, agonists of FPR2 are compounds selected from Table 3:

TABLE 3

| Structure | IUPAC name | FPRL-1 Gal16-CHO $EC_{50}$ (efficacy) |
|---|---|---|
| 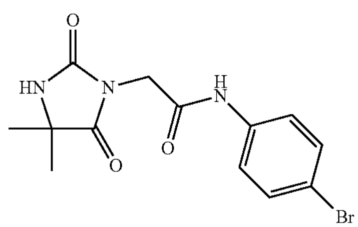 [SMILES: CC1(C)NC(=O)N(CC(=O)Nc2ccc(Br)cc2)C1=O] | N-(4-bromophenyl)-2-(4,4-dimethyl-2,5-dioxoimidazolidin-1-yl)acetamide | 719 nM (0.94) |
| 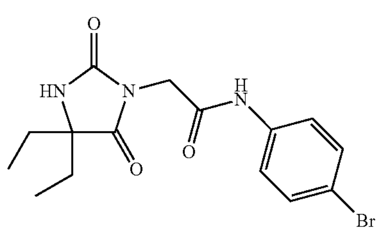 [SMILES: CCC1(CC)NC(=O)N(CC(=O)Nc2ccc(Br)cc2)C1=O] | N-(4-bromophenyl)-2-(4,4-diethyl-2,5-dioxoimidazolidin-1-yl)acetamide | 96 nM (0.98) |
| 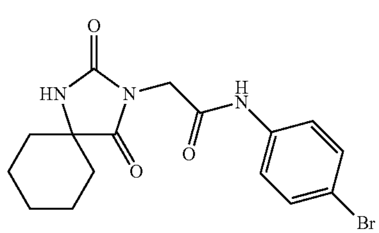 [SMILES: O=C(CN1C(=O)NC2(CCCCC2)C1=O)Nc1ccc(Br)cc1] | N-(4-bromophenyl)-2-(2,4-dioxo-1,3-diazaspiro[4.5]dec-3-yl)acetamide | 738 nM (0.89) |

TABLE 3-continued

| Structure | IUPAC name | FPRL-1 Gal16-CHO EC$_{50}$ (efficacy) |
|---|---|---|
| 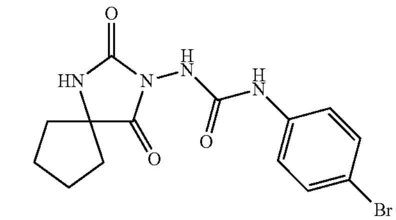 [SMILES: O=C(Nc1ccc(Br)cc1)NN1C(=O)NC2(CCCC2)C1=O] | N-(4-bromophenyl)-2-(2,4-dioxo-1,3-diazaspiro[4.4]non-3-yl)acetamide | 322 nM (0.96) |
| 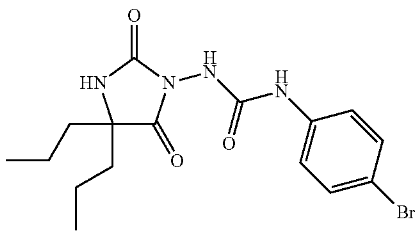 [SMILES: CCCC1(CCC)NC(=O)N(NC(=O)Nc2ccc(Br)cc2)C1=O] | N-(4-bromophenyl)-2-(2,5-dioxo-4,4-dipropylimidazolidin-1-yl)acetamide | 645 nM (0.98) |
| 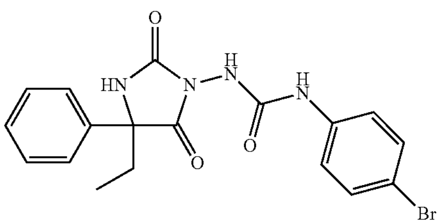 [SMILES: CCC1(c2ccccc2)NC(=O)N(NC(=O)Nc2ccc(Br)cc2)C1=O] | N-(4-bromophenyl)-2-(4-ethyl-2,5-dioxo-4-phenylimidazolidin-1-yl)acetamide | 523 nM (0.83) |
| 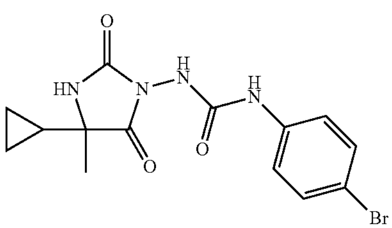 [SMILES: CC1(C2CC2)NC(=O)N(NC(=O)Nc2ccc(Br)cc2)C1=O] | N-(4-bromophenyl)-2-(4-cyclopropyl-4-methyl-2,5-dioxoimidazolidin-1-yl)acetamide | 166 nM (0.84) |
| 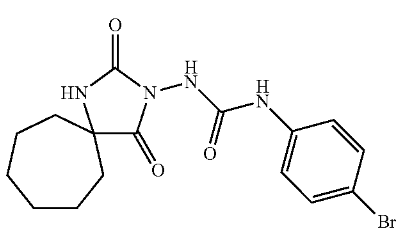 [SMILES: O=C(Nc1ccc(Br)cc1)NN1C(=O)NC2(CCCCCC2)C1=O] | N-(4-bromophenyl)-2-(2,4-dioxo-1,3-diazaspiro[4.6]undec-3-yl)acetamide | 679 nM (0.96) |
| 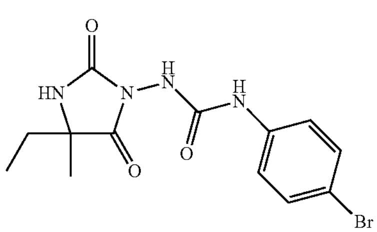 [SMILES: CCC1(C)NC(=O)N(NC(=O)Nc2ccc(Br)cc2)C1=O] | N-(4-bromophenyl)-2-(4-ethyl-4-methyl-2,5-dioxoimidazolidin-1-yl)acetamide | 485 nM (1.0) |

TABLE 3-continued

| Structure | IUPAC name | FPRL-1 Gal16-CHO $EC_{50}$ (efficacy) |
|---|---|---|
| 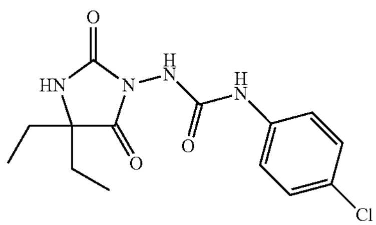 [SMILES: CCC1(CC)NC(=O)N(NC(=O)Nc2ccc(Cl)cc2)C1=O] | N-(4-chlorophenyl)-2-(4,4-diethyl-2,5-dioxoimidazolidin-1-yl)acetamide | 314 nM (0.79) |
| 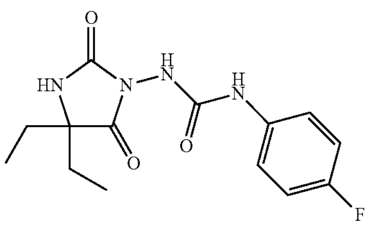 [SMILES: CCC1(CC)NC(=O)N(NC(=O)Nc2ccc(F)cc2)C1=O] | 2-(4,4-diethyl-2,5-dioxoimidazolidin-1-yl)-N-(4-fluorophenyl)acetamide | 2771 nM (0.67) |
| 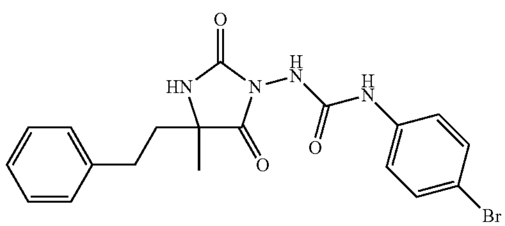 [SMILES: CC1(CCc2ccccc2)NC(=O)N(NC(=O)Nc2ccc(Br)cc2)C1=O] | N-(4-bromophenyl)-2[4-methyl-2,5-dioxo-4-(2-phenylethyl)imidazolidin-1-yl]acetamide | 860 nM (0.88) |
| 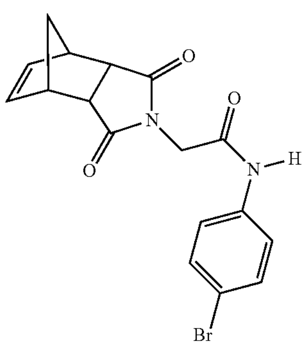 [SMILES: O=C(CN1C(=O)C2C3C=CC(C3)C2C1=O)Nc1ccc(Br)cc1] | N-(4-bromophenyl)-1,3,3a,4,7,7a-hexahydro-1,3-dioxo-4,7-methano-2H-isoindole-2-acetamide | 575 (0.90) |
| 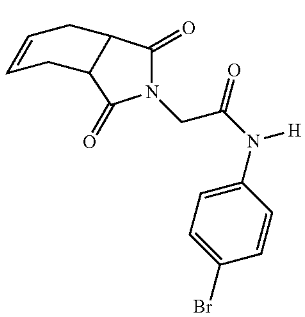 [SMILES: O=C(CN1C(=O)C2CC=CCC2C1=O)Nc1ccc(Br)cc1] | N-(4-bromophenyl)-1,3,3a,4,7,7a-hexahydro-1,3-dioxo-2H-isoindole-2-acetamide | 395 (0.98) |

The compounds of Table 3 are available from Chemical Libraries such as Chemical Block Ltd.

In a further embodiment of the invention, there are provided methods for treating disorders associated with modulation of the N-formyl peptide receptor like-1 receptor. Such methods can be performed, for example, by administering to a subject in need thereof a pharmaceutical composition containing a therapeutically effective amount of at least one compound of the invention.

Therapeutic utilities of the N-formyl peptide receptor like-1 receptor modulators are dermatological inflammation and diseases including, but not limited to, dermal wound healing, hypertrophic scars, keloids, burns, rosacea, atopic dermatitis, acne, psoriasis, seborrheic dermatitis, actinic keratoses, basal cell carcinoma, squamous cell carcinoma, melanoma, viral warts, photoaging, photodamage, melasma, post-inflammatory hyperpigmentation, other disorders of pigmentation, and alopecia (scarring and non-scarring forms).

These compounds are useful for the treatment of mammals, including humans, with a range of conditions and diseases that are alleviated by the N-formyl peptide receptor like-1 receptor modulation: dermatological inflammation and diseases including, but not limited to, dermal wound healing, hypertrophic scars, keloids, burns, rosacea, atopic dermatitis, acne, psoriasis, seborrheic dermatitis, actinic keratoses, basal cell carcinoma, squamous cell carcinoma, melanoma, viral warts, photoaging, photodamage, melasma, post-inflammatory hyperpigmentation, other disorders of pigmentation, and alopecia (scarring and non-scarring forms).

In still another embodiment of the invention, there are provided methods for treating disorders associated with modulation of the FPRL-1 receptor. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

Pharmaceutical compositions containing invention compounds may be in a form suitable for topical use, for example, as oily suspensions, as solutions or suspensions in aqueous liquids or nonaqueous liquids, or as oil-in-water or water-in-oil liquid emulsions.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of the N-formyl peptide receptor like-1 (FPRL-1) receptor. Thus, in further embodiments of the invention, there are provided methods for treating a disorder associated with modulation of the N-formyl peptide receptor like-1 (FPRL-1) receptor. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

Materials and Methods

Figure 2:
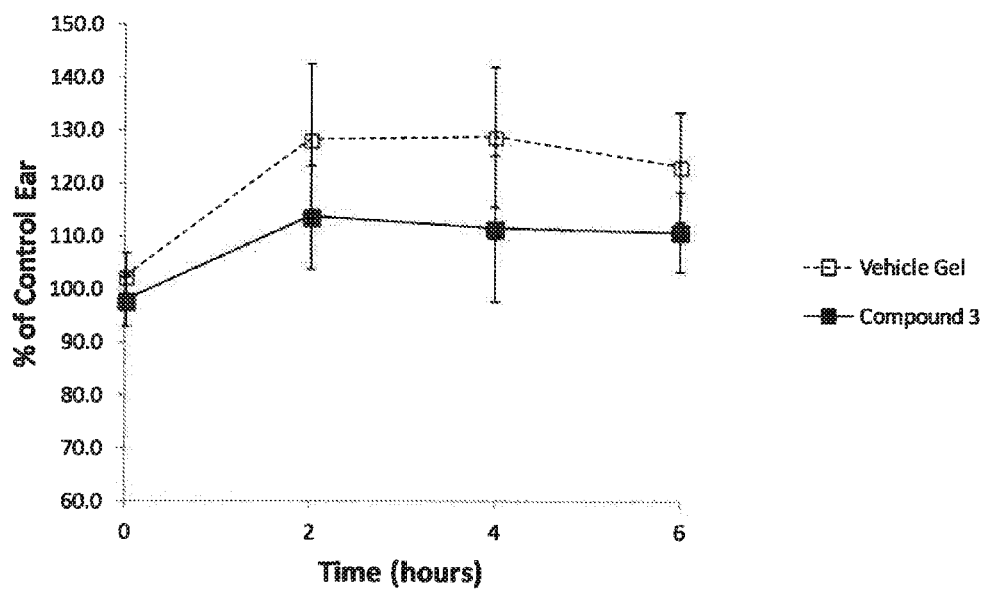
FIG. 2 FPR2 agonists block inflammation induced by LL-37 in mouse ears p<0.05 vs. vehicle, at all-time points.
Figure 2:
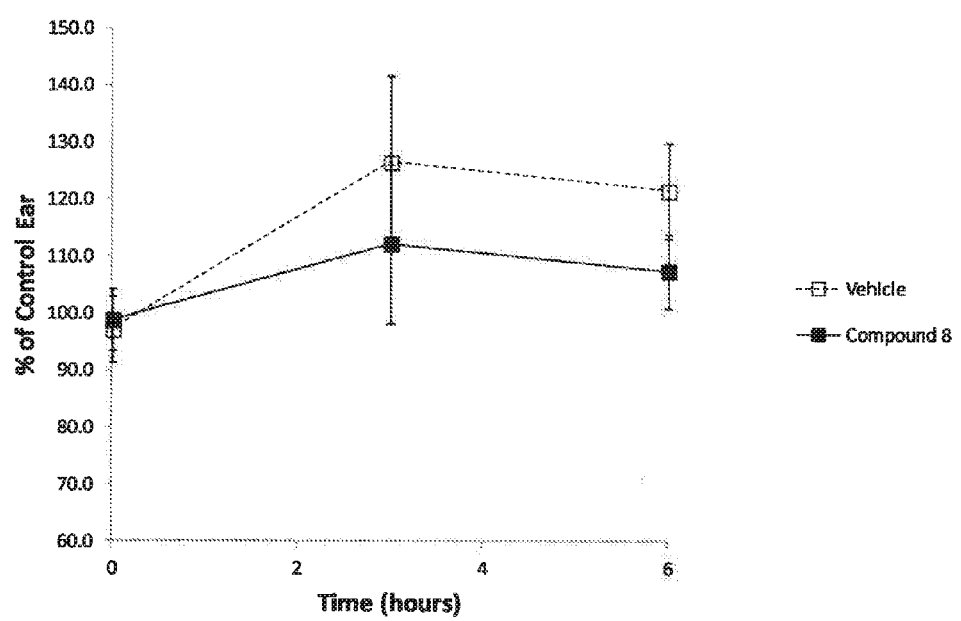

FPR2 agonists would be expected to have significant effects in many different types of dermatological inflammation, but have been exemplified by demonstrating wound healing in a mouse model of punch dermal wound (FIG. 2). Anti-inflammatory activity in this model has been exemplified with the FPR2 agonists described in Table 4.

FLIPR: HEK-Gα16 cells stably expressing the human FPR2 receptor was utilized. Cells were plated into 384-well poly-D-lysine coated plates at a density of 18,000 cells per well one day prior to use. The growth media was DMEM medium supplemented with 10% fetal bovine serum (FBS), 1% antibiotic-antimycotic, 50 µg/ml hygromycin, and 400 µg/ml geneticin. On the day of the experiment, the cells were washed twice with Hank's Balanced Salt Solution supplemented with 20 mM HEPES (HBSS/hepes buffer). The cells were then dye loaded with 2 µM Fluo-4 diluted in the HBSS/Hepes buffer and incubated at 37° C. for 40 minutes. Extracellular dye was removed by washing the cell plates four times prior to placing the plates in the FLIPR (Fluorometric Imaging Plate Reader, Molecular Devices). Ligands were diluted in HBSS/Hepes buffer and prepared in 384-well microplates. Data for $Ca^{+2}$ responses were obtained in relative fluorescence units.

TABLE 4

| Compound number | Structure | IUPAC name | FPR2 EC50 (% eff) |
|---|---|---|---|
| 1 | 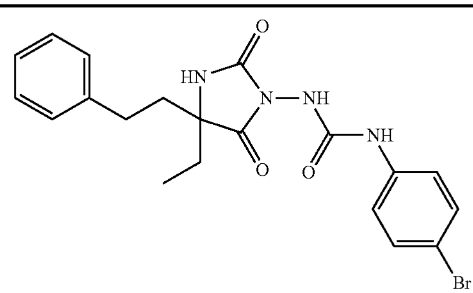 | 1-(4-bromophenyl)-3-[4-ethyl-2,5-dioxo-4-(2-phenylethyl)imidazolidin-1-yl]urea | 3.0 (0.96) |
| 2 | 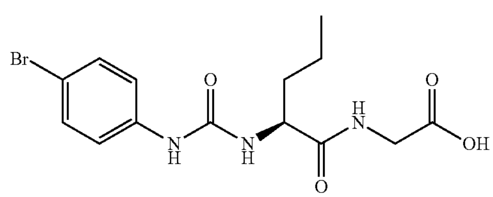 [SMILES: CCC[C@H](NC(=O)Nc1ccc(Br)cc1)C(=O)NCC(=O)O] | {[(2S)-2-{[(4-bromophenyl)carbamoyl]amino}pentanoyl]amino}acetic acid | 2 (0.91) |
| 3 | 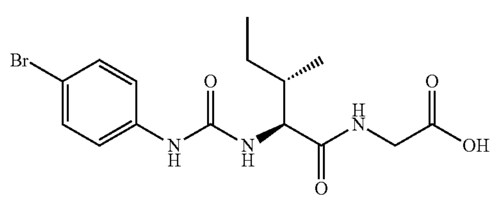 [SMILES: CC[C@H](C)[C@H](NC(=O)Nc1ccc(Br)cc1)C(=O)NCC(=O)O] | {[(2S,3S)-2-{[(4-bromophenyl)carbamoyl]amino}-3-methylpentanoyl]amino} acetic acid | 1.98 (1.0) |
| 4 | 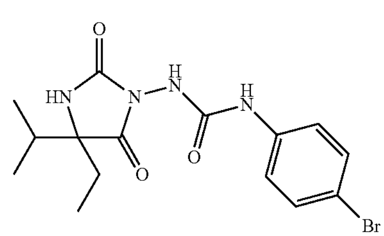 [SMILES: CCC1(C(C)C)NC(=O)N(NC(=O)Nc2ccc(Br)cc2)C1=O] | 1-(4-bromophenyl)-3-[4-ethyl-2,5-dioxo-4-(propan-2-yl)imidazolidin-1-yl]urea | 6.7 (0.90) |

TABLE 4-continued

| Compound number | Structure | IUPAC name | FPR2 EC50 (% eff) |
|---|---|---|---|
| 5 | 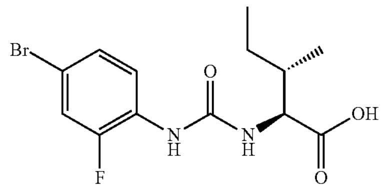 [SMILES: CC[C@H](C)[C@H](NC(=O)Nc1ccc(Br)cc1F)C(=O)O] | (2S,3S)-2-{[(4-bromo-2-fluorophenyl)carbamoyl]amino}-3-methylpentanoic acid | 31 (0.96) |
| 6 | 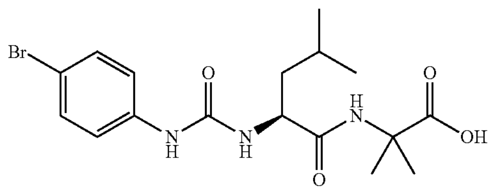 [SMILES: CC(C)C[C@H](NC(=O)Nc1ccc(Br)cc1)C(=O)NC(C)(C)C(=O)O] | 2-{[(2S)-2-{[(4-bromophenyl)carbamoyl]amino}-4-methylpentanoyl]amino}-2-methylpropanoic acid | 1.66 (0.91) |
| 7 | 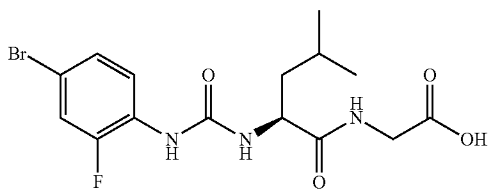 [SMILES: CC(C)C[C@H](NC(=O)Nc1ccc(Br)cc1F)C(=O)NCC(=O)O] | {[(2S)-2-{[(4-bromo-2-fluorophenyl)carbamoyl]amino}-4-methylpentanoyl]amino} acetic acid | 3.57 (1.0) |
| 8 | 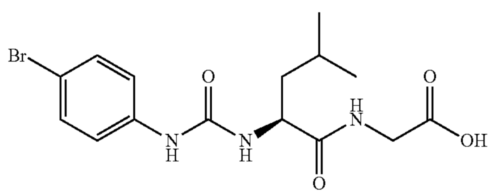 [SMILES: CC(C)C[C@H](NC(=O)Nc1ccc(Br)cc1)C(=O)NCC(=O)O] | {[(2S)-2-{[(4-bromophenyl)carbamoyl]amino}-4-methylpentanoyl]amino} acetic acid | 0.78 (0.78) |
| 9 | 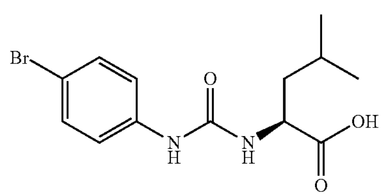 [SMILES: CC(C)C[C@H](NC(=O)Nc1ccc(Br)cc1)C(=O)O] | (2S)-2-{[(4-bromophenyl)carbamoyl]amino}-4-methylpentanoic acid | 5.95 (0.77) |
| 10 | 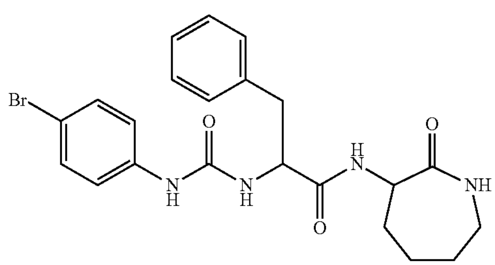 [SMILES: O=C(Nc1ccc(Br)cc1)NC(Cc1ccccc1)C(=O)NC1CCCCNC1=O] | 2-{[(4-bromophenyl)carbamoyl]amino}-N-(2-oxoazepan-3-yl)-3-phenylpropanamide | 11 nM (0.89) |
| 11 | 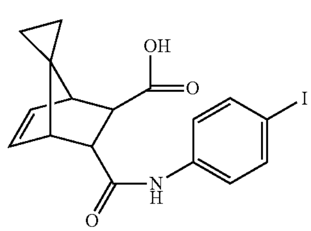 [SMILES: O=C(O)C1C(C(=O)Nc2ccc(I)cc2)C2C=CC1C21CC1] | 3-[(4-iodophenyl)carbamoyl]spiro[bicyclo[2.2.1]heptane-7,1'-cyclopropane]-5-ene-2-carboxylic acid | 1.6 nM (1.00) |

TABLE 4-continued

| Compound number | Structure | IUPAC name | FPR2 EC50 (% eff) |
| --- | --- | --- | --- |
| 12 | 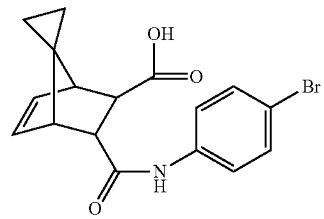 [SMILES: O=C(O)C1C(C(=O)Nc2ccc(Br)cc2)C2C=CC1C21CC1] | 3-[(4-bromophenyl)carbamoyl]spiro[bicyclo[2.2.1]heptane-7,1'-cyclopropane]-5-ene-2-carboxylic acid | 4 nM (0.97) |
| 13 | 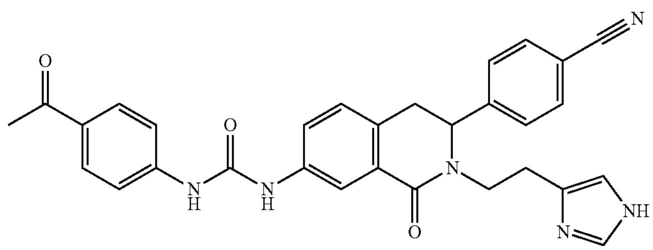 [SMILES: CC(=O)c1ccc(NC(=O)Nc2ccc3c(c2)C(=O)N(CCc2c[nH]cn2)C(c2ccc(C#N)cc2)C3)cc1] | 1-(4-acetylphenyl)-3-{3-(4-cyanophenyl)-2-[2-(1H-imidazol-4-yl)ethyl]-1-oxo-1,2,3,4-tetrahydroisoquinolin-7-yl}urea | 11 nM (0.80) |
| 14 | 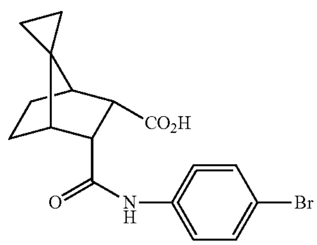 | rel-(2R,3S)-3-[(4-bromophenyl)carbamoyl]spiro[bicyclo[2.2.1]heptane-7,1'-cyclopropane]-2-carboxylic acid | 4 nM (0.90) |
| 15 | 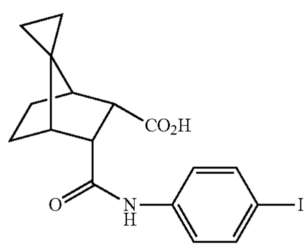 | 3-[(4-iodophenyl)carbamoyl]spiro[bicyclo[2.2.1]heptane-7,1'-cyclopropane]-2-carboxylic acid | 0.60 nM (0.87) |
| 16 | 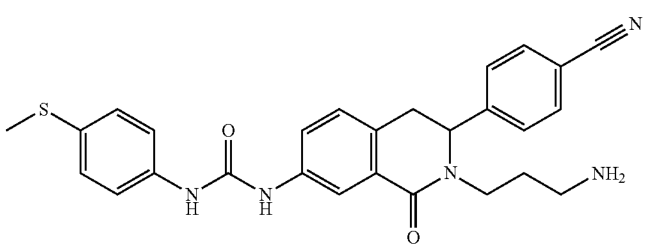 [SMILES: CSc1ccc(NC(=O)Nc2ccc3c(c2)C(=O)N(CCCN)C(c2ccc(C#N)cc2)C3)cc1] | 1-[2-(3-aminopropyl)-3-(4-cyanophenyl)-1-oxo-1,2,3,4-tetrahydroisoquinolin-7-yl]-3-[4-(methylsulfanyl)phenyl]urea | 2.5 nM (0.70) |
| 17 | 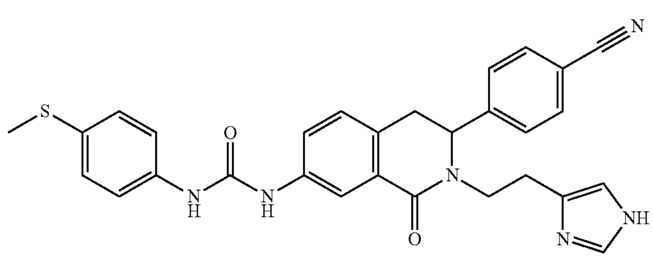 [SMILES: CSc1ccc(NC(=O)Nc2ccc3c(c2)C(=O)N(CCc2c[nH]cn2)C(c2ccc(C#N)cc2)C3)cc1] | 1-{3-(4-cyanophenyl)-2-[2-(1H-imidazol-4-yl)ethyl]-1-oxo-1,2,3,4-tetrahydroisoquinolin-7-yl}-3-[4-(methylsulfanyl)phenyl]urea | 5.5 nM (0.92) |

TABLE 4-continued

| Compound number | Structure | IUPAC name | FPR2 EC50 (% eff) |
|---|---|---|---|
| 18 | 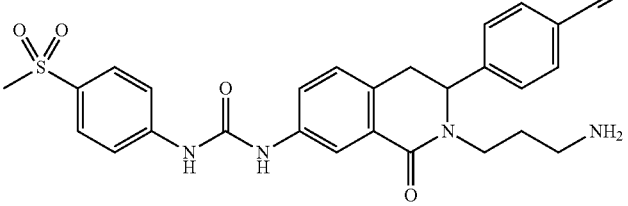 | 1-[2-(3-aminopropyl)-3-(4-cyanophenyl)-1-oxo-1,2,3,4-tetrahydroisoquinolin-7-yl]-3-[4-(methylsulfonyl)phenyl]urea | 10 nM (0.86) |
| 19 | 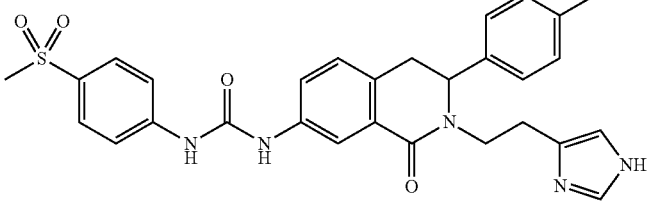 | 1-{3-(4-cyanophenyl)-2-[2-(1H-imidazol-4-yl)ethyl]-1-oxo-1,2,3,4-tetrahydroisoquinolin-7-yl}-3-[4-(methylsulfonyl)phenyl]urea | 20 nM (1.00) |
| 20 | 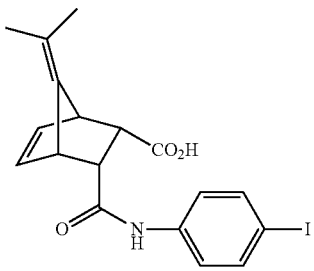 [SMILES: CC(C)=C1C2C=CC1C(C(=O)Nc1ccc(I)cc1)C2C(=O)O] | 3-[(4-iodophenyl)carbamoyl]-7-(propan-2-ylidene)bicyclo[2.2.1]hept-5-ene-2-carboxylic acid | 11 nM (0.94) |
| 21 | 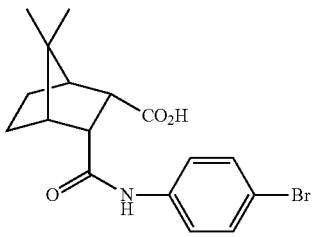 [SMILES: CC1(C)C2CCC1C(C(=O)Nc1ccc(Br)cc1)C2C(=O)O] | 3-[(4-bromophenyl)carbamoyl]-7,7-dimethylbicyclo[2.2.1]heptane-2-carboxylic acid | 10 nM (0.85) |
| 22 | 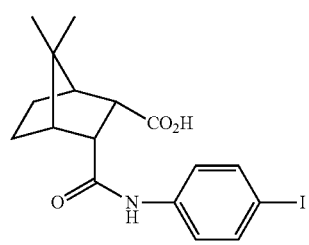 [SMILES: CC1(C)C2CCC1C(C(=O)Nc1ccc(I)cc1)C2C(=O)O] | 3-[(4-iodophenyl)carbamoyl]-7,7-dimethylbicyclo[2.2.1]heptane-2-carboxylic acid | 1.7 nM (0.97) |
| 23 | 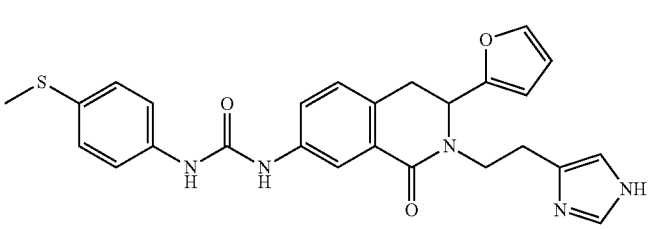 [SMILES: CSc1ccc(NC(=O)Nc2ccc3c(c2)C(=O)N(CCc2c[nH]cn2)C(c2ccco2)C3)cc1] | 1-{3-(furan-2-yl)-2-[2-(1H-imidazol-4-yl)ethyl]-1-oxo-1,2,3,4-tetrahydroisoquinolin-7-yl}-3-[4-(methylsulfanyl)phenyl]urea | 19 nM (0.83) |

TABLE 4-continued

| Compound number | Structure | IUPAC name | FPR2 EC50 (% eff) |
|---|---|---|---|
| 24 | 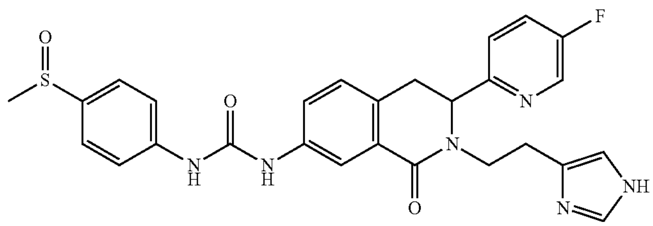 [SMILES: CS(=O)c1ccc(NC(=O)Nc2ccc3c(c2)C(=O)N(CCc2c[nH]cn2)C(c2ccc(F)cn2)C3)cc1] | 1-{3-(5-fluoropyridin-2-yl)-2-[2-(1H-imidazol-4-yl)ethyl]-1-oxo-1,2,3,4-tetrahydroisoquinolin-7-yl}-3-[4-(methylsulfinyl)phenyl]urea | 11.8 nM (0.93) |
| 25 | 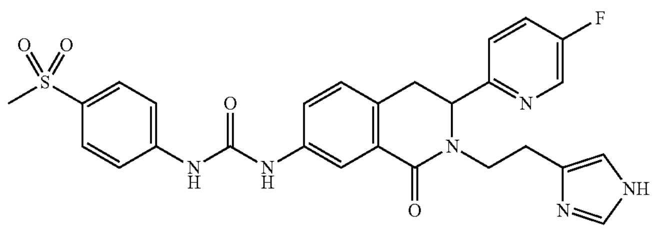 [SMILES: CS(=O)(=O)c1ccc(NC(=O)Nc2ccc3c(c2)C(=O)N(CCc2c[nH]cn2)C(c2ccc(F)cn2)C3)cc1] | 1-{3-(5-fluoropyridin-2-yl)-2-[2-(1H-imidazol-4-yl)ethyl]-1-oxo-1,2,3,4-tetrahydroisoquinolin-7-yl}-3-[4-(methylsulfonyl)phenyl]urea | 10.5 nM (1.0) |
| 26 | 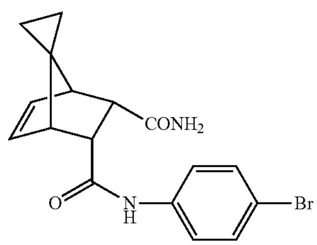 [SMILES: NC(=O)C1C(C(=O)Nc2ccc(Br)cc2)C2C=CC1C21CC1] | N-(4-bromophenyl)spiro[bicyclo[2.2.1]heptane-7,1'-cyclopropane]-5-ene-2,3-dicarboxamide | 4.8 nM (0.91) |
| 27 | 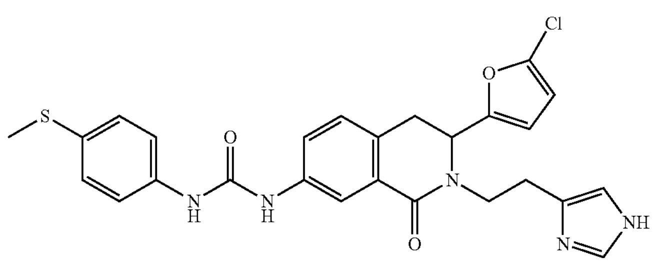 [SMILES: CSc1ccc(NC(=O)Nc2ccc3c(c2)C(=O)N(CCc2c[nH]cn2)C(c2ccc(Cl)o2)C3)cc1] | 1-{3-(5-chlorofuran-2-yl)-2-[2-(1H-imidazol-4-yl)ethyl]-1-oxo-1,2,3,4-tetrahydroisoquinolin-7-yl}-3-[4-(methylsulfanyl)phenyl]urea | 17 nM (0.81) |
| 28 | 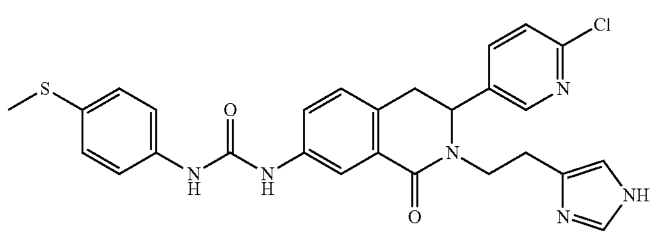 [SMILES: CSc1ccc(NC(=O)Nc2ccc3c(c2)C(=O)N(CCc2c[nH]cn2)C(c2ccc(Cl)nc2)C3)cc1] | 1-{3-(6-chloropyridin-3-yl)-2-[2-(1H-imidazol-4-yl)ethyl]-1-oxo-1,2,3,4-tetrahydroisoquinolin-7-yl}-3-[4-(methylsulfanyl)phenyl]urea | 6.3 nM (0.89) |
| 29 | 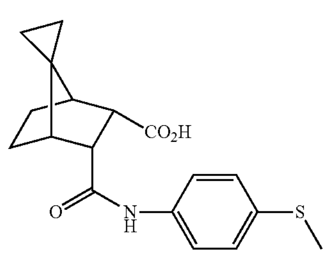 [SMILES: CSc1ccc(NC(=O)C2C(C(=O)O)C3CCC2C32CC2)cc1] | 3-{[4-(methylsulfanyl)phenyl]carbamoyl}spiro[bicyclo[2.2.1]heptane-7,1'-cyclopropane]-2-carboxylic acid | 7 nM (0.96) |

TABLE 4-continued

| Compound number | Structure | IUPAC name | FPR2 EC50 (% eff) |
|---|---|---|---|
| 30 | 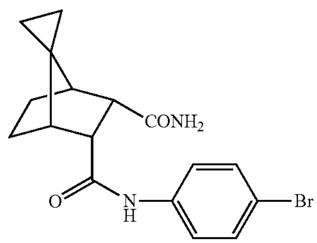 [SMILES: NC(=O)C1C(C(=O)Nc2ccc(Br)cc2)C2CCC1C21CC1] | N-(4-bromophenyl)spiro[bicyclo[2.2.1]heptane-7,1'-cyclopropane]-2,3-dicarboxamide | 2.5 nM (0.96) |
| 31 | 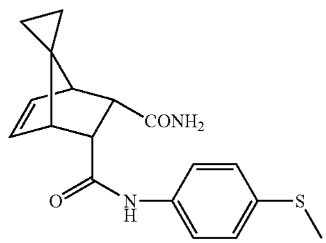 [SMILES: CSc1ccc(NC(=O)C2C(C(N)=O)C3C=CC2C32CC2)cc1] | 3-{[4-(methylsulfanyl)phenyl]carbamoyl}spiro[bicyclo[2.2.1]heptane-7,1'-cyclopropane]-5-ene-2-carboxylic acid | 14 nM (0.85) |
| 32 | 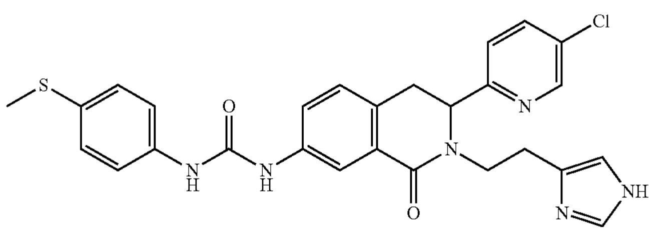 [SMILES: CSc1ccc(NC(=O)Nc2ccc3c(c2)C(=O)N(CCc2c[nH]cn2)C(c2ccc(Cl)cn2)C3)cc1] | 1-{3-(5-chloropyridin-2-yl)-2-[2-(1H-imidazol-4-yl)ethyl]-1-oxo-1,2,3,4-tetrahydroisoquinolin-7-yl}-3-[4-(methylsulfanyl)phenyl]urea | 13.5 nM (0.91) |
| 33 | 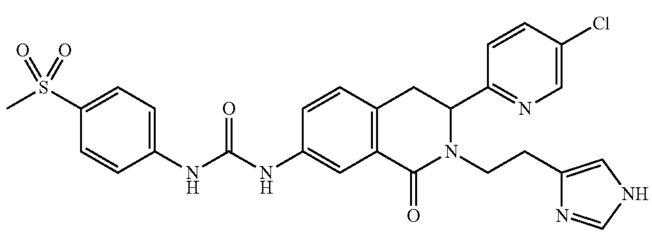 | 1-{3-(5-chloropyridin-2-yl)-2-[2-(1H-imidazol-4-yl)ethyl]-1-oxo-1,2,3,4-tetrahydroisoquinolin-7-yl}-3-[4-(methylsulfonyl)phenyl]urea | 9.5 nM (0.99) |
| 34 | 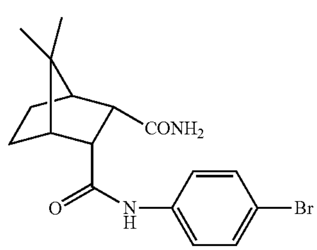 [SMILES: CC1(C)C2CCC1C(C(=O)Nc1ccc(Br)cc1)C2C(N)=O] | N-(4-bromophenyl)-7,7-dimethylbicyclo[2.2.1]heptane-2,3-dicarboxamide | 15 nM (0.83) |
| 35 | 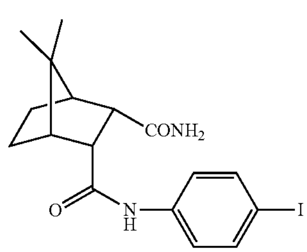 [SMILES: CC1(C)C2CCC1C(C(=O)Nc1ccc(I)cc1)C2C(N)=O] | N-(4-iodophenyl)-7,7-dimethylbicyclo[2.2.1]heptane-2,3-dicarboxamide | 2.6 nM (0.81) |

TABLE 4-continued

| Compound number | Structure | IUPAC name | FPR2 EC50 (% eff) |
|---|---|---|---|
| 36 | 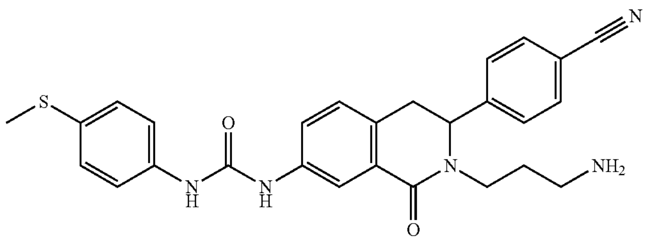 [SMILES: CSc1ccc(NC(=O)Nc2ccc3c(c2)C(=O)N(CCCN)C(c2ccc(C#N)cc2)C3)cc1] | (+)1-[(3R)-2-(3-aminopropyl)-3-(4-cyanophenyl)-1-oxo-1,2,3,4-tetrahydroisoquinolin-7-yl]-3-[4-(methylsulfanyl)phenyl]urea | 3.3 nM (0.97) |
| 37 | 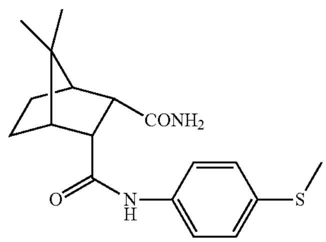 [SMILES: CSc1ccc(NC(=O)C2C(C(N)=O)C3CCC2C3(C)C)cc1] | 7,7-dimethyl-N-[4-(methylsulfanyl)phenyl]bicyclo[2.2.1]heptane-2,3-dicarboxamide | 17 nM (0.85) |
| 38 | 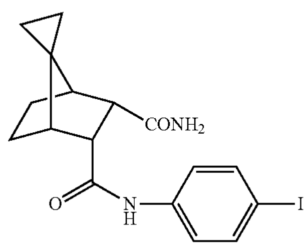 [SMILES: NC(=O)C1C(C(=O)Nc2ccc(I)cc2)C2CCC1C21CC1] | N-(4-iodophenyl)spiro[bicyclo[2.2.1]heptane-7,1'-cyclopropane]-2,3-dicarboxamide | 1.9 nM (0.95) |
| 39 | 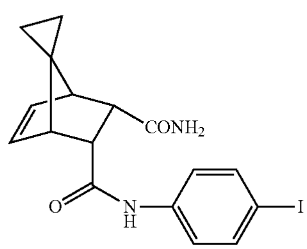 [SMILES: NC(=O)C1C(C(=O)Nc2ccc(I)cc2)C2C=CC1C21CC1] | N-(4-iodophenyl)spiro[bicyclo[2.2.1]heptane-7,1'-cyclopropane]-5-ene-2,3-dicarboxamide | 1.6 nM (0.90) |
| 40 | 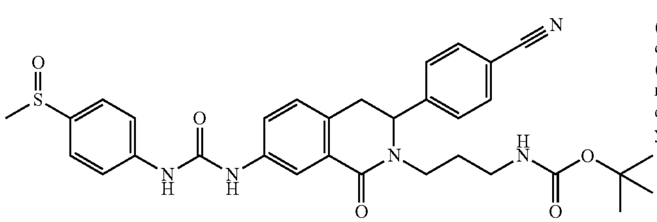 [SMILES: CS(=O)c1ccc(NC(=O)Nc2ccc3c(c2)C(=O)N(CCCNC(=O)OC(C)(C)C)C(c2ccc(C#N)cc2)C3)cc1] | (+) tert-butyl {3-[(3R)-3-(4-cyanophenyl)-7-({[4-(methylsulfinyl)phenyl]carbamoyl}amino)-1-oxo-3,4-dihydroisoquinolin-2(1H)-yl]propyl}carbamate | 103 nM (0.91) |
| 41 | 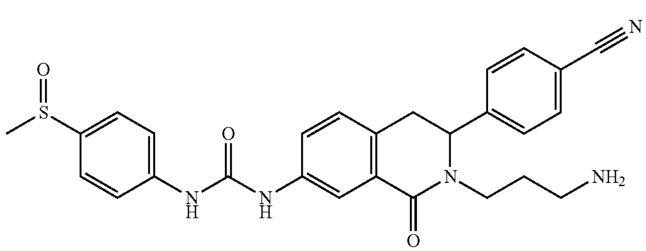 [SMILES: CS(=O)c1ccc(NC(=O)Nc2ccc3c(c2)C(=O)N(CCCN)C(c2ccc(C#N)cc2)C3)cc1] | (+) 1-[(3R)-2-(3-aminopropyl)-3-(4-cyanophenyl)-1-oxo-1,2,3,4-tetrahydroisoquinolin-7-yl]-3-[4-(methylsulfinyl)phenyl]urea | 10.6 nM (0.94) |

TABLE 4-continued

| Compound number | Structure | IUPAC name | FPR2 EC50 (% eff) |
|---|---|---|---|
| 42 | 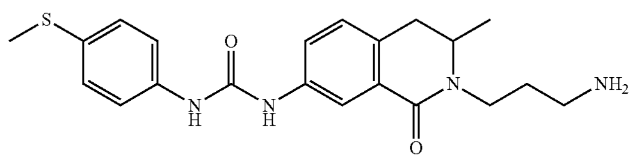 [SMILES: CSc1ccc(NC(=O)Nc2ccc3c(c2)C(=O)N(CCCN)C(C)C3)cc1] | 1-[2-(3-aminopropyl)-3-methyl-1-oxo-1,2,3,4-tetrahydroisoquinolin-7-yl]-3-[4-(methylsulfanyl)phenyl]urea | 15 nM (1.00) |
| 43 | 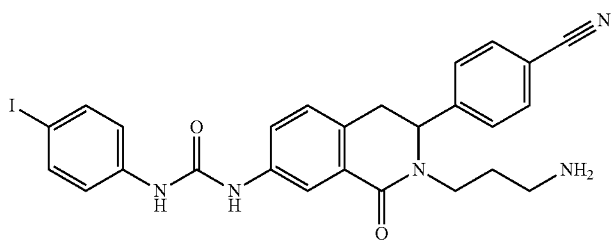 [SMILES: N#Cc1ccc(C2Cc3ccc(NC(=O)Nc4ccc(I)cc4)cc3C(=O)N2CCCN)cc1] | 1-[2-(3-aminopropyl)-3-(4-cyanophenyl)-1-oxo-1,2,3,4-tetrahydroisoquinolin-7-yl]-3-(4-iodophenyl)urea | 13.7 nM (0.94) |
| 44 | 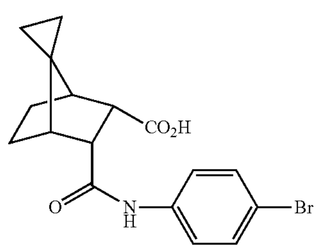 [SMILES: O=C(O)C1C(C(=O)Nc2ccc(Br)cc2)C2CCC1C21CC1] | (+) (2S,3R)-3-[(4-bromophenyl)carbamoyl]spiro[bicyclo[2.2.1]heptane-7,1'-cyclopropane]-2-carboxylic acid | <1 nM (0.98) |
| 45 | 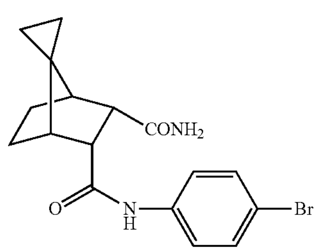 [SMILES: NC(=O)C1C(C(=O)Nc2ccc(Br)cc2)C2CCC1C21CC1] | (−) N-(4-bromophenyl)spiro[bicyclo[2.2.1]heptane-7,1'-cyclopropane]-2,3-dicarboxamide | <1 nM (0.91) |
| 46 | 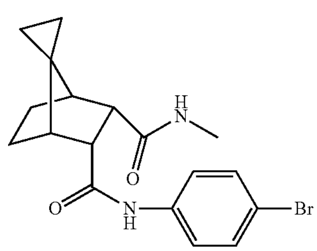 [SMILES: CNC(=O)C1C(C(=O)Nc2ccc(Br)cc2)C2CCC1C21CC1] | N-(4-bromophenyl)-N'-methylspiro[bicyclo[2.2.1]heptane-7,1'-cyclopropane]-2,3-dicarboxamide | 8.5 nM (1.0) |
| 47 | 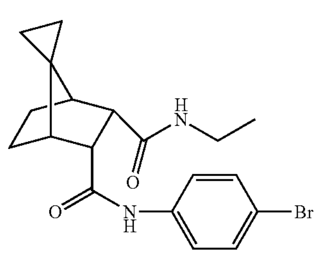 [SMILES: CCNC(=O)C1C(C(=O)Nc2ccc(Br)cc2)C2CCC1C21CC1] | N-(4-bromophenyl)-N'-ethylspiro[bicyclo[2.2.1]heptane-7,1'-cyclopropane]-2,3-dicarboxamide | 9.3 nM (1.0) |

TABLE 4-continued

| Compound number | Structure | IUPAC name | FPR2 EC50 (% eff) |
|---|---|---|---|
| 48 | 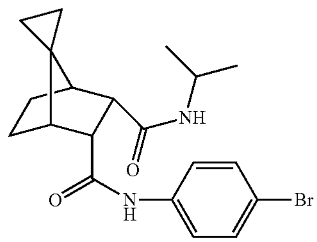 [SMILES: CC(C)NC(=O)C1C(C(=O)Nc2ccc(Br)cc2)C2CCC1C21CC1] | N-(4-bromophenyl)-N'-(propan-2-yl)spiro[bicyclo[2.2.1]heptane-7,1'-cyclopropane]-2,3-dicarboxamide | 6.7 nM (1.0) |
| 49 | 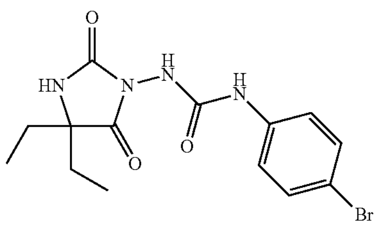 [SMILES: CCC1(CC)NC(=O)N(NC(=O)Nc2ccc(Br)cc2)C1=O] | 1-(4-bromophenyl)-3-(4,4-diethyl-2,5-dioxoimidazolidin-1-yl)urea | 11.5 nM (0.98) |
| 50 | 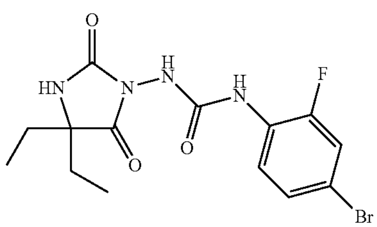 [SMILES: CCC1(CC)NC(=O)N(NC(=O)Nc2ccc(Br)cc2F)C1=O] | 1-(4-bromo-2-fluorophenyl)-3-(4,4-diethyl-2,5-dioxoimidazolidin-1-yl)urea | 15.7 nM (1.0) |
| 51 | 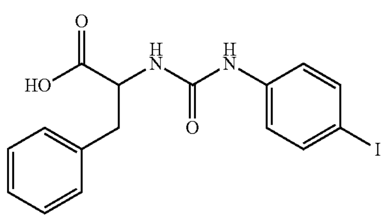 [SMILES: O=C(Nc1ccc(I)cc1)NC(Cc1ccccc1)C(=O)O] | (2S)-2-{[(4-iodophenyl)carbamoyl]amino}-3-phenylpropanoic acid | 14.5 nM (1.0) |
| 52 | 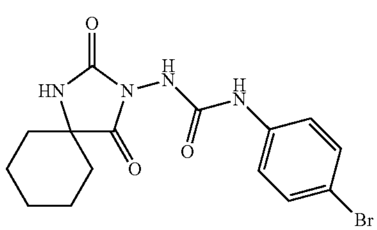 [SMILES: O=C(Nc1ccc(Br)cc1)NN1C(=O)NC2(CCCCC2)C1=O] | 1-(4-bromophenyl)-3-(2,4-dioxo-1,3-diazaspiro[4.5]dec-3-yl)urea | 15.1 nM (1.0) |
| 53 | 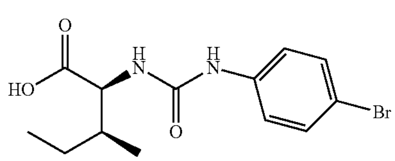 [SMILES: CC[C@H](C)[C@H](NC(=O)Nc1ccc(Br)cc1)C(=O)O] | (2S,3S)-2-{[(4-bromophenyl)carbamoyl]amino}-3-methylpentanoic acid | 12.9 nM (0.9) |
| 54 | 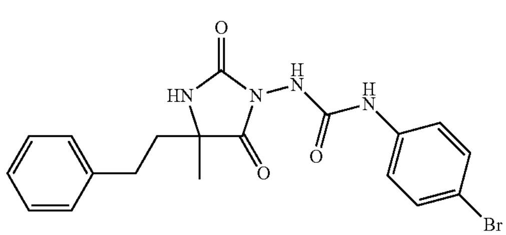 [SMILES: CC1(CCc2ccccc2)NC(=O)N(NC(=O)Nc2ccc(Br)cc2)C1=O] | 1-(4-bromophenyl)-3-[4-methyl-2,5-dioxo-4-(2-phenylethyl)imidazolidin-1-yl]urea | 5.1 nM (0.87) |

TABLE 4-continued

| Compound number | Structure | IUPAC name | FPR2 EC50 (% eff) |
|---|---|---|---|
| 55 | 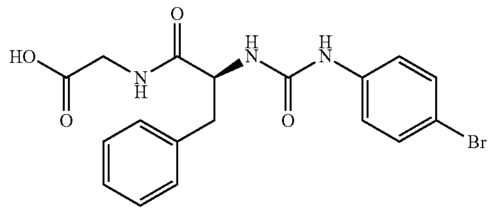 [SMILES: O=C(O)CNC(=O)[C@H](Cc1ccccc1)NC(=O)Nc1ccc(Br)cc1] | {[(2S)-2-{[(4-bromophenyl)carbamoyl]amino}-3-phenylpropanoyl]amino} acetic acid | 7.7 nM (0.99) |
| 56 | 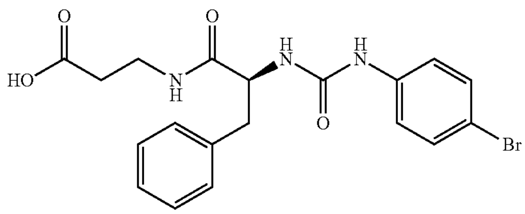 [SMILES: O=C(O)CCNC(=O)[C@H](Cc1ccccc1)NC(=O)Nc1ccc(Br)cc1] | 3-{[(2S)-2-{[(4-bromophenyl)carbamoyl]amino}-3-phenylpropanoyl]amino} propanoic acid | 18 nM (0.98) |
| 57 | 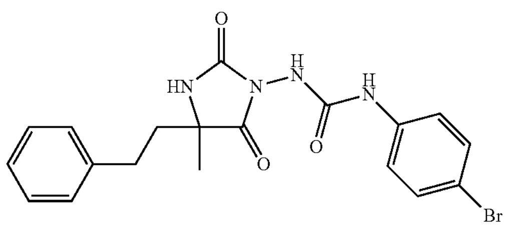 [SMILES: CC1(CCc2ccccc2)NC(=O)N(NC(=O)Nc2ccc(Br)cc2)C1=O] | (+) 1-(4-bromophenyl)-3-[4-methyl-2,5-dioxo-4-(2-phenylethyl)imidazolidin-1-yl]urea | 3.2 nM (0.93) |
| 58 | 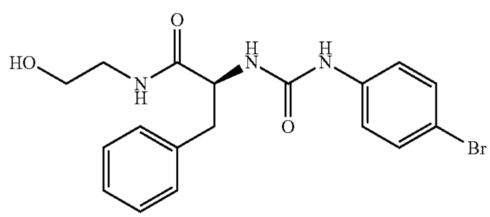 [SMILES: O=C(Nc1ccc(Br)cc1)N[C@@H](Cc1ccccc1)C(=O)NCCO] | (2S)-2-{[(4-bromophenyl)carbamoyl]amino}-N-(2-hydroxyethyl)-3-phenylpropanamide | 7.0 nM (0.86) |
| 59 | 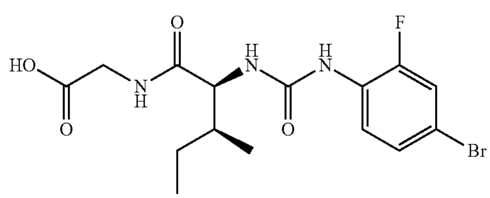 [SMILES: CC[C@H](C)[C@H](NC(=O)Nc1ccc(Br)cc1F)C(=O)NCC(=O)O] | {[(2S,3S)-2-{[(4-bromo-2-fluorophenyl)carbamoyl]amino}-3-methylpentanoyl]amino} acetic acid | 5.5 nM (0.95) |
| 60 | 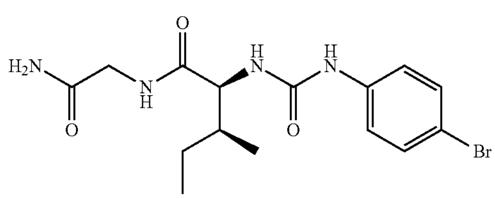 [SMILES: CC[C@H](C)[C@H](NC(=O)Nc1ccc(Br)cc1)C(=O)NCC(N)=O] | (2S,3S)-N-(2-amino-2-oxoethyl)-2-{[(4-bromophenyl)carbamoyl]amino}-3-methylpentanamide | 4.6 nM (0.91) |
| 61 | 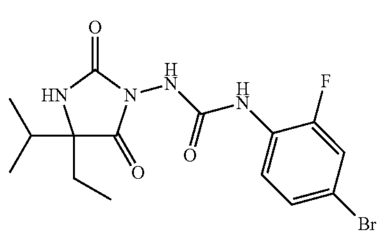 [SMILES: CCC1(C(C)C)NC(=O)N(NC(=O)Nc2ccc(Br)cc2F)C1=O] | 1-(4-bromo-2-fluorophenyl)-3-[4-ethyl-2,5-dioxo-4-(propan-2-yl)imidazolidin-1-yl]urea | 9.2 nM (0.97) |

TABLE 4-continued

| Compound number | Structure | IUPAC name | FPR2 EC50 (% eff) |
|---|---|---|---|
| 62 | 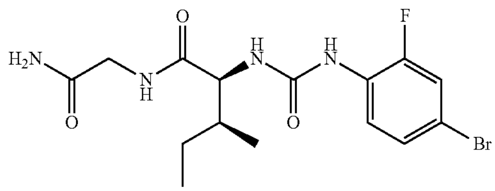 [SMILES: CC[C@H](C)[C@H](NC(=O)Nc1ccc(Br)cc1F)C(=O)NCC(N)=O] | (2S,3S)-N-(2-amino-2-oxoethyl)-2-{[(4-bromo-2-fluorophenyl)carbamoyl]amino}-3-methylpentanamide | 10.3 nM (1.0) |
| 63 | 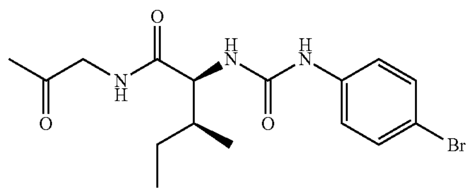 [SMILES: CC[C@H](C)[C@H](NC(=O)Nc1ccc(Br)cc1)C(=O)NCC(C)=O] | (2S,3S)-2-{[(4-bromophenyl)carbamoyl]amino}-3-methyl-N-(2-oxopropyl)pentanamide | 10.5 nM (0.97) |
| 64 | 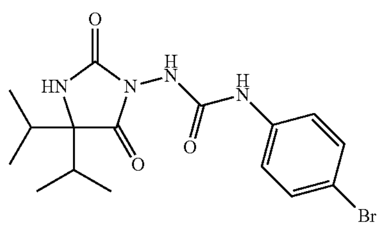 [SMILES: CC(C)C1(C(C)C)NC(=O)N(NC(=O)Nc2ccc(Br)cc2)C1=O] | 1-(4-bromophenyl)-3-[2,5-dioxo-4,4-di(propan-2-yl)imidazolidin-1-yl]urea | 3.8 nM (1.0) |
| 65 | 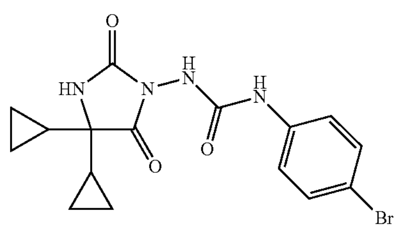 [SMILES: O=C(Nc1ccc(Br)cc1)NN1C(=O)NC(C2CC2)(C2CC2)C1=O] | 1-(4-bromophenyl)-3-(4,4-dicyclopropyl-2,5-dioxoimidazolidin-1-yl)urea | 14.3 nM (1.0) |
| 66 | 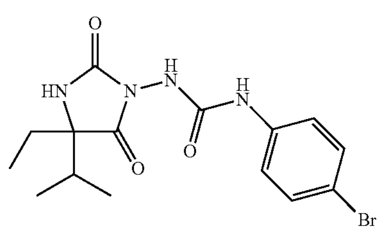 [SMILES: CCC1(C(C)C)NC(=O)N(NC(=O)Nc2ccc(Br)cc2)C1=O] | (+)1-(4-bromophenyl)-3-[4-ethyl-2,5-dioxo-4-(propan-2-yl)imidazolidin-1-yl]urea | 4.3 nM (0.96) |
| 67 | 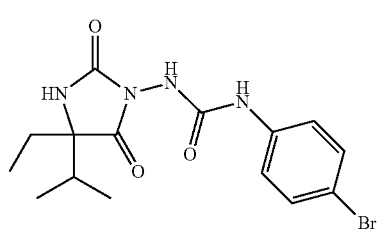 [SMILES: CCC1(C(C)C)NC(=O)N(NC(=O)Nc2ccc(Br)cc2)C1=O] | (−)1-(4-bromophenyl)-3[4-ethyl-2,5-dioxo-4-(propan-2-yl)imidazolidin-1-yl]urea | 3.3 nM (1.0) |
| 68 | 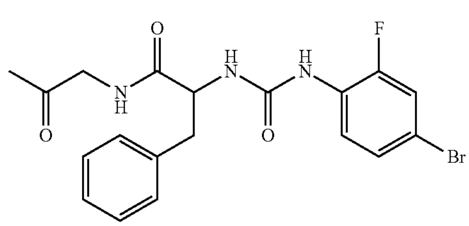 [SMILES: CC(=O)CNC(=O)C(Cc1ccccc1)NC(=O)Nc1ccc(Br)cc1F] | (2S)-2-{[(4-bromo-2-fluorophenyl)carbamoyl]amino}-N-(2-oxopropyl)-3-phenylpropanamide | 12.4 nM (0.94) |

TABLE 4-continued

| Compound number | Structure | IUPAC name | FPR2 EC50 (% eff) |
|---|---|---|---|
| 69 | 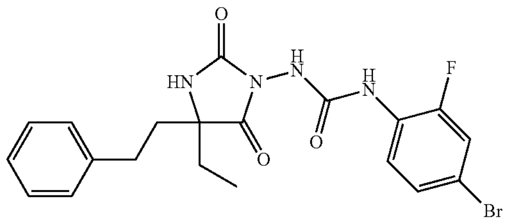 [SMILES: CCC1(CCc2ccccc2)NC(=O)N(NC(=O)Nc2ccc(Br)cc2F)C1=O] | 1-(4-bromo-2-fluorophenyl)-3-[4-ethyl-2,5-dioxo-4-(2-phenylethyl)imidazolidin-1-yl]urea | 13.4 nM (0.91) |
| 70 | 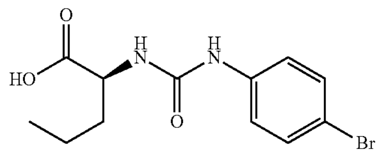 [SMILES: CCC[C@H](NC(=O)Nc1ccc(Br)cc1)C(=O)O] | (2S)-2-{[(4-bromophenyl)carbamoyl]amino}pentanoic acid | 7.1 nM (1.0) |
| 71 | 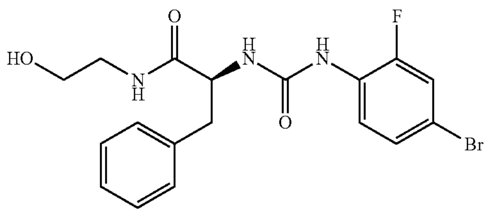 [SMILES: O=C(Nc1ccc(Br)cc1F)N[C@@H](Cc1ccccc1)C(=O)NCCO] | (2S)-2-{[(4-bromo-2-fluorophenyl)carbamoyl]amino}-N-(2-hydroxyethyl)-3-phenylpropanamide | 15.6 nM (0.98) |
| 72 | 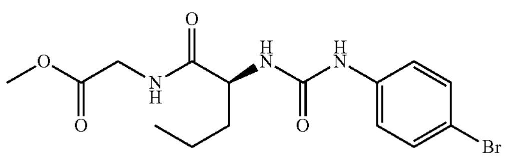 [SMILES: CCC[C@H](NC(=O)Nc1ccc(Br)cc1)C(=O)NCC(=O)OC] | methyl {[(2S)-2-{[(4-bromophenyl)carbamoyl]amino}pentanoyl]amino}acetate | 16.4 nM (0.86) |
| 73 | 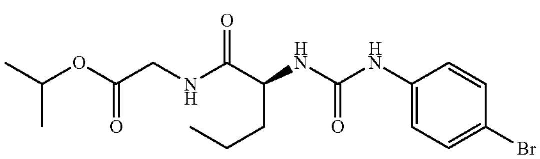 [SMILES: CCC[C@H](NC(=O)Nc1ccc(Br)cc1)C(=O)NCC(=O)OC(C)C] | propan-2-yl {[(2S)-2-{[(4-bromophenyl)carbamoyl]amino}pentanoyl]amino}acetate | 14.5 nM (1.0) |
| 74 | 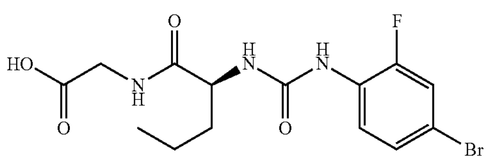 [SMILES: CCC[C@H](NC(=O)Nc1ccc(Br)cc1F)C(=O)NCC(=O)O] | {[(2S)-2-{[(4-bromo-2-fluorophenyl)carbamoyl]amino}pentanoyl]amino}acetic acid | 4.1 nM (0.91) |
| 75 | 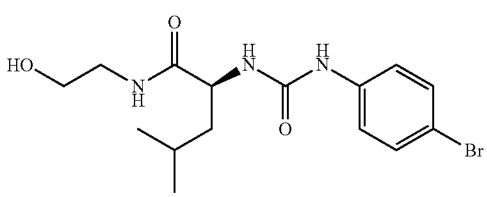 [SMILES: CC(C)C[C@H](NC(=O)Nc1ccc(Br)cc1)C(=O)NCCO] | (2S)-2-{[(4-bromophenyl)carbamoyl]amino}-N-(2-hydroxyethyl)-4-methylpentanamide | 13.5 nM (0.76) |
| 76 | 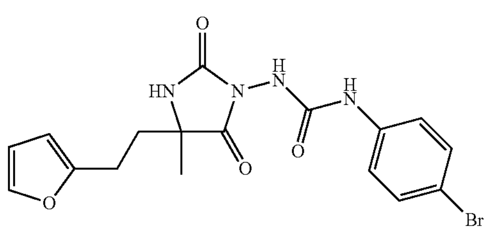 | 1-(4-bromophenyl)-3-{4-[2-(furan-2-yl)ethyl]-4-methyl-2,5-dioxoimidazolidin-1-yl}urea | 5.2 nM (0.99) |

TABLE 4-continued

| Compound number | Structure | IUPAC name | FPR2 EC50 (% eff) |
|---|---|---|---|
| 77 | 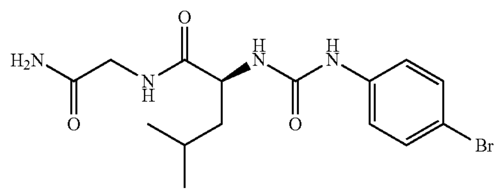 [SMILES: CC(C)C[C@H](NC(=O)Nc1ccc(Br)cc1)C(=O)NCC(N)=O] | (2S)-N-(2-amino-2-oxoethyl)-2-{[(4-bromophenyl)carbamoyl]amino}-4-methylpentanamide | 1.1 nM (1.0) |
| 78 | 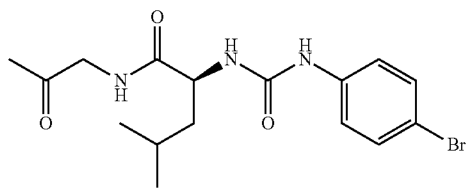 [SMILES: CC(=O)CNC(=O)[C@H](CC(C)C)NC(=O)Nc1ccc(Br)cc1] | (2S)-2-{[(4-bromophenyl)carbamoyl]amino}-4-methyl-N-(2-oxopropyl)pentanamide | 4.7 nM (0.82) |
| 79 | 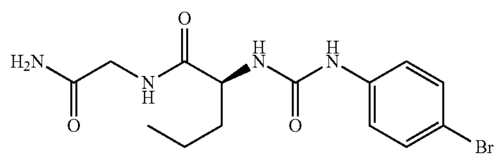 [SMILES: CCC[C@H](NC(=O)Nc1ccc(Br)cc1)C(=O)NCC(N)=O] | (2S)-N-(2-amino-2-oxoethyl)-2-{[(4-bromophenyl)carbamoyl]amino}pentanamide | 2.5 nM (0.97) |
| 80 | 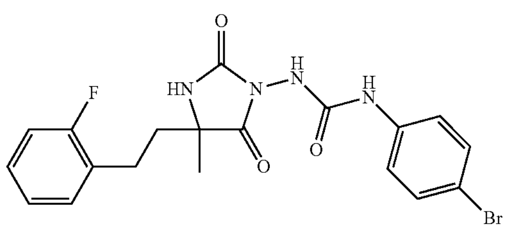 [SMILES: CC1(CCc2ccccc2F)NC(=O)N(NC(=O)Nc2ccc(Br)cc2)C1=O] | 1-(4-bromophenyl)-3-{4-[2-(2-fluorophenyl)ethyl]-4-methyl-2,5-dioxoimidazolidin-1-yl}urea | 14.3 nM (99) |
| 81 | 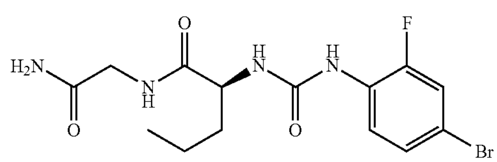 [SMILES: CCC[C@H](NC(=O)Nc1ccc(Br)cc1F)C(=O)NCC(N)=O] | (2S)-N-(2-amino-2-oxoethyl)-2-{[(4-bromo-2-fluorophenyl)carbamoyl]amino}pentanamide | 5.2 nM (0.96) |
| 82 | 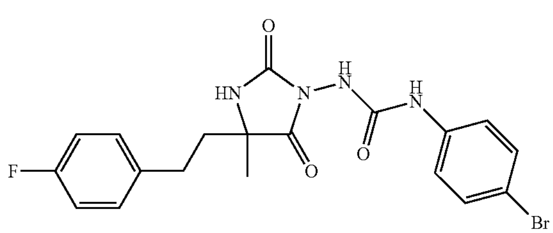 [SMILES: CC1(CCc2ccc(F)cc2)NC(=O)N(NC(=O)Nc2ccc(Br)cc2)C1=O] | 1-(4-bromophenyl)-3-{4-[2-(4-fluorophenyl)ethyl]-4-methyl-2,5-dioxoimidazolidin-1-yl}urea | 16.3 nM (1.0) |
| 83 | 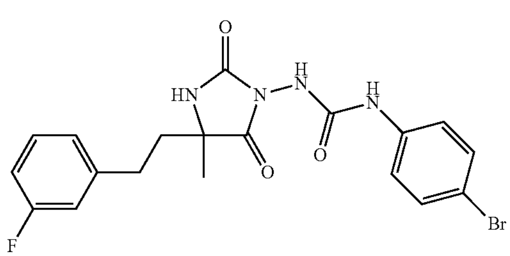 [SMILES: CC1(CCc2cccc(F)c2)NC(=O)N(NC(=O)Nc2ccc(Br)cc2)C1=O] | 1-(4-bromophenyl)-3-{4-[2-(3-fluorophenyl)ethyl]-4-methyl-2,5-dioxoimidazolidin-1-yl}urea | 11.1 nM (1.0) |

TABLE 4-continued

| Compound number | Structure | IUPAC name | FPR2 EC50 (% eff) |
|---|---|---|---|
| 84 | 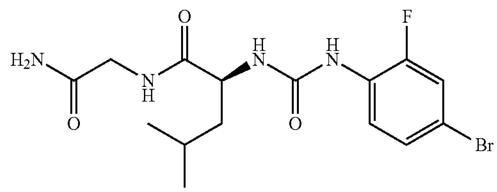 [SMILES: CC(C)C[C@H](NC(=O)Nc1ccc(Br)cc1F)C(=O)NCC(N)=O] | (2S)-N-(2-amino-2-oxoethyl)-2-{[(4-bromo-2-fluorophenyl)carbamoyl]amino}-4-methylpentanamide | 4.5 nM (0.95) |
| 85 | 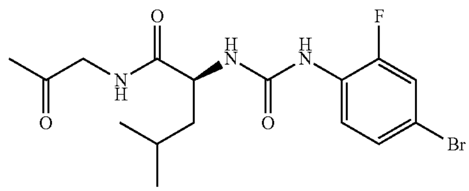 [SMILES: CC(=O)CNC(=O)[C@H](CC(C)C)NC(=O)Nc1ccc(Br)cc1F] | (2S)-2-{[(4-bromo-2-fluorophenyl)carbamoyl]amino}-4-methyl-N-(2-oxopropyl)pentanamide | 20 nM (0.99) |
| 86 | 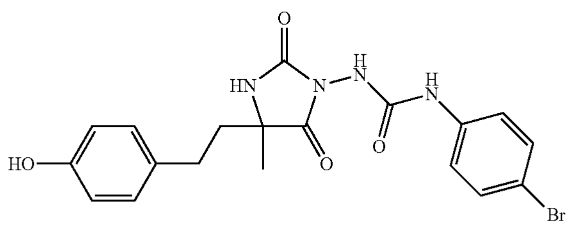 [SMILES: CC1(CCc2ccc(O)cc2)NC(=O)N(NC(=O)Nc2ccc(Br)cc2)C1=O] | 1-(4-bromophenyl)-3-{4-[2-(4-hydroxyphenyl)ethyl]-4-methyl-2,5-dioxoimidazolidin-1-yl}urea | 13.3 nM (1.0) |
| 87 | 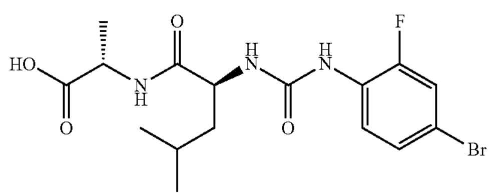 [SMILES: CC(C)C[C@H](NC(=O)Nc1ccc(Br)cc1F)C(=O)N[C@@H](C)C(=O)O] | (2S)-2-{[(2S)-2-{[(4-bromo-2-fluorophenyl)carbamoyl]amino}-4-methylpentanoyl]amino}propanoic acid | 12.1 nM (0.95) |
| 88 | 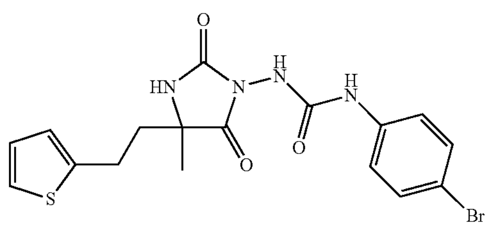 [SMILES: CC1(CCc2cccs2)NC(=O)N(NC(=O)Nc2ccc(Br)cc2)C1=O] | 1-(4-bromophenyl)-3-{4-methyl-2,5-dioxo-4-[2-(thiophen-2-yl)ethyl]imidazolidin-1-yl}urea | 7.9 nM (0.94) |
| 89 | 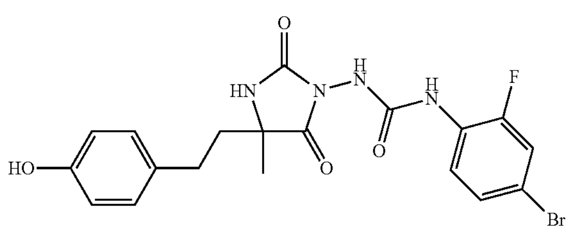 [SMILES: CC1(CCc2ccc(O)cc2)NC(=O)N(NC(=O)Nc2ccc(Br)cc2F)C1=O] | 1-(4-bromo-2-fluorophenyl)-3-{4-[2-(4-hydroxyphenyl)ethyl]-4-methyl-2,5-dioxoimidazolidin-1-yl}urea | 8.7 nM (0.85) |
| 90 | 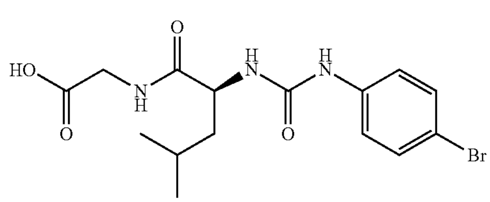 [SMILES: CC(C)C[C@H](NC(=O)Nc1ccc(Br)cc1)C(=O)NCC(=O)O] | (2S)-2-{[(2S)-2-{[(4-bromophenyl)carbamoyl]amino}-4-methylpentanoyl]amino}propanoic acid | 11.6 nM (1.0) |

TABLE 4-continued

| Compound number | Structure | IUPAC name | FPR2 EC50 (% eff) |
|---|---|---|---|
| 91 | 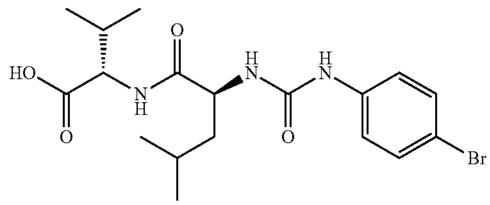 [SMILES: CC(C)C[C@H](NC(=O)Nc1ccc(Br)cc1)C(=O)N[C@H](C(=O)O)C(C)C] | (2S)-2-{[(2S)-2-{[(4-bromophenyl)carbamoyl]amino}-4-methylpentanoyl]amino}-3-methylbutanoic acid | 1.7 nM (0.97) |
| 92 | 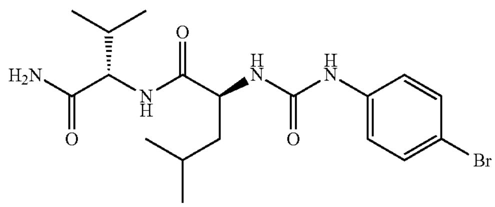 | (2S)-N-[(2S)-1-amino-3-methyl-1-oxobutan-2-yl]-2-{[(4-bromophenyl)carbamoyl]amino}-4-methylpentanamide | 5.8 nM (1.0) |
| 93 | 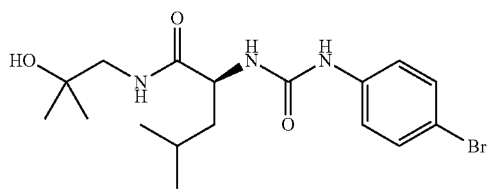 [SMILES: CC(C)C[C@H](NC(=O)Nc1ccc(Br)cc1)C(=O)NCC(C)(C)O] | (2S)-2-{[(4-bromophenyl)carbamoyl]amino}-N-(2-hydroxy-2-methylpropyl)-4-methylpentanamide | 2.5 nM (0.93) |
| 94 | 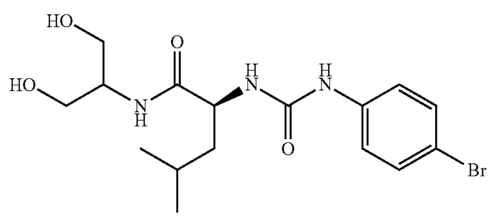 [SMILES: CC(C)C[C@H](NC(=O)Nc1ccc(Br)cc1)C(=O)NC(CO)CO] | (2S)-2-{[(4-bromophenyl)carbamoyl]amino}-N-(1,3-dihydroxypropan-2-yl)-4-methylpentanamide | 7.4 nM (0.96) |
| 95 | 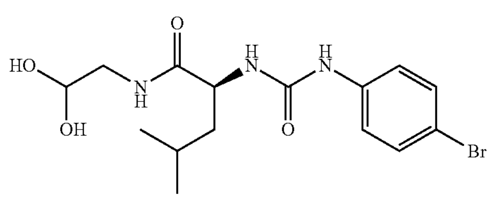 [SMILES: CC(C)C[C@H](NC(=O)Nc1ccc(Br)cc1)C(=O)NCC(O)O] | (2S)-2-{[(4-bromophenyl)carbamoyl]amino}-N-(2,3-dihydroxypropyl)-4-methylpentanamide | 5.1 nM (0.98) |
| 96 | 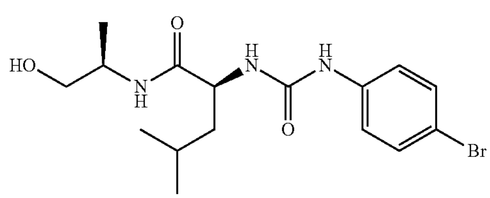 [SMILES: CC(C)C[C@H](NC(=O)Nc1ccc(Br)cc1)C(=O)N[C@H](C)CO] | (2S)-2-{[(4-bromophenyl)carbamoyl]amino}-N-[(2R)-1-hydroxypropan-2-yl]-4-methylpentanamide | 3.0 nM (1.0) |
| 97 | 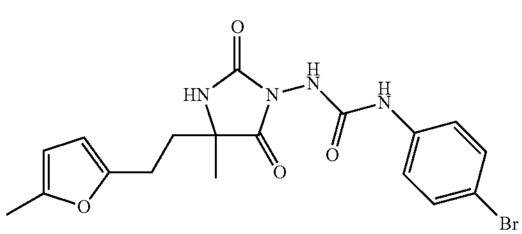 [SMILES: Cc1ccc(CCC2(C)NC(=O)N(NC(=O)Nc3ccc(Br)cc3)C2=O)o1] | 1-(4-bromophenyl)-3-{4-methyl-4-[2-(5-methylfuran-2-yl)ethyl]-2,5-dioxoimidazolidin-1-yl}urea | 3.5 nM (0.95) |

TABLE 4-continued

| Compound number | Structure | IUPAC name | FPR2 EC50 (% eff) |
|---|---|---|---|
| 98 | 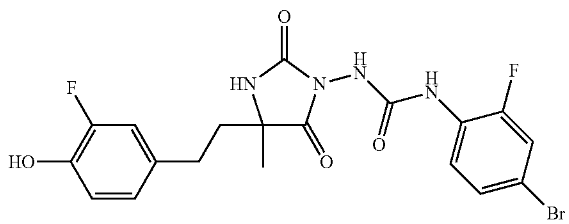 [SMILES: CC1(CCc2ccc(O)c(F)c2)NC(=O)N(NC(=O)Nc2ccc(Br)cc2F)C1=O] | 1-(4-bromo-2-fluorophenyl)-3-{4-[2-(3-fluoro-4-hydroxyphenyl)ethyl]-4-methyl-2,5-dioxoimidazolidin-1-yl}urea | 7.4 nM (0.91) |
| 99 | 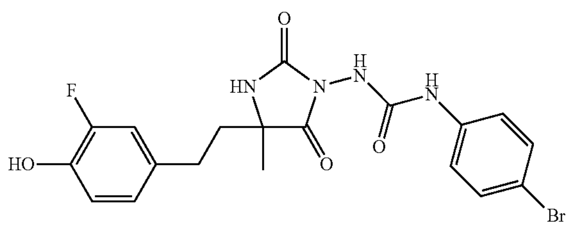 [SMILES: CC1(CCc2ccc(O)c(F)c2)NC(=O)N(NC(=O)Nc2ccc(Br)cc2)C1=O] | 1-(4-bromophenyl)-3-{4-[2-(3-fluoro-4-hydroxyphenyl)ethyl]-4-methyl-2,5-dioxoimidazolidin-1-yl}urea | 8.0 nM (1.0) |
| 100 | 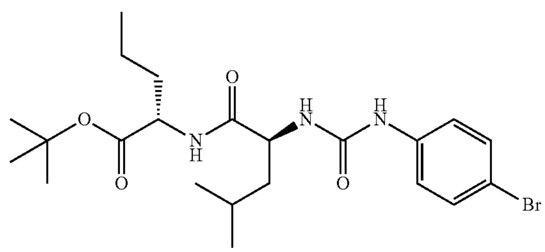 [SMILES: CCC[C@H](NC(=O)[C@H](CC(C)C)NC(=O)Nc1ccc(Br)cc1)C(=O)OC(C)(C)C] | tert-butyl (2S)-2-{[(2S)-2-{[(4-bromophenyl)carbamoyl]amino}-4-methylpentanoyl]amino}pentanoate | 13.0 nM (1.0) |
| 101 | 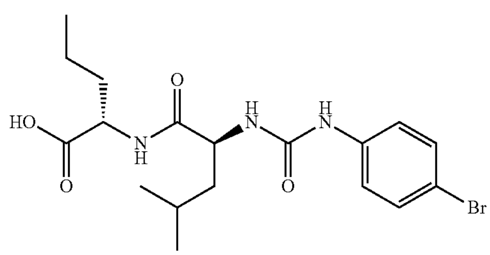 [SMILES: CCC[C@H](NC(=O)[C@H](CC(C)C)NC(=O)Nc1ccc(Br)cc1)C(=O)O] | (2S)-2-{[(2S)-2-{[(4-bromophenyl)carbamoyl]amino}-4-methylpentanoyl]amino}pentanoic acid | 1.0 nM (0.95) |
| 102 | 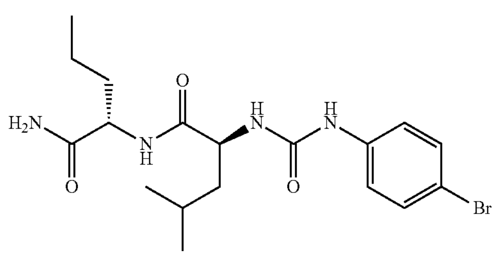 [SMILES: CCC[C@H](NC(=O)[C@H](CC(C)C)NC(=O)Nc1ccc(Br)cc1)C(N)=O] | (2S)-N-[(2S)-1-amino-1-oxopentan-2-yl]-2-{[(4-bromophenyl)carbamoyl]amino}-4-methylpentanamide | 7.3 nM (0.99) |
| 103 | 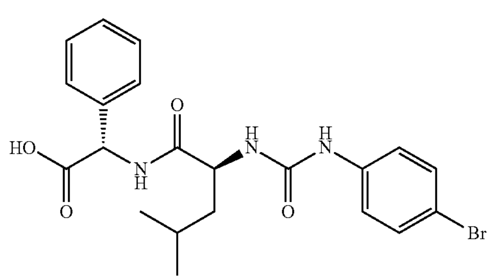 [SMILES: CC(C)C[C@H](NC(=O)Nc1ccc(Br)cc1)C(=O)N[C@H](C(=O)O)c1ccccc1] | (2S)-{[(2S)-2-{[(4-bromophenyl)carbamoyl]amino}-4-methylpentanoyl]amino}(phenyl)ethanoic acid | 9.1 nM (1.0) |

TABLE 4-continued

| Compound number | Structure | IUPAC name | FPR2 EC50 (% eff) |
|---|---|---|---|
| 104 | 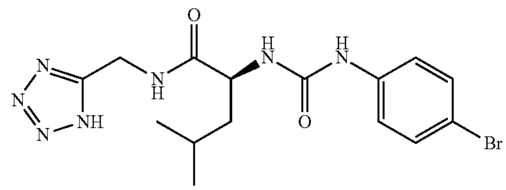 [SMILES: CC(C)C[C@H](NC(=O)Nc1ccc(Br)cc1)C(=O)NCc1nnn[nH]1] | (2S)-2-{[(4-bromophenyl)carbamoyl]amino}-4-methyl-N-(1H-tetrazol-5-ylmethyl)pentanamide | 2.3 nM (0.81) |
| 105 | 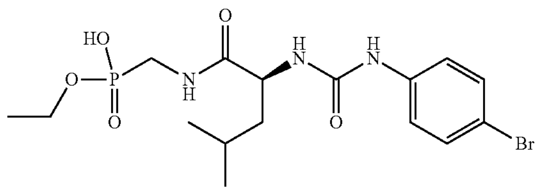 [SMILES: CCOP(=O)(O)CNC(=O)[C@H](CC(C)C)NC(=O)Nc1ccc(Br)cc1] | ethyl hydrogen ({[(2S)-2-{[(4-bromophenyl)carbamoyl]amino}-4-methylpentanoyl]amino}methyl)phosphonate | 0.95 nM (0.88) |
| 106 | 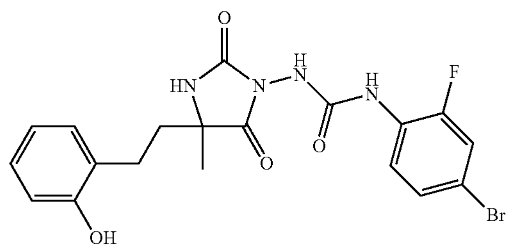 [SMILES: CC1(CCc2ccccc2O)NC(=O)N(NC(=O)Nc2ccc(Br)cc2F)C1=O] | 1-(4-bromo-2-fluorophenyl)-3-[4-[2-[2-hydroxyphenyl)ethyl]-4-methyl-2,5-dioxoimidazolidin-1-yl}urea | 4.0 nM (0.91) |
| 107 | 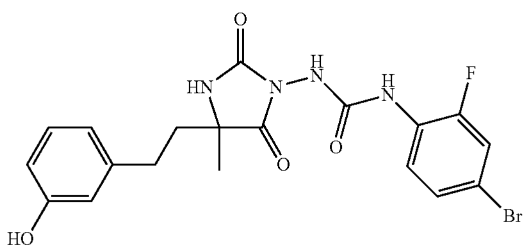 [SMILES: CC1(CCc2cccc(O)c2)NC(=O)N(NC(=O)Nc2ccc(Br)cc2F)C1=O] | 1-(4-bromo-2-fluorophenyl)-3-{4-[2-(3-hydroxyphenyl)ethyl]-4-methyl-2,5-dioxoimidazolidin-1-yl}urea | 2.2 nM (0.79) |
| 108 | 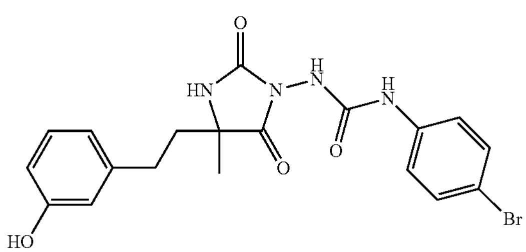 [SMILES: CC1(CCc2cccc(O)c2)NC(=O)N(NC(=O)Nc2ccc(Br)cc2)C1=O] | 1-(4-bromophenyl)-3-{4-[2-(3-hydroxyphenyl)ethyl]-4-methyl-2,5-dioxoimidazolidin-1-yl}urea | 2.1 nM (1.0) |
| 109 | 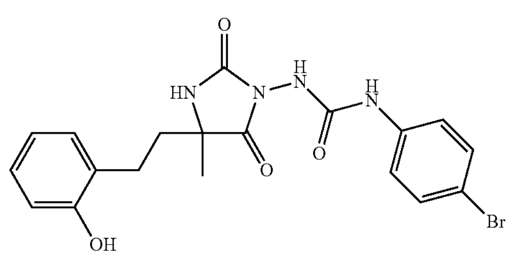 [SMILES: CC1(CCc2ccccc2O)NC(=O)N(NC(=O)Nc2ccc(Br)cc2)C1=O] | 1-(4-bromophenyl)-3-{4-[2-(2-hydroxyphenyl)ethyl]-4-methyl-2,5-dioxoimidazolidin-1-yl}urea | 0.97 nM (0.93) |

TABLE 4-continued

| Compound number | Structure | IUPAC name | FPR2 EC50 (% eff) |
|---|---|---|---|
| 110 | 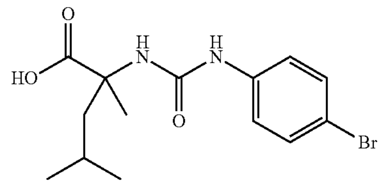 [SMILES: CC(C)CC(C)(NC(=O)Nc1ccc(Br)cc1)C(=O)O] | 2-{[(4-bromophenyl)carbamoyl]amino}-2,4-dimethylpentanoic acid | 19.4 nM (0.98) |
| 111 | 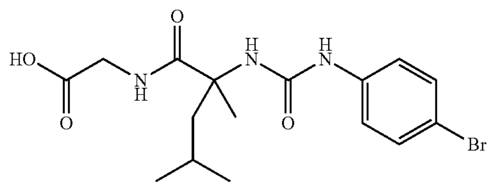 [SMILES: CC(C)CC(C)(NC(=O)Nc1ccc(Br)cc1)C(=O)NCC(=O)O] | [(2-{[(4-bromophenyl)carbamoyl]amino}-2,4-dimethylpentanoyl)amino]acetic acid | 19.1 nM (0.99) |
| 112 | 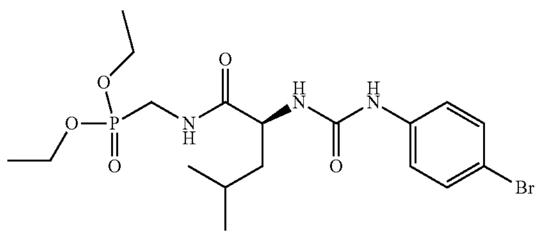 [SMILES: CCOP(=O)(CNC(=O)[C@H](CC(C)C)NC(=O)Nc1ccc(Br)cc1)OCC] | diethyl ({[(2S)-2-{[(4-bromophenyl)carbamoyl]amino}4-methylpentanoyl]amino}methyl)phosphonate | 0.48 nM (0.95) |
| 113 | 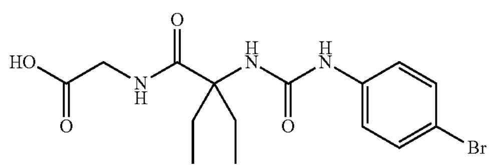 [SMILES: CCC(CC)(NC(=O)Nc1ccc(Br)cc1)C(=O)NCC(=O)O] | (2-{[(4-bromophenyl)carbamoyl]amino}-2-ethylbutanoyl)amino]acetic acid | 18.7 nM (1.0) |
| 114 | 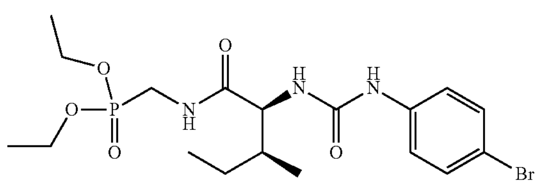 [SMILES: CCOP(=O)(CNC(=O)[C@@H](NC(=O)Nc1ccc(Br)cc1)[C@@H](C)CC)OCC] | diethyl ({[(2S,3S)-2-{[(4-bromophenyl)carbamoyl]amino}-3-methylpentanoyl]amino}methyl)phosphonate | 2.9 nM (1.0) |
| 115 | 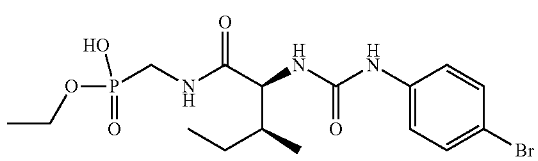 [SMILES: CCOP(=O)(O)CNC(=O)[C@@H](NC(=O)Nc1ccc(Br)cc1)[C@@H](C)CC] | ethyl hydrogen ({[(2S,3S)-2-{[(4-bromophenyl)carbamoyl]amino}3-methylpentanoyl]amino}methyl)phosphonate | 2.7 nM (0.88) |
| 116 | 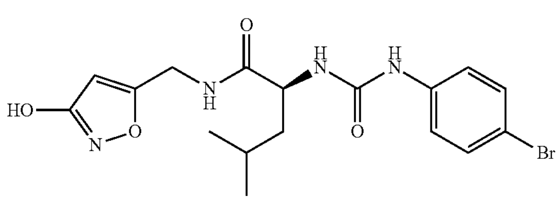 [SMILES: CC(C)C[C@H](NC(=O)Nc1ccc(Br)cc1)C(=O)NCc1cc(O)no1] | (2S)-2-{[(4-bromophenyl)carbamoyl]amino}-N-[(3-hydroxy-1,2-oxazol-5-yl)methyl]-4-methylpentanamide | 12.0 nM (1.0) |
| 117 | 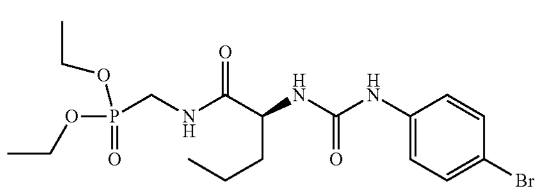 [SMILES: CCC[C@H](NC(=O)Nc1ccc(Br)cc1)C(=O)NCP(=O)(OCC)OCC] | diethyl ({[(2S)-2-{[(4-bromophenyl)carbamoyl]amino}pentanoyl]amino}methy)phosphonate | 0.27 nM (1.0) |

TABLE 4-continued

| Compound number | Structure | IUPAC name | FPR2 EC50 (% eff) |
|---|---|---|---|
| 118 | 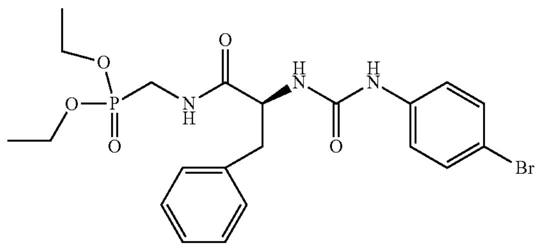 [SMILES: CCOP(=O)(CNC(=O)[C@H](Cc1ccccc1)NC(=O)Nc1ccc(Br)cc1)OCC] | diethyl ({[(2S)-2-{[(4-bromophenyl)carbamoyl]amino}-3-phenylpropanoyl]amino}methyl)phosphonate | 16.1 nM (0.93) |
| 119 | 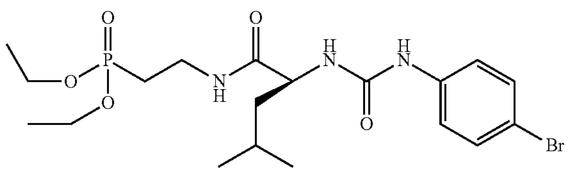 [SMILES: CCOP(=O)(CCNC(=O)[C@H](CC(C)C)NC(=O)Nc1ccc(Br)cc1)OCC] | diethyl (2-{[(2S)-2-{[(4-bromophenyl)carbamoyl]amino}-4-methylpentanoyl]amino}ethyl)phosphonate | 16.1 nM (0.97) |
| 120 | 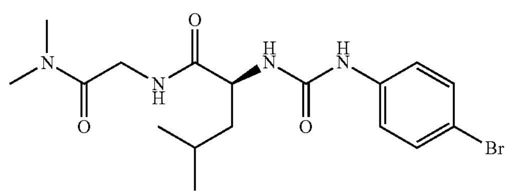 [SMILES: CC(C)C[C@H](NC(=O)Nc1ccc(Br)cc1)C(=O)NCC(=O)N(C)C] | (2S)-2-{[(4-bromophenyl)carbamoyl]amino}-N-[2-(dimethylamino)-2-oxoethyl]-4-methylpentanamide | 1.7 nM (0.99) |
| 121 | 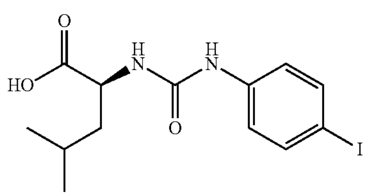 [SMILES: CC(C)C[C@H](NC(=O)Nc1ccc(I)cc1)C(=O)O] | (2S)-2-{[(4-iodophenyl)carbamoyl]amino}-4-methylpentanoic acid | 4.0 nM (0.93) |
| 122 | 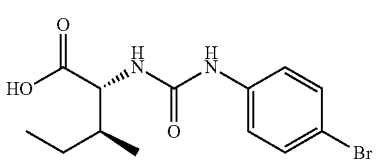 [SMILES: CC[C@H](C)[C@@H](NC(=O)Nc1ccc(Br)cc1)C(=O)O] | (2R,3R)-2-{[(4-bromophenyl)carbamoyl]amino}-3-methylpentanoic acid | 10 μM (0.59) |
| 123 | 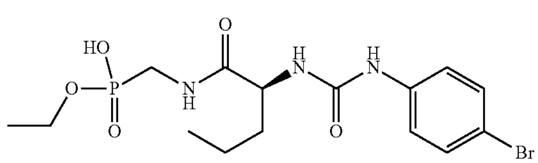 [SMILES: CCC[C@H](NC(=O)Nc1ccc(Br)cc1)C(=O)NCP(=O)(O)OCC] | ethyl hydrogen ({[(2S)-2-{[(4-bromophenyl)carbamoyl]amino}pentanoyl]amino}methyl)phosphonate | 1 nM (0.96) |
| 124 | 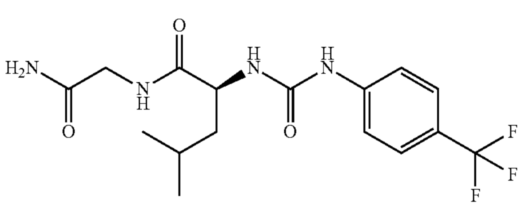 [SMILES: CC(C)C[C@H](NC(=O)Nc1ccc(C(F)(F)F)cc1)C(=O)NCC(N)=O] | {[(2S)-4-methyl-2-({[4-(trifluoromethyl)phenyl]carbamoyl}amino)pentanoyl]amino}acetic acid | 1.8 nM (1.0) |
| 125 | 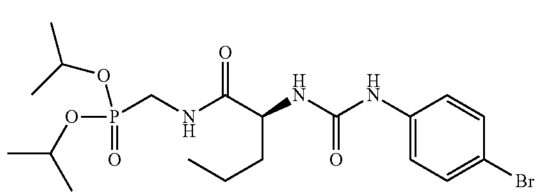 [SMILES: CCC[C@H](NC(=O)Nc1ccc(Br)cc1)C(=O)NCP(=O)(OC(C)C)OC(C)C] | dipropan-2-yl ({[(2S)-2-{[(4-bromophenyl)carbamoyl]amino}pentanoyl]amino}methyl)phosphonate | 1.2 nM (1.0) |

TABLE 4-continued

| Compound number | Structure | IUPAC name | FPR2 EC50 (% eff) |
|---|---|---|---|
| 126 | 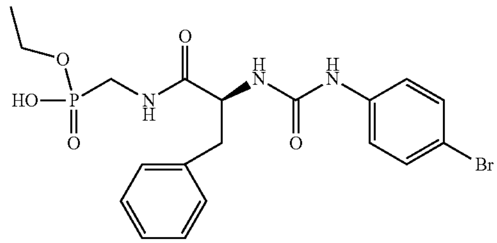 [SMILES: CCOP(=O)(O)CNC(=O)[C@H](Cc1ccccc1)NC(=O)Nc1ccc(Br)cc1] | ethyl hydrogen ({[(2S)-2-{[(4-bromophenyl)carbamoyl]amino}3-phenylpropanoyl]amino}methyl)phosphonate | 16.0 nM (1.0) |
| 127 | 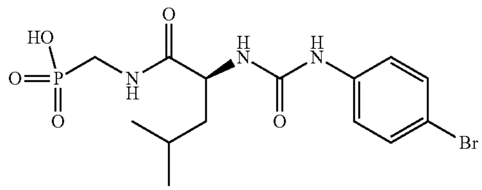 | {[(2S)-2-{[(4-bromophenyl)carbamoyl]amino}4-methylpentanoyl]amino}methanesulfonic acid | 2.0 nM (0.91) |
| 128 | 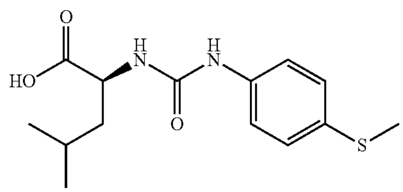 [SMILES: CSc1ccc(NC(=O)N[C@@H](CC(C)C)C(=O)O)cc1] | (2S)-4-methyl-2-({[4-(methylsulfanyl)phenyl]carbamoyl}amino)pentanoic acid | 16.8 nM (0.92) |
| 129 | 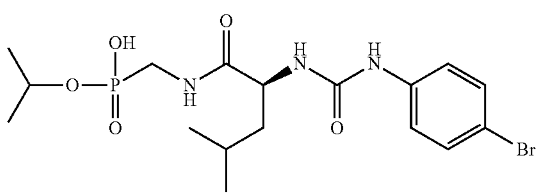 [SMILES: CC(C)C[C@H](NC(=O)Nc1ccc(Br)cc1)C(=O)NCP(=O)(O)OC(C)C] | propan-2-yl hydrogen {[(2-{[(4-bromophenyl)carbamoyl]amino}pentanoyl)amino]methyl}phosphonate | 1.87 nM (0.89) |
| 130 | 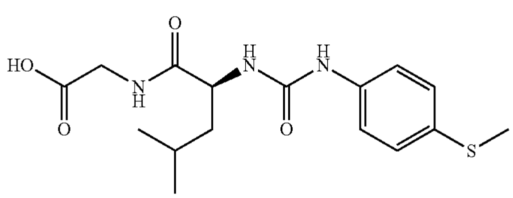 [SMILES: CSc1ccc(NC(=O)N[C@@H](CC(C)C)C(=O)NCC(=O)O)cc1] | {[(2S)-4-methyl-2-({[4-(methylsulfanyl)phenyl]carbamoyl}amino)pentanoyl]amino}acetic acid | 3.0 nM (1.0) |
| 131 | 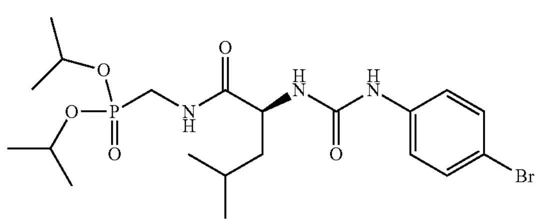 [SMILES: CC(C)C[C@H](NC(=O)Nc1ccc(Br)cc1)C(=O)NCP(=O)(OC(C)C)OC(C)C] | dipropan-2-yl({[(2S)-2-{[(4-bromophenyl)carbamoyl]amino}-4-methylpentanoyl]amino}methyl)phosphonate | 4.0 nM (1.0) |
| 132 | 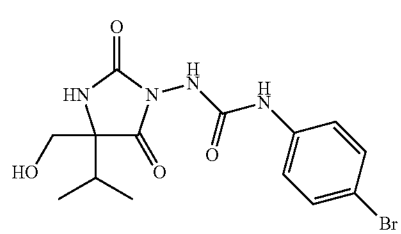 [SMILES: CC(C)C1(CO)NC(=O)N(NC(=O)Nc2ccc(Br)cc2)C1=O] | 1-(4-bromophenyl)-3[4-(hydroxymethyl)-2,5-dioxo-4-(propan-2-yl)imidazolidin-1-yl]urea | 16.2 nM (0.86) |

TABLE 4-continued

| Compound number | Structure | IUPAC name | FPR2 EC50 (% eff) |
|---|---|---|---|
| 133 | 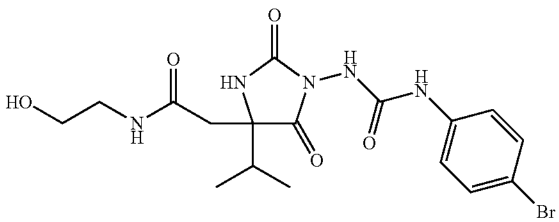 [SMILES: CC(C)C1(CC(=O)NCCO)NC(=O)N(NC(=O)Nc2ccc(Br)cc2)C1=O] | 2-[1-{[(4-bromophenyl)carbamoyl]amino}-2,5-dioxo-4-(propan-2-yl)imidazolidin-4-yl]-N-(2-hydroxyethyl)acetamide | 2.7 nM (1.0) |
| 134 | 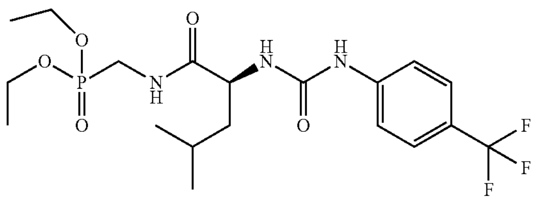 [SMILES: CCOP(=O)(CNC(=O)[C@H](CC(C)C)NC(=O)Nc1ccc(C(F)(F)F)cc1)OCC] | diethyl ({[(2S)-4-methyl-2-({[4-(trifluoromethyl)phenyl]carbamoyl}amino)pentanoyl]amino}methyl)phosphonate | 5.5 nM (0.97) |
| 135 | 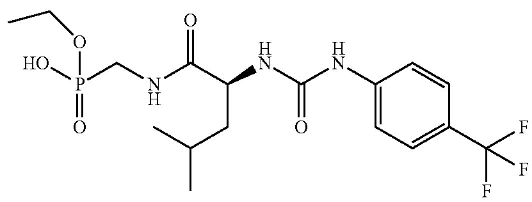 [SMILES: CCOP(=O)(O)CNC(=O)[C@H](CC(C)C)NC(=O)Nc1ccc(C(F)(F)F)cc1] | ethyl hydrogen ({[(2S)-4-methyl-2-({[4-(trifluoromethyl)phenyl]carbamoyl}amino)pentanoyl]amino}methyl)phosphonate | 1.9 nM (0.91) |
| 136 | 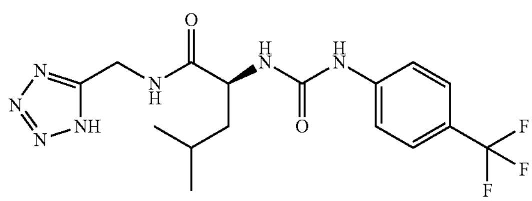 [SMILES: CC(C)C[C@H](NC(=O)Nc1ccc(C(F)(F)F)cc1)C(=O)NCc1nnn[nH]1] | (2S)-4-methyl-N-(1H-tetrazol-5-ylmethyl)-2-({[4-(trifluoromethyl)phenyl]carbamoyl}amino)pentanamide | 3.7 nM (0.96) |
| 237 | 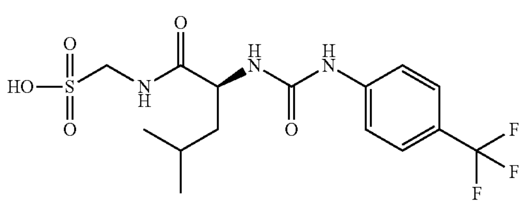 [SMILES: CC(C)C[C@H](NC(=O)Nc1ccc(C(F)(F)F)cc1)C(=O)NCS(=O)(=O)O] | {[(2S)-4-methyl-2-({[4-(trifluoromethyl)phenyl]carbamoyl}amino)pentanoyl]amino}methanesulfonic acid | 1.9 nM (0.99) |
| 138 | 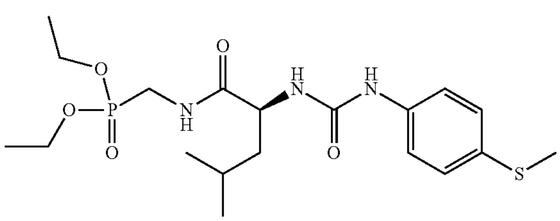 [SMILES: CCOP(=O)(CNC(=O)[C@H](CC(C)C)NC(=O)Nc1ccc(SC)cc1)OCC] | diethyl ({[(2S)-4-methyl-2-({[4-(methylsulfanyl)phenyl]carbamoyl}amino)pentanoyl]amino}methyl)phosphonate | 3.5 nM (0.91) |
| 139 | 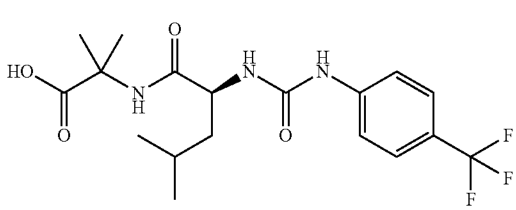 [SMILES: CC(C)C[C@H](NC(=O)Nc1ccc(C(F)(F)F)cc1)C(=O)NC(C)(C)C(=O)O] | 2-methyl-2-{[(2S)-4-methyl-2-({[4-(trifluoromethyl)phenyl]carbamoyl}amino)pentanoyl]amino}propanoic acid | 2.5 nM (0.92) |

TABLE 4-continued

| Compound number | Structure | IUPAC name | FPR2 EC50 (% eff) |
|---|---|---|---|
| 140 | 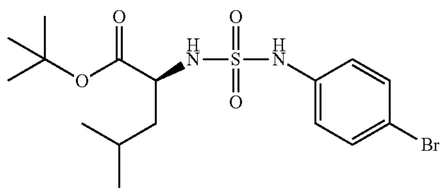 [SMILES: CC(C)C[C@H](NS(=O)(=O)Nc1ccc(Br)cc1)C(=O)OC(C)(C)C] | tert-butyl (2S)-2-{[(4-bromophenyl)sulfamoyl]amino}-4-methylpentanoate | NA |
| 141 | 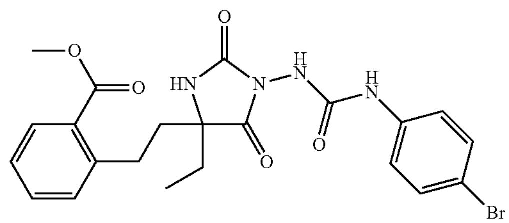 [SMILES: CCC1(CCc2ccccc2C(=O)OC)NC(=O)N(NC(=O)Nc2ccc(Br)cc2)C1=O] | methyl 2-[2-(1-{[(4-bromophenyl)carbamoyl]amino}-4-ethyl-2,5-dioxoimidazolidin-4-yl)ethyl]benzoate | 10.3 nM (0.92) |
| 142 | 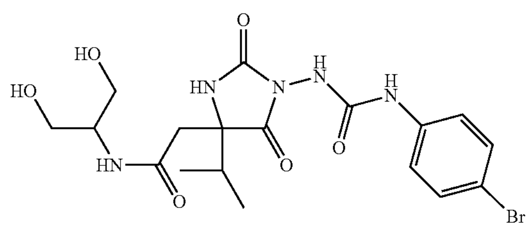 [SMILES: CC(C)C1(CC(=O)NC(CO)CO)NC(=O)N(NC(=O)Nc2ccc(Br)cc2)C1=O] | 2-[1-{[(4-bromophenyl)carbamoyl]amino}-2,5-dioxo-4-(propan-2-yl)imidazolidin-4-yl]-N-(1,3-dihydroxypropan-2-yl)acetamide | 13.8 nM (0.92) |
| 143 | 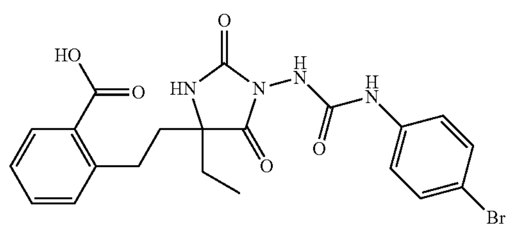 [SMILES: CCC1(CCc2ccccc2C(=O)O)NC(=O)N(NC(=O)Nc2ccc(Br)cc2)C1=O] | 2-[2-(1-{[(4-bromophenyl)carbamoyl]amino}-4-ethyl-2,5-dioxoimidazolidin-4-yl)ethyl]benzoic acid | 17.2 nM (1.0) |
| 144 | 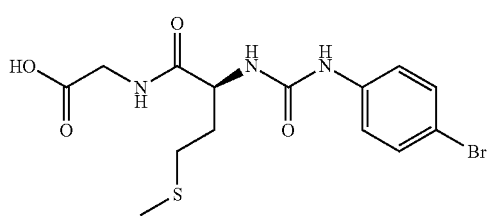 [SMILES: CSCC[C@H](NC(=O)Nc1ccc(Br)cc1)C(=O)NCC(=O)O] | {[(2S)-2-{[(4-bromophenyl)carbamoyl]amino}-4-(methylsulfanyl)butanoyl]amino}acetic acid | 6.3 nM (0.91) |
| 145 | 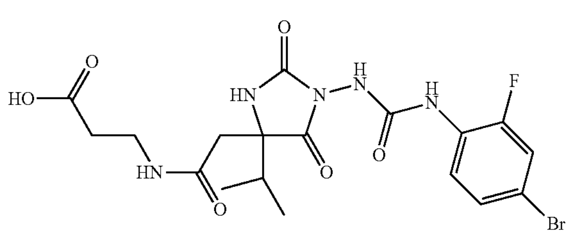 [SMILES: CC(C)C1(CC(=O)NCCC(=O)O)NC(=O)N(NC(=O)Nc2ccc(Br)cc2F)C1=O] | 3-({[1-{[(4-bromo-2-fluorophenyl)carbamoyl]amino}-2,5-dioxo-4-(propan-2-yl)imidazolidin-4-yl]acetyl}amino)propanoic acid | 1.0 nM (1.0) |
| 146 | 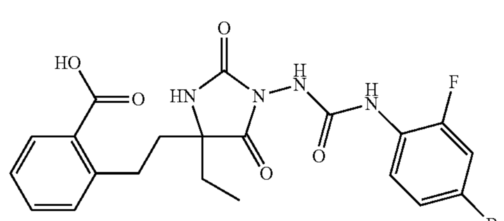 | 2-[2-(1-{[(4-bromo-2-fluorophenyl)carbamoyl]amino}-4-ethyl-2,5-dioxoimidazolidin-4-yl)ethyl]benzoic acid | 11.1 nM (1.0) |

TABLE 4-continued

| Compound number | Structure | IUPAC name | FPR2 EC50 (% eff) |
|---|---|---|---|
| 147 | 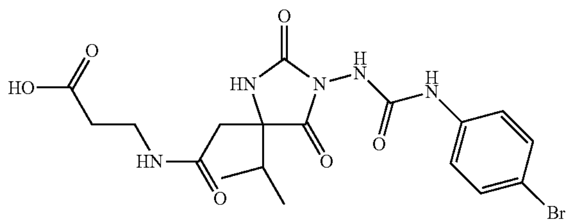 [SMILES: CC(C)C1(CC(=O)NCCC(=O)O)NC(=O)N(NC(=O)Nc2ccc(Br)cc2)C1=O] | 3-({[1-{[(4-bromophenyl)carbamoyl]amino}-2,5-dioxo-4-(propan-2-yl)imidazolidin-4-yl]acetyl}amino)propanoic acid | 3.9 nM (0.99) |
| 148 | 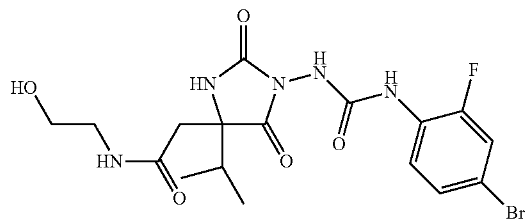 [SMILES: CC(C)C1(CC(=O)NCCO)NC(=O)N(NC(=O)Nc2ccc(Br)cc2F)C1=O] | 2-[1-{[(4-bromo-2-fluorophenyl)carbamoyl]amino}-2,5-dioxo-4-(propan-2-yl)imidazolidin-4-yl]-N-(2-hydroxyethyl)acetamide | 6.9 nM (0.98) |
| 149 | 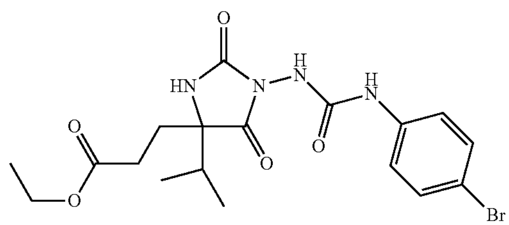 [SMILES: CCOC(=O)CCC1(C(C)C)NC(=O)N(NC(=O)Nc2ccc(Br)cc2)C1=O] | ethyl 3-[1-{[(4-bromophenyl)carbamoyl]amino}-2,5-dioxo-4-(propan-2-yl)imidazolidin-4-yl]propanoate | 6.6 nM (0.94) |
| 150 | 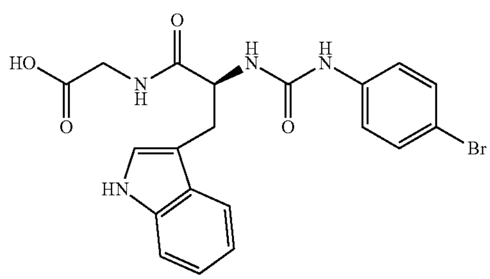 [SMILES: O=C(O)CNC(=O)[C@H](Cc1c[nH]c2ccccc12)NC(=O)Nc1ccc(Br)cc1] | {[2-{[(4-bromophenyl)carbamoyl]amino}-3-(1H-indol-3-yl)propanoyl]amino}acetic acid | 1.4 nM (0.98) |
| 151 | 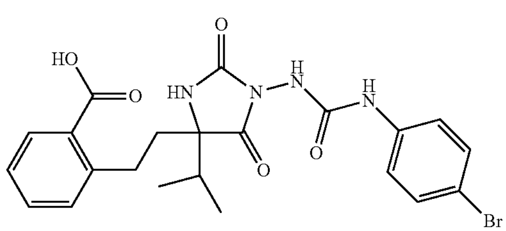 [SMILES: CC(C)C1(CCc2ccccc2C(=O)O)NC(=O)N(NC(=O)Nc2ccc(Br)cc2)C1=O] | 2-{2-[1-{[(4-bromophenyl)carbamoyl]amino}-2,5-dioxo-4-(propan-2-yl)imidazolidin-4-yl]ethyl}benzoic acid | 5.8 nM (1.0) |
| 152 | 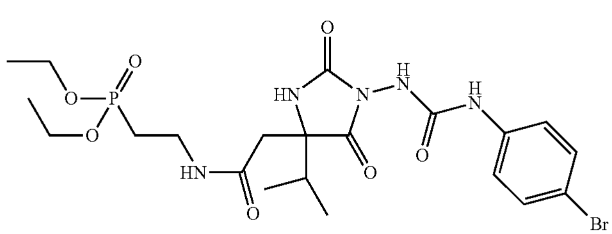 [SMILES: CCOP(=O)(CCNC(=O)CC1(C(C)C)NC(=O)N(NC(=O)Nc2ccc(Br)cc2)C1=O)OCC] | diethyl [2-({[1-{[(4-bromophenyl)carbamoyl]amino}-2,5-dioxo-4-(propan-2-yl)imidazolidin-4-yl]acetyl}amino)ethyl]phosphonate | 11 nM (1.0) |

TABLE 4-continued

| Compound number | Structure | IUPAC name | FPR2 EC50 (% eff) |
|---|---|---|---|
| 153 | 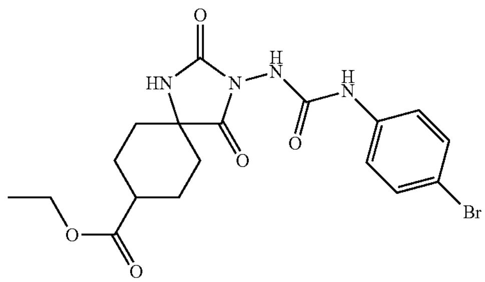 [SMILES: CCOC(=O)C1CCC2(CC1)NC(=O)N(NC(=O)Nc1ccc(Br)cc1)C2=O] | ethyl 3-{[(4-bromophenyl)carbamoyl]amino}-2,4-dioxo-1,3-diazaspiro[4.5]decane-8-carboxylate | 12 nM (0.99) |
| 154 | 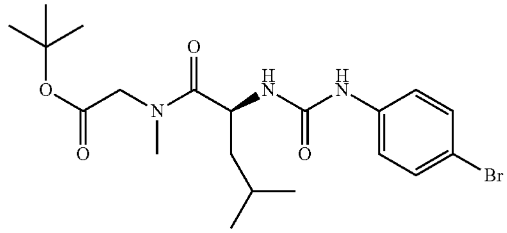 [SMILES: CC(C)C[C@H](NC(=O)Nc1ccc(Br)cc1)C(=O)N(C)CC(=O)OC(C)(C)C] | tert-butyl {[(2S)-2-{[(4-bromophenyl)carbamoyl]amino}-4-methylpentanoyl](methyl)amino}acetate | 12 nM (0.85) |
| 155 | 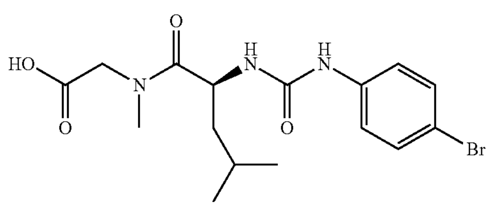 [SMILES: CC(C)C[C@H](NC(=O)Nc1ccc(Br)cc1)C(=O)N(C)CC(=O)O] | {[(2S)-2-{[(4-bromophenyl)carbamoyl]amino}-4-methylpentanoyl](methyl)amino}acetic acid | 1.0 nM (1.0) |

Immunohistochemistry:

Fluorescent immunohistochemistry with antibodies specific to FPR2 was used to determine localization in normal human skin. Anti-FPR2 antibody (Abcam) was used at a dilution of 1:200 to detect FPR2 protein.

Dermal Wound Healing Model:

Groups of 5 ICR male mice weighing 24-28 g were used. During the study, the tested animals were housed in individual cages. Under hexobarbital (90 mg/kg, i.p.) anesthesia, the shoulder and back region of each animal was shaved. A sharp punch (ID 12 mm) was applied to remove the skin including *panniculus carnosus* and adherent tissues. The wound area, traced onto clear plastic sheets, was measured by use of an Image—ProPlus (Media Cybernetics, Version 4.5.0.29) on days 1, 3, 5, 7, 9 and 11. Test substances and vehicle (Placebo, 20 µL/mouse) were administered topically (TOP) once daily post skin punch for a total of 10 consecutive days. The positive control of CGS-21680 in 0.5% CMC/PBS, pH 7.4 was given topically as the same regimen. The percent closure of the wound (%) was calculated, and wound half-closure time (CT50) was analyzed by linear regression using Graph-Prism (Graph Software USA). One-way ANOVA followed by Dunnett's test was applied for comparison between the treated and vehicle groups at each measurement time point. Differences are considered significant at $P<0.05$.

LL37-Induced Model of Rosacea in Mice:

Prior to dosing, animals are lightly anaesthetized with isofluorane and baseline right and left ear thickness measurements are made with a digital caliper (Mitutoyo 293-340). At t=−1 hrs, animals are lightly anaesthetized with isoflurane to allow topical application (dorsal side) of 10 µL of FPR2 agonist formulated in a vehicle consisting of PBS:ethanol (50:50), or vehicle control to both ears. At t=0 hr, mice are re-anaesthetized. Following ear thickness measurements, 20 uL of LL-37 (100 µM) is injected into the right ear, while PBS is injected into the left ear. Additional ear thickness measurements are taken at t=3 and 6 hours. After the last time point, mice are euthanized by $CO_2$ inhalation and ears collected for additional analyses.

In Vitro Human Skin Penetration Model:

Briefly, split-thickness human abdominal skin (~0.50 mm) sections from two donors were mounted in flow-through diffusion cells (PermeGear). FPR2 agonists are applied at a dose of 10 µL to a surface area of 0.64 $cm^2$ (n=7 per compound). PBS is pumped beneath the skin at a constant flow rate of ~42 µL/min. Receptor fluid samples are collected at 1, 3, 6, 12, and 24 hrs and analyzed by LC/MS/MS.

What is claimed is:

1. A method of treating dermal inflammation or a dermal disease in a subject in need of such treatment, the method comprising administering to the subject a pharmaceutical composition comprising a therapeutically effective amount of a formyl peptide receptor 2 (FPR2) agonist of Formula II:

Formula II

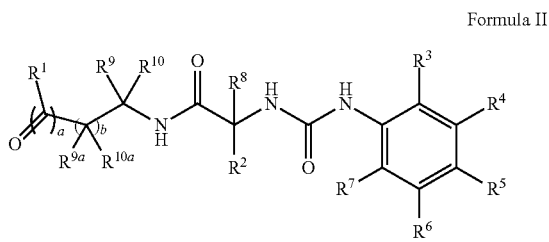

wherein:
a is 1 and b is 0;
a is 0 and b is 1; or
a is 1 and b is 1;
$R^1$ is optionally substituted $C_{1-8}$ alkyl, optionally substituted $C_{3-8}$ cycloalkyl, optionally substituted heterocycle, optionally substituted $C_{3-8}$ cycloalkyl, optionally substituted $C_{6-10}$ aryl, optionally substituted $C_{3-8}$ cycloalkenyl, $-NR^{11}R^{12}$ or $-OR^{13}$;
$R^2$ is optionally substituted $C_{1-8}$ alkyl or optionally substituted $C_{6-10}$ aryl;
$R^3$ is hydrogen, optionally substituted $C_{1-8}$ alkyl, halogen, $-COOR^{15}$, $-OR^{13}$, $-NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;
$R^4$ is hydrogen, optionally substituted $C_{1-8}$ alkyl, halogen, $-COOR^{15}$, $-OR^{13}$, $-NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;
$R^5$ is halogen, $-CF_3$ or $-S(O)_nR^{14}$;
n is 0, 1 or 2;
$R^6$ is hydrogen, optionally substituted $C_{1-8}$ alkyl, halogen, $-COOR^{15}$, $-OR^{13}$, $-NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;
$R^7$ is hydrogen, optionally substituted $C_{1-8}$ alkyl, halogen, $-COOR^{15}$, $-OR^{13}$, $-NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;
$R^8$ is hydrogen, optionally substituted $C_{1-8}$ alkyl or optionally substituted $C_{6-10}$ aryl;
$R^9$ is hydrogen, optionally substituted $C_{1-8}$ alkyl or optionally substituted $C_{6-10}$ aryl;
$R^{10}$ is hydrogen, optionally substituted $C_{1-8}$ alkyl or optionally substituted $C_{6-10}$ aryl;
$R^{9a}$ is hydrogen, optionally substituted $C_{1-8}$ alkyl or optionally substituted $C_{6-10}$ aryl;
$R^{10a}$ is hydrogen, optionally substituted $C_{1-8}$ alkyl or optionally substituted $C_{6-10}$ aryl;
$R^{11}$ is hydrogen or optionally substituted $C_{1-8}$ alkyl;
$R^{12}$ is hydrogen or optionally substituted $C_{1-8}$ alkyl;
$R^{13}$ is hydrogen or optionally substituted $C_{1-8}$ alkyl;
$R^{14}$ is hydrogen, $CF_3$ or optionally substituted $C_{1-8}$ alkyl; and
$R^{15}$ is hydrogen or optionally substituted $C_{1-8}$ alkyl;
or a pharmaceutically acceptable salt thereof;
wherein the dermal inflammation or dermal disease is selected from the group consisting of dermal wound healing, hypertrophic scars, keloids, burns, rosacea, atopic dermatitis, acne, psoriasis, seborrheic dermatitis, actinic keratoses, basal cell carcinoma, squamous cell carcinoma, melanoma, viral warts, photoaging, photodamage, melasma, post-inflammatory hyperpigmentation, disorders of pigmentation and alopecia, scarring and non-scarring forms;
and wherein the administration is by local delivery.

2. The method of claim 1, wherein the FPR2 agonist is a compound selected from the group consisting of:

{[(2S)-2-{[(4-bromophenyl)carbamoyl]amino}pentanoyl]amino}acetic acid

{[(2S,3S)-2-{[(4-bromophenyl)carbamoyl]amino}-3-methylpentanoyl]amino}acetic acid 2-{[(2S)-2-{[(4-bromophenyl)carbamoyl]amino}-4-methylpentanoyl]amino}-2-methylpropanoic acid {[(2S)-2-{[(4-bromo-2-fluorophenyl)carbamoyl]amino}-4-methylpentanoyl]amino}acetic acid {[(2S)-2-{[(4-bromophenyl)carbamoyl]amino}-4-methylpentanoyl]amino}acetic acid

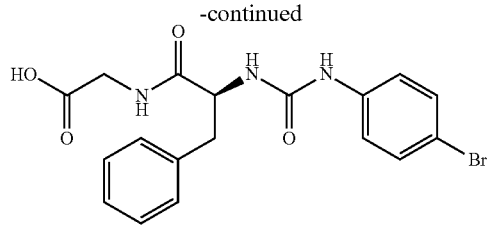

{[(2S)-2-{[(4-bromophenyl)carbamoyl]amino}-3-phenylpentanoyl]amino}acetic acid

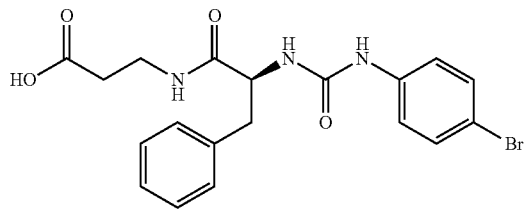

3-{[(2S)-2-{[(4-bromophenyl)carbamoyl]amino}-3-phenylpentanoyl]amino}propanoic acid

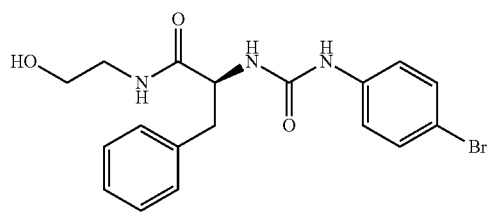

(2S)-2-{[(4-bromophenyl)carbamoyl]amino}-N-(2-hydroxyethyl)-3-phenylpropanamide

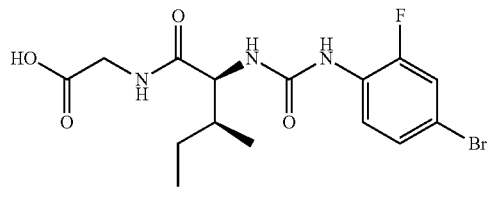

{[(2S,3S)-2-{[(4-bromo-2-fluorophenyl)carbamoyl]amino}-3-methylpentanoyl]amino}acetic acid

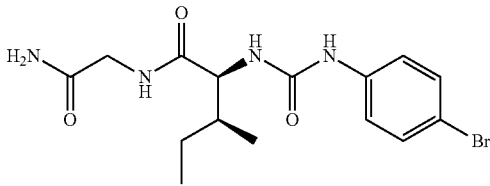

(2S,3S)-N-(2-amino-2-oxoethyl)-2-{[(4-bromophenyl)carbamoyl]amino}-3-methylpentanamide

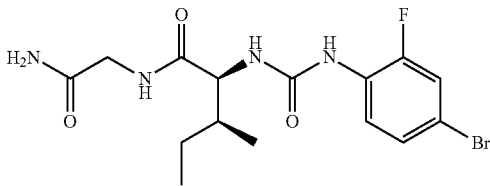

(2S,3S)-N-(2-amino-2-oxoethyl)-2-{[(4-bromo-2-fluorophenyl)carbamoyl]amino}-3-methylpentanamide

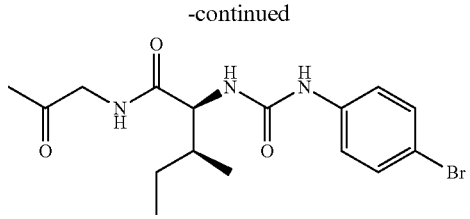

(2S,3S)-2-{[(4-bromophenyl)carbamoyl]amino}-3-methyl-N-(2-oxopropyl)pentanamide

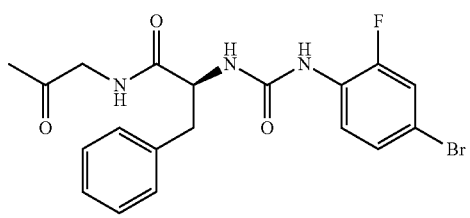

(2S)-2-{[(4-bromo-2-fluorophenyl)carbamoyl]amino}-N-(2-oxopropyl)-3-phenylpropanamide

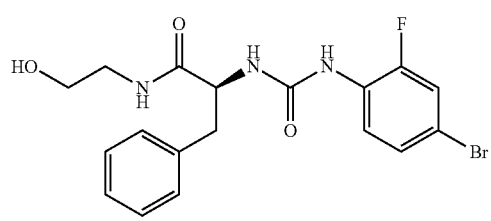

(2S)-2-{[(4-bromo-2-fluorophenyl)carbamoyl]amino}-N-(2-hydroxyethyl)-3-phenylpropanamide

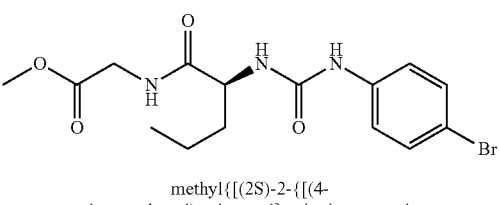

methyl{[(2S)-2-{[(4-bromophenyl)carbamoyl]amino}pentanoylamino}acetate

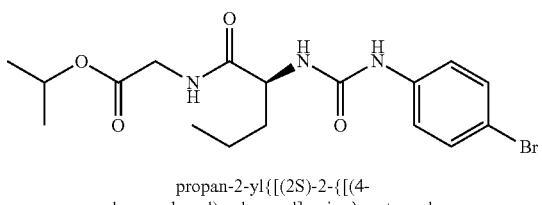

propan-2-yl{[(2S)-2-{[(4-bromophenyl)carbamoyl]amino}pentanoylamino}acetate

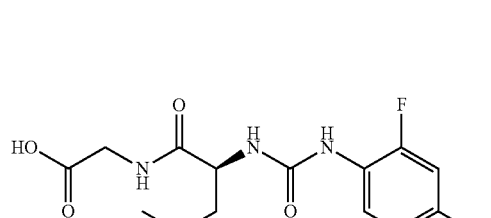

{[(2S)-2-{[(4-bromo-2-fluorophenyl)carbamoyl]amino}pentanoylamino}acetic acid

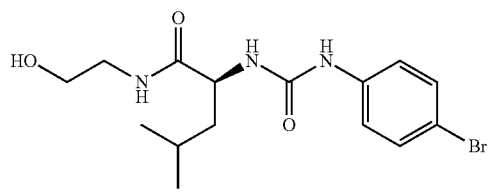

(2S)-2-{[(4-bromophenyl)carbamoyl]amino}-N-(2-hydroxyethyl)-4-methylpentanamide

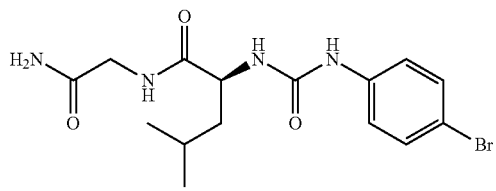

(2S)-N-(2-amino-2-oxoethyl)-2-{[(4-bromophenyl)carbamoyl]amino}-4-methylpentanamide

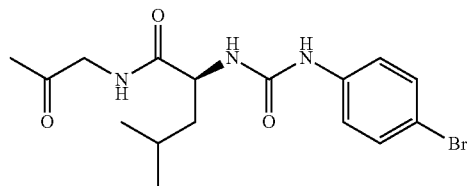

(2S)-2-{[(4-bromophenyl)carbamoyl]amino}-4-methyl-N-(2-oxopropyl)pentanamide

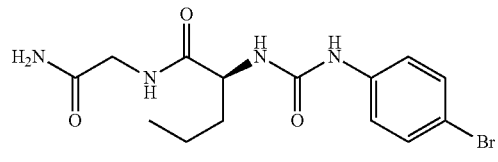

(2S)-N-(2-amino-2-oxoethyl)-2-{[(4-bromophenyl)carbamoyl]amino}pentanamide

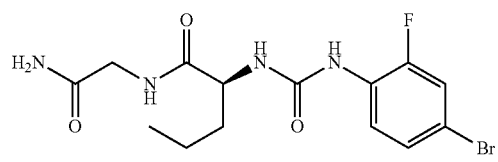

(2S)-N-(2-amino-2-oxoethyl)-2-{[(4-bromo-2-fluorophenyl)carbamoyl]amino}pentanamide

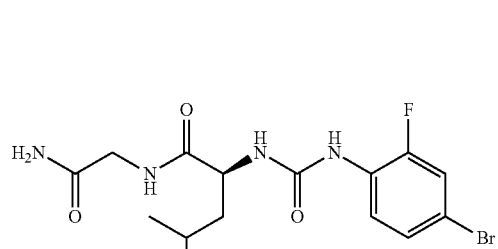

(2S)-N-(2-amino-2-oxoethyl)-2-{[(4-bromo-2-fluorophenyl)carbamoyl]amino}-4-methylpentanamide

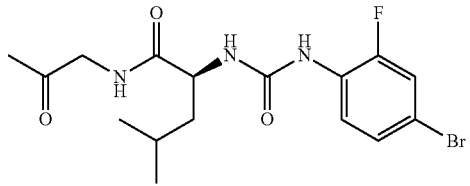

(2S)-2-{[(4-bromo-2-fluorophenyl)carbamoyl]amino}-4-methyl-N-(2-oxopropyl)pentanamide

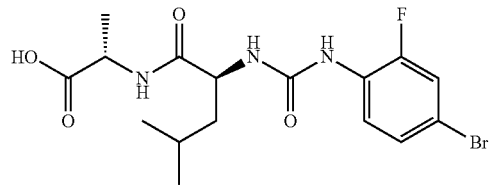

(2S)-2-{[(2S)-2-{[(4-bromo-2-fluorophenyl)carbamoyl]amino}-4-methylpentanoyl]amino}propanoic acid

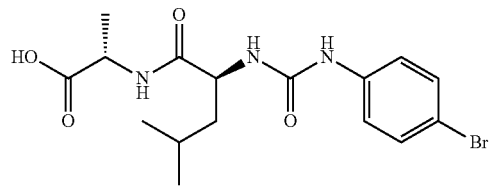

(2S)-2-{[(2S)-2-{[(4-bromophenyl)carbamoyl]amino}-4-methylpentanoyl]amino}propanoic acid

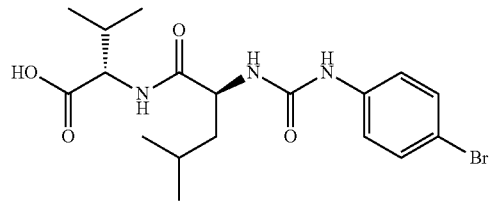

(2S)-2-{[(2S)-2-{[(4-bromophenyl)carbamoyl]amino}-4-methylpentanoyl]amino}-3-methyl butanoic acid

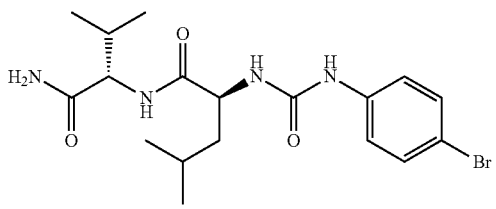

(2S)-N-[(2S)-1-amino-3-methyl-1-oxobutan-2-yl]-2-{[(4-bromophenyl)carbamoyl]amino}-4-methylpentanamide

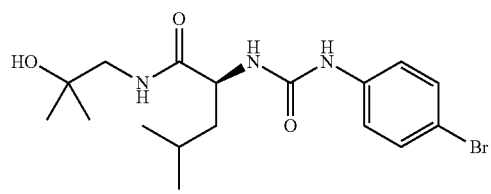

(2S)-2-{[(4-bromophenyl)carbamoyl]amino}-N-(2-hydroxy-2-methylpropyl)-4-methylpentanamide

85
-continued

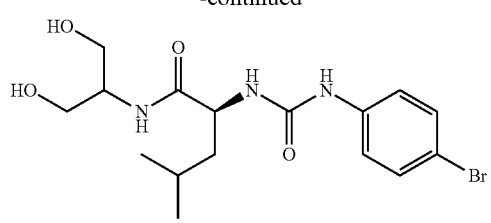

(2S)-2-{[(4-bromophenyl)carbamoyl]amino}-N-(1,3-dihydroxypropan-2-yl)-4-methylpentanamide

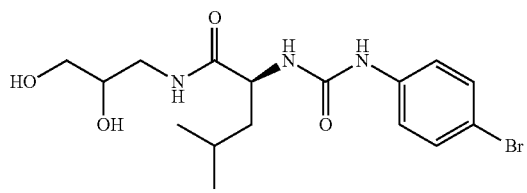

(2S)-2-{[(4-bromophenyl)carbamoyl]amino}-N-(2,3-dihydroxypropyl)-4-methylpentanamide

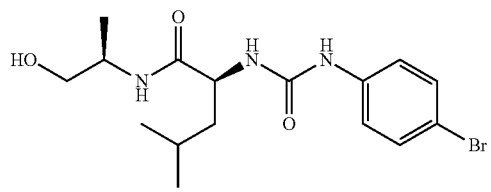

(2S)-2-{[(4-bromophenyl)carbamoyl]amino}-N-[(2R)-1-hydroxypropan-2-yl]-4-methylpentanamide

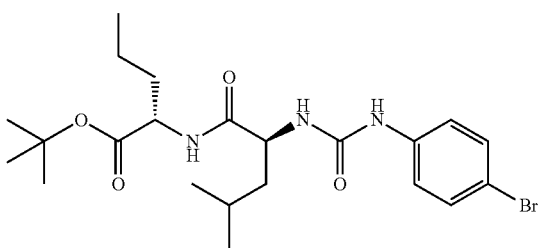

tert-butyl (2S)-2-{[(2S)-2-{[(4-bromophenyl)carbamoyl]amino}-4-methylpentanoyl]amino}pentanoate

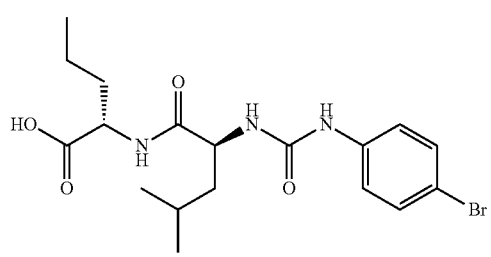

(2S)-2-{[(2S)-2-{[(4-bromophenyl)carbamoyl]amino}-4-methylpentanoyl]amino}pentanoic acid

86
-continued

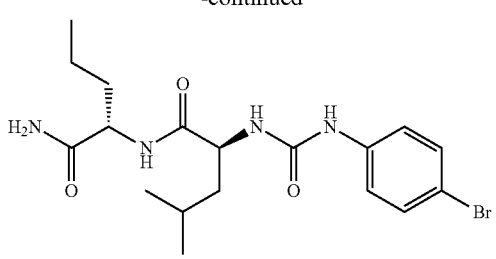

(2S)-N-[(2S)-1-amino-1oxopentan-2yl]-2-{[(4-bromophenyl)carbamoyl]amino}-4-methylpentanamide

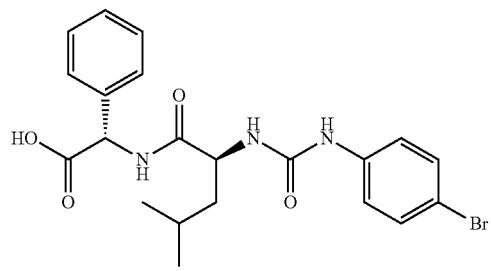

(2S)-{[(2S)-2-{[(4-bromophenyl)carbamoyl]amino}-4-methylpentanoyl]amino}(phenyl)ethanoic acid

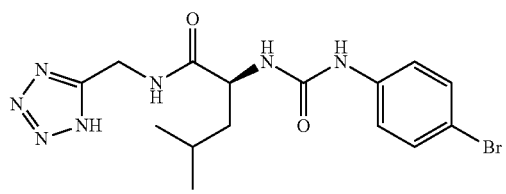

(2S)-2-{[(4-bromophenyl)carbamoyl]amino}-4-methyl-N-(1H-tetrazol-5-ylmethyl)pentanamide

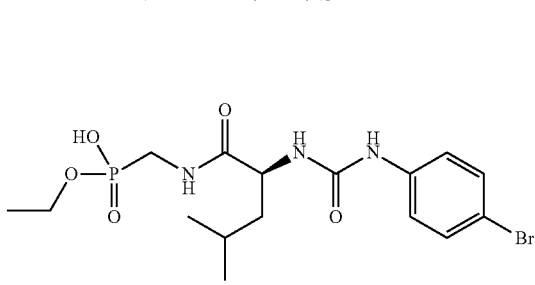

ethyl hydrogen ({[(2S)-2-{[(4-bromophenyl)carbamoyl]amino}-4-methylpentanoyl]amino}methyl)phosphonate

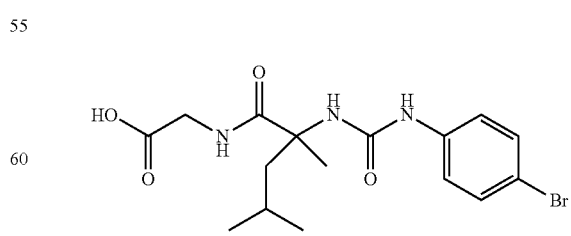

[(2-{[(4-bromophenyl)carbamoyl]amino}-2,4-dimethylpentanoyl)amino]acetic acid

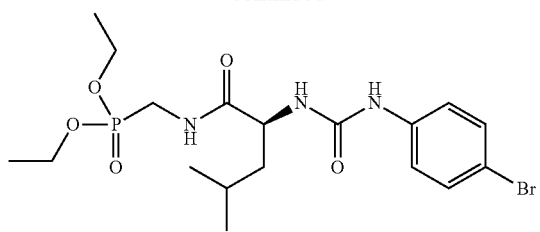

diethyl ({[(2S)-2-{[(4-bromophenyl)carbamoyl]amino}-4-methylpentanoyl]amino}methyl) phosphonate

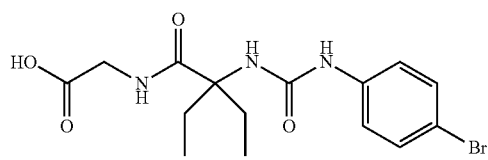

(2-{[(4-bromophenyl)carbamoyl]amino}-2-ethylbutanoyl)amino]acetic acid

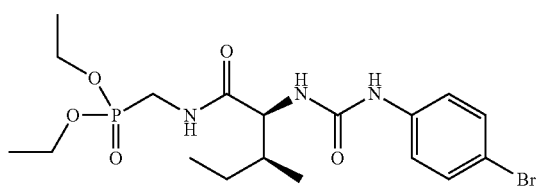

diethyl ({[(2S,3S)-2-{[(4-bromophenyl)carbamoyl]amino}-3-methylpentanoyl]amino}methyl) phosphonate

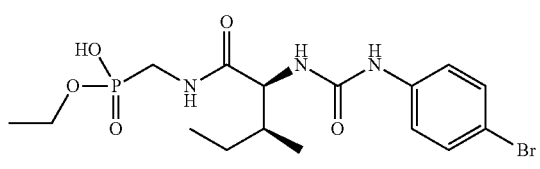

ethyl hydrogen ({[(2S,3S)-2-{[(4-bromophenyl)carbamoyl]amino}-3-methylpentanoyl]amino}methyl) phosphonate

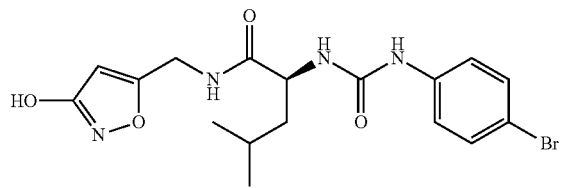

(2S)-2-{[(4-bromophenyl)carbamoyl]amino}-N-[(3-hydroxy-1,2-oxazol-5-yl)methyl]-4-methylpentanamide

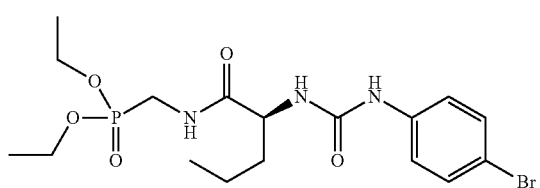

diethyl ({[(2S)-2-{[(4-bromophenyl)carbamoyl]amino}pentanoyl]amino}methyl)phosphonate

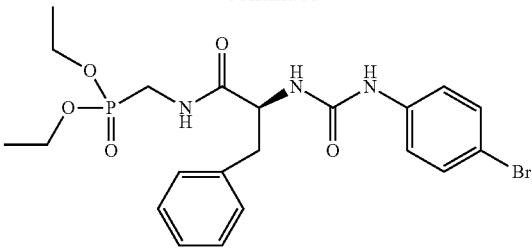

diethyl ({[(2S)-2-{[(4-bromophenyl)carbamoyl]amino}-3-phenylpropanoyl]amino}methyl) phosphonate

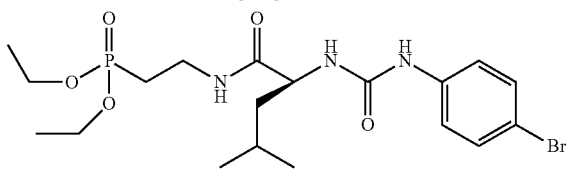

diethyl (2-{[(2S)-2-{[(4-bromophenyl)carbamoyl]amino}-4-methylpentanoyl]amino{ethyl) phosphonate

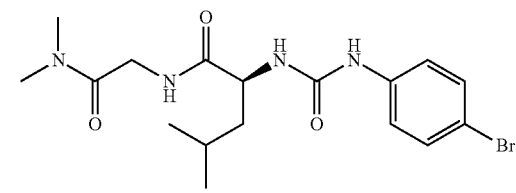

(2S)-2-{[(4-bromophenyl)carbamoyl]amino}-N-[2-(dimethylamino)-2-oxoethyl]-4-methylpentanamide

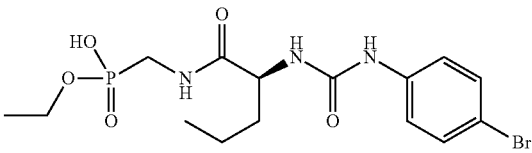

ethyl hydrogen ({[(2S)-2-{[(4-bromophenyl)carbamoyl]amino}pentanoyl]amino}methyl)phosphonate

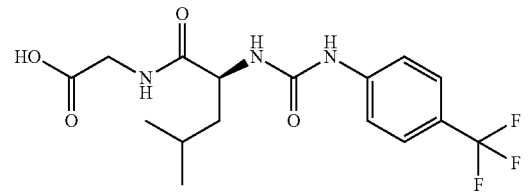

{[(2S)-4-methyl-2-({[(4-(trifluoromethyl)phenyl]carbamoyl}amino)p(dimethylamino)-2-oxoethyl]-4-entanoyl]amino}acetic acid

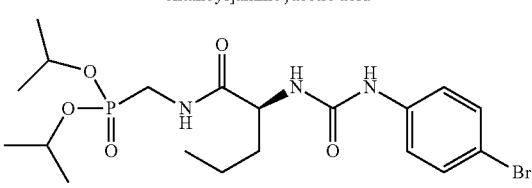

dipropan-2-yl({[(2S)-2-{[(4-bromophenyl)carbamoyl]amino}pentanoyl]amino}methyl)phosphonate -continued

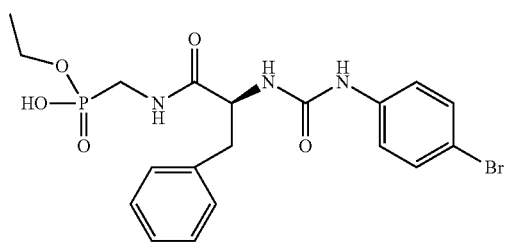

ethyl hydrogen ({[(2S)-2-{[(4-bromophenyl)carbamoyl]amino}-3-phenylpropanoyl]amino}methyl) phosphonate

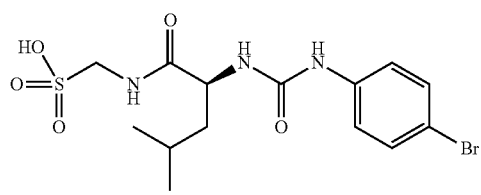

{[(2S)-2-{[(4-bromophenyl)carbamoyl]amino}-4-methylpentanoyl]amino}methanesulfonic acid

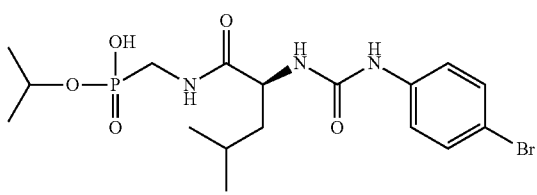

propan-2yl hydrogen{[(2-{[(4-bromophenyl)carbamoyl]amino}pentanoyl) amino]methyl}phosphonate

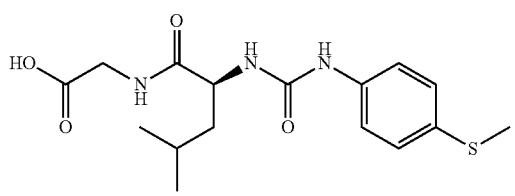

{[(2S)-4-methyl-2-{[(4-methylsulfanyl)phenyl)carbamoyl]amino) pentanoyl]amino}acetic acid

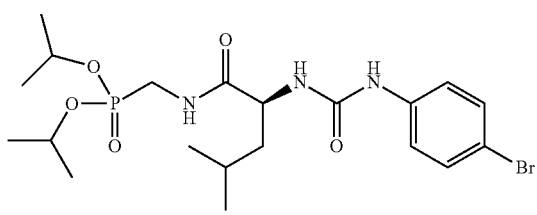

dipropan-2-yl({[(2S)-2-{[(4-bromophenyl)carbamoyl]amino}-4-methylpentanolyl]amino}methyl) phosphonate -continued

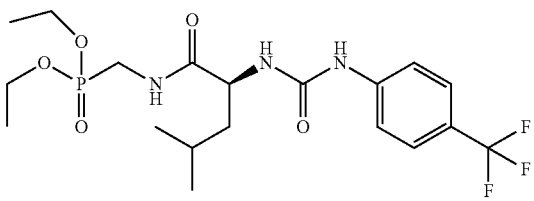

diethyl({[(2S)-4-methyl-2-({[(4-(trifluoromethyl)phenyl]carbamoyl}amino)p entanoyl]amino}methyl)phosphonate

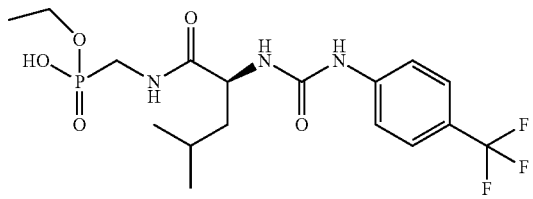

ethyl hydrogen({[(2S)-4-methyl-2-({[(4-(trifluoromethyl)phenyl]carbamoyl}amino)p entanoyl]amino}methyl)phosphonate

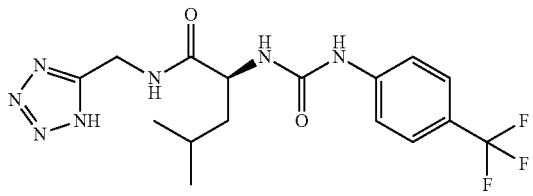

(2S)-4-methyl-N-(1H-tetrazol-5-ylmethyl)-2-({[4-(trifluoromethyl)phenyl]carbamoyl}amino) pentanamide

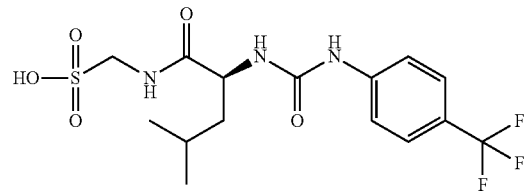

{[(2S)-4-methyl-2-({[4-(trifluoromethyl)phenyl]carbamoyl}amino) pentanoyl]amino}methanesulfonic acid

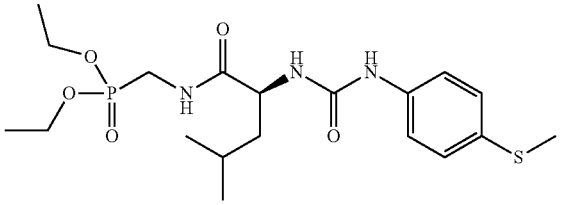

diethyl {[(2S)-4-methyl-2-({[4-(methylsulfanyl)phenyl]carbamoyl}amino) pentanoyl]amino}methyl)phosphonate

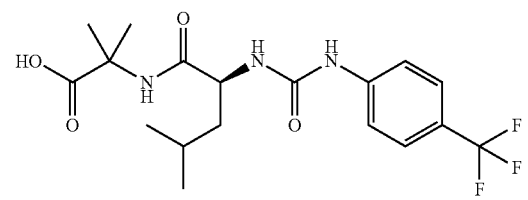

2-methyl-2-{[(2S)-4-methyl-2-({[4-(trifluoromethyl)phenyl]carbamoyl}amino)p entanoyl]amino}propanoic acid

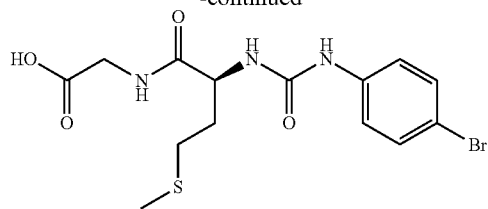

{[(2S)-2-({[4-bromophenyl]carbamoyl]amino}-4-(methylsulfanyl)butanoyl]amino}acetic acid

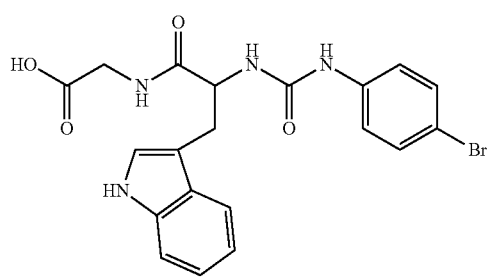

{[(2S)-2-({[4-bromophenyl]carbamoyl]amino}-3-(1H-indol-3-yl)propanoyl]amino}acetic acid

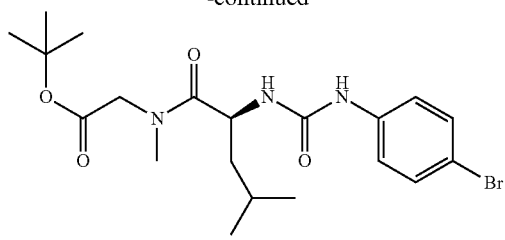

tert-butyl{[(2S)-2-({[4-bromophenyl]carbamoyl]amino}-4-methylpentanoyl](methyl)amino}acetate

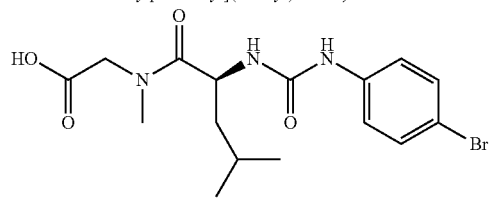

{[(2S)-2-({[4-bromophenyl]carbamoyl]amino}-4-methylpentanoyl](methyl)amino}acetic acid and pharmaceutically acceptable salts thereof.

3. The method of claim 1, wherein the local delivery is topical dermal delivery.

4. The method of claim 3, wherein the pharmaceutical composition is in a form selected from the group consisting of a cream, a lotion, a gel, a solution, a spray, a foam, a suspension and an emulsion.

* * * * *